(12) United States Patent
Fisher

(10) Patent No.: US 11,607,461 B2
(45) Date of Patent: Mar. 21, 2023

(54) COMPOSITIONS AND METHODS FOR GENETICALLY MODIFYING MYOSIN PHOSPHATASE TARGET SUBUNIT (MYPT1) GENE FOR LOWERING BLOOD PRESSURE

(71) Applicant: University of Maryland, Baltimore, Baltimore, MD (US)

(72) Inventor: Steven A. Fisher, Columbia, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 231 days.

(21) Appl. No.: 16/078,332

(22) PCT Filed: Mar. 23, 2017

(86) PCT No.: PCT/US2017/023877
§ 371 (c)(1),
(2) Date: Aug. 21, 2018

(87) PCT Pub. No.: WO2017/165688
PCT Pub. Date: Sep. 28, 2017

(65) Prior Publication Data
US 2019/0046660 A1 Feb. 14, 2019

Related U.S. Application Data

(60) Provisional application No. 62/312,196, filed on Mar. 23, 2016.

(51) Int. Cl.
*A61K 48/00* (2006.01)
*C12N 15/113* (2010.01)
*C12N 15/10* (2006.01)
*C12N 15/86* (2006.01)
*A61K 35/761* (2015.01)
*C12N 9/22* (2006.01)
*A01K 67/027* (2006.01)

(52) U.S. Cl.
CPC ........ *A61K 48/005* (2013.01); *A01K 67/0275* (2013.01); *A01K 67/0276* (2013.01); *A61K 35/761* (2013.01); *C12N 9/22* (2013.01); *C12N 15/102* (2013.01); *C12N 15/1137* (2013.01); *C12N 15/86* (2013.01); *A01K 2217/05* (2013.01); *A01K 2217/075* (2013.01); *A01K 2217/15* (2013.01); *A01K 2217/206* (2013.01); *A01K 2227/105* (2013.01); *A01K 2267/0375* (2013.01); *A01K 2267/0393* (2013.01); *C12N 2310/20* (2017.05); *C12N 2750/14143* (2013.01); *C12N 2800/80* (2013.01)

(58) Field of Classification Search
None
See application file for complete search history.

(56) References Cited

U.S. PATENT DOCUMENTS

2015/0232881 A1   8/2015 Glucksmann

FOREIGN PATENT DOCUMENTS

WO     2000043012 A1     7/2000
WO     WO-2004058990 A2 *  7/2004  .......... C12Q 1/6883

OTHER PUBLICATIONS

Reho et al. "Redox signaling and splicing dependent change in myosin phosphatase underlie early versus late changes in NO vasodilator reserve in a mouse LPS model of sepsis." American Journal of Physiology—Heart and Circulatory Physiology 308.9 (2015): H1039-H1050. (Year: 2015).*
Sun et al. "CRISPR/Cas9 mediated deletion of the angiotensinogen gene reduces hypertension: a potential for cure?." Hypertension 77.6 (2021): 1990-2000. (Year: 2021).*
Uddin et al. "CRISPR gene therapy: applications, limitations, and implications for the future." Frontiers in Oncology 10 (2020): 1387. (Year: 2020).*
Dippold et al., Myosin Phosphatase Isoforms as Determinants of Smooth Muscle Contractile Function and Calcium Sensitivity of Force Production, Microcirculation, 21:239-248 (2014).
Fu et al., Tra2β Protein Is Required for Tissue-specific Splicing of a Smooth Muscle Myosin Phosphatase Targeting Subunit Alternative Exon, J Biol Chem, 287:1657-85 (2012).
Han et al., Altered Reactivity of Tertiary Mesenteric Arteries Following Acute Myocardial Ischemia, J Vas Res, 50:100-108 (2013).
Khatri et al., Role of Myosin Phosphatase Isoforms in cGMP-mediated Smooth Muscle Relaxation, J Biol Chem, 276:37250-37257 (2001).
Konik et al., The role of pulmonary vascular contractile protein expression in pulmonary arterial hypertension, J Mol Cell Cardiol, 65:147-155 (2013).
Lu et al., Uterine artery myosin phosphatase isoform switching and increased sensitivity to SNP in a rat L-NAME model of hypertension of pregnancy, Am J Physiol Cell Physiol, 294:564-571 (2008).
Kotterman et al., Engineering adeno-associated viruses for clinical gene therapy, Nature Reviews Genetics, 15:445-451 (2014).
Payne et al., Dynamic changes in expression of myosin phosphatase in a model of portal hypertension, Am J Physiol Heart Circ Physiol, 286:1801-1810 (2004).
Payne et al., Myosin phosphatase isoform switching in vascular smooth muscle development, Journal of Molecular and Cellular Cardiology, 40:274-282 (2006).

(Continued)

Primary Examiner — Emily A Cordas
(74) Attorney, Agent, or Firm — Nevrivy Patent Law Group P.L.L.C.

(57) ABSTRACT

The present invention provides a method of lowering blood pressure in a subject, comprising genetically modifying a myosin phosphatase target subunit (Mypt1) gene in a vascular smooth muscle cell of the subject, whereby the genetic modification of Mypt1 results in a deletion or inactivation of exon 24. The invention further provides vectors, host cells, and compositions useful for carrying out the methods of the invention.

20 Claims, 21 Drawing Sheets

Specification includes a Sequence Listing.

(56) References Cited

OTHER PUBLICATIONS

Reho et al., Neural programming of mesenteric and renal arteries John, Am J Physiol Heart Circ Physiol, 307:563-573 (2014).

Reho et al., Smooth muscle contractile diversity in the control of regional circulations, Am J Physiol Heart Circ Physiol, 306:163-172 (2014).

Zhang et al., Conditioning Effect of Blood Flow on Resistance Artery Smooth Muscle Myosin Phosphatase, Circulation Research, 100:730-737 (2007).

Shukla et al., Tra2β as a novel mediator of vascular smooth muscle diversification, Circ Res, 103:485-492 (2008).

Wirth et al., G12-G13-LARG-mediated signaling in vascular smooth muscle is required for salt-induced hypertension, Nat Med, 14:64-68 (2008).

Zheng et al., Myosin phosphatase isoforms and related transcripts in the pig coronary circulation and effects of exercise and chronic occlusion, Microvasc Res, 98:166-171 (2015).

Zheng et al., TRA2β controls Mypt1 exon 24 splicing in the developmental maturation of mouse mesenteric artery smooth muscle, Am J Physiol Cell Physiol, 308:289-296 (2015).

Chylinski et al., The tracrRNA and Cas9 families of type II CRISPR-Cas immunity systems, RNA Biology 10:726-737 (2013).

Qiao et al., Myosin Phosphatase Target Subunit 1 (MYPT1) Regulates the Contraction and Relaxation of Vascular Smooth Muscle and Maintains Blood Pressure, Journal of Biological Chemistry, 289:22512-22523 (2014).

Reho et al., Redox signaling and splicing dependent change in myosin phosphatase underlie early versus late changes in NO vasodilator reserve in a mouse LPS model of sepsis, American Journal of Physiology, Heart and Circulatory Physiology, 308:H1039-H1050 (2015).

International Search Report from International Appl. No. PCT/US17/23877, dated Aug. 17, 2017.

GenBank AI202675.1, qs80b06.x1 NCI_CGAP_Pr28 *Homo sapiens* cDNA clone Image:1944371 3similar to TR: O14974 O14974 Myosin Phosphatase Target Subunit 1.;, mRNA Sequence, Jan. 4, 2011, [database online], [retrieved on Jul. 19, 2017] Retrieved from <https://www.ncbi.nlm.nih.gov/nucest/AI202675>.

* cited by examiner

FIG. 1A

```
         LoxP
-334     ─────
tatacgtagaataacttcgtatagcatacattatacgaagttatatatgtatgtgtttgtatatacacac   82
acatatttacaaagttgtaaggatcaaatatgaagctatttgctggtgttgagaagacagtggttatgtgaattt
gtcattgttatgttcttcctagcagagtcttttaataagtaacacatgctctaaacacattataataagtgtatg
acattactaaatataaccattaattgtaatctgggaagaatgtcattgagatagttcagtgtgtaactaaaatgta
aatgtttgtatctgaagatgaccgcagatctctcggagctctgcgactgaccagtcttacagttcatcc   406
                            EX24
                     +336
atgactgctgcttcgtttgcttaacacttacacaatgcttctcatataaggaaaataaacaggacactgcaataat
acattgtgttgctttgcctgtcacttcttgaattgagtaaatgttgtgctgtcctatattcaccgca
ttaatgtacacactgtatcaacctgactaaatctgactaatcgtgtagagtagtaaactaactaactcacagtaaac
attgtgagcagaagagatgagtctctgagaatctgtgagaatactcctatacattataacgaagttataagtttcgt   722
                               ─────
                                LoxP                                    SEQ ID
                                                                        NO:29
```

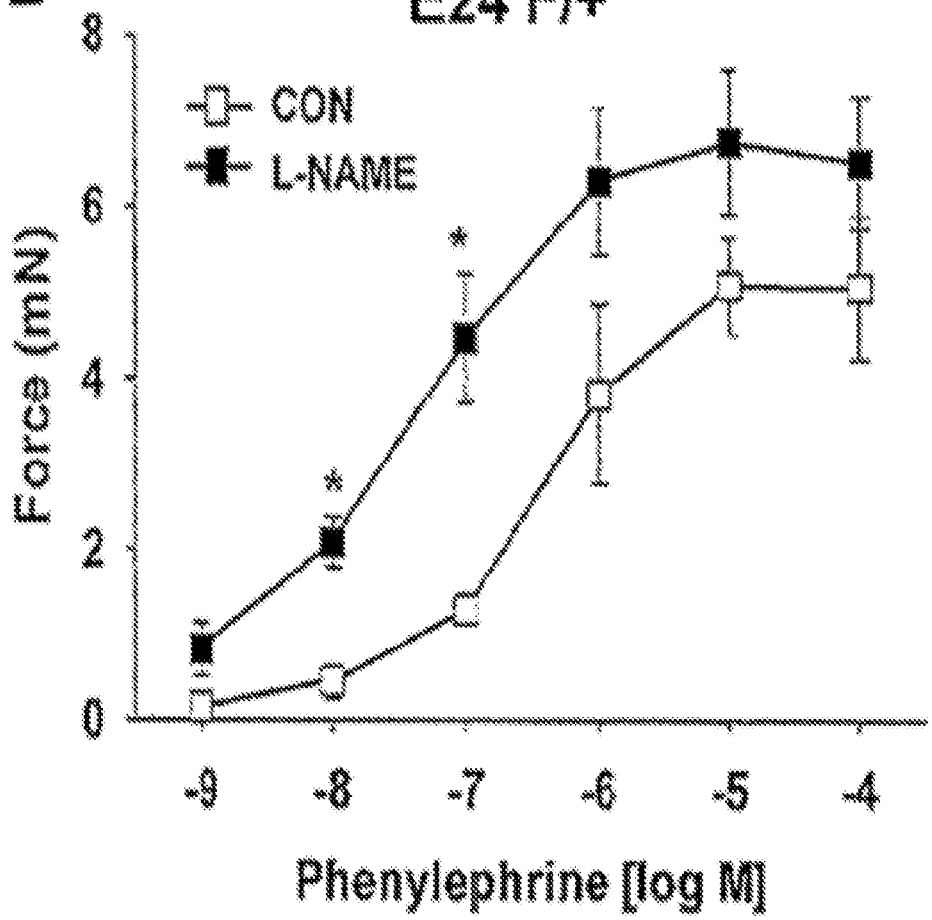

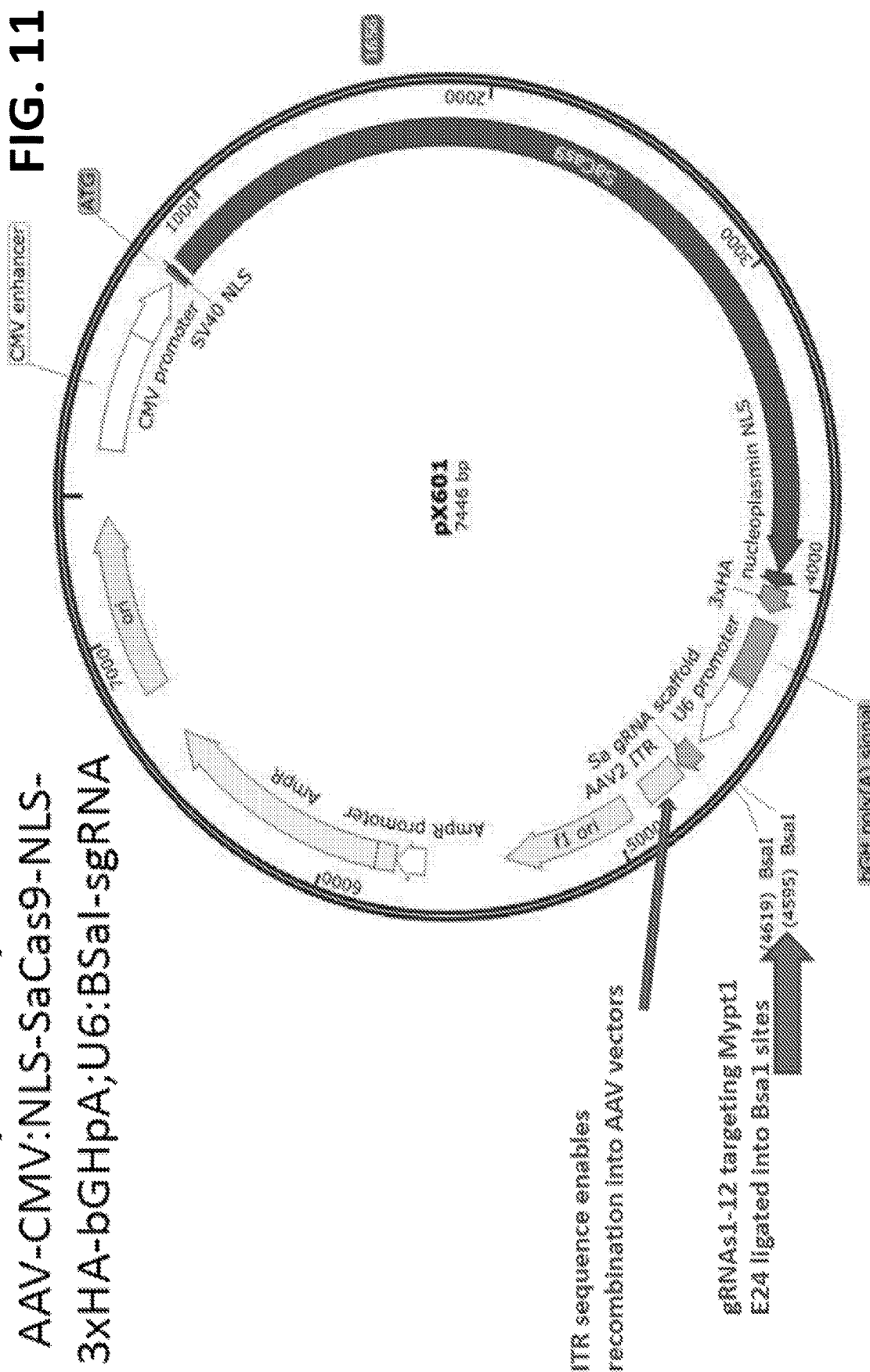

SEQUENCE LISTING

```
<160> NUMBER OF SEQ ID NOS: 40

<210> SEQ ID NO 1
<211> LENGTH: 20
<212> TYPE: DNA
<213> ORGANISM: Homo sapiens

<400> SEQUENCE: 1
cggcaagagt cagtatcttc                                                    20

<210> SEQ ID NO 2
<211> LENGTH: 22
<212> TYPE: DNA
<213> ORGANISM: Artificial sequence
<220> FEATURE:
<223> OTHER INFORMATION: primer

<400> SEQUENCE: 2
gagggcctat ttcccatatt cc                                                 22

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
atgtttaggc atgccgatgt                                                    20

<210> SEQ ID NO 4
<211> LENGTH: 22
<212> TYPE: DNA
<213> ORGANISM: Artificial sequence
<220> FEATURE:
<223> OTHER INFORMATION: primer

<400> SEQUENCE: 4
gctttgactt tctgggaaga tg                                                 22

<210> SEQ ID NO 5
<211> LENGTH: 20
<212> TYPE: DNA
<213> ORGANISM: Homo sapiens

<400> SEQUENCE: 5
atgtttaggc atgccgatgt                                                    20

<210> SEQ ID NO 6
<211> LENGTH: 20
<212> TYPE: DNA
<213> ORGANISM: Homo sapiens

<400> SEQUENCE: 6
ggtacttaaa agacgatcag                                                    20

<210> SEQ ID NO 7
<211> LENGTH: 20
```

<212> TYPE: DNA
<213> ORGANISM: Homo sapiens

<400> SEQUENCE: 7
atgtgatttt aaaaagtaga                                           20

<210> SEQ ID NO 8
<211> LENGTH: 20
<212> TYPE: DNA
<213> ORGANISM: Homo sapiens

<400> SEQUENCE: 8
actgtaaatg ttaatgtttt                                           20

<210> SEQ ID NO 9
<211> LENGTH: 20
<212> TYPE: DNA
<213> ORGANISM: Homo sapiens

<400> SEQUENCE: 9
cattatttat taatctggga                                           20

<210> SEQ ID NO 10
<211> LENGTH: 20
<212> TYPE: DNA
<213> ORGANISM: Homo sapiens

<400> SEQUENCE: 10
gtatctgaaa ggtgaccggc                                           20

<210> SEQ ID NO 11
<211> LENGTH: 20
<212> TYPE: DNA
<213> ORGANISM: Homo sapiens

<400> SEQUENCE: 11
ttgctttttg cataacaccc                                           20

<210> SEQ ID NO 12
<211> LENGTH: 20
<212> TYPE: DNA
<213> ORGANISM: Homo sapiens

<400> SEQUENCE: 12
cccttaaatg ataagcattc                                           20

<210> SEQ ID NO 13
<211> LENGTH: 20
<212> TYPE: DNA
<213> ORGANISM: Homo sapiens

<400> SEQUENCE: 13
agaatgctta tcatttaagg                                           20

<210> SEQ ID NO 14
<211> LENGTH: 20
<212> TYPE: DNA
<213> ORGANISM: Homo sapiens

<400> SEQUENCE: 14
tttattttaa acttgtttca                                           20

<210> SEQ ID NO 15

```
<211> LENGTH: 20
<212> TYPE: DNA
<213> ORGANISM: Homo sapiens

<400> SEQUENCE: 15
ttatgtgtag cattaatgca                                                   20

<210> SEQ ID NO 16
<211> LENGTH: 20
<212> TYPE: DNA
<213> ORGANISM: Homo sapiens

<400> SEQUENCE: 16
atacaaagct ataaagtcag                                                   20

<210> SEQ ID NO 17
<211> LENGTH: 20
<212> TYPE: DNA
<213> ORGANISM: Homo sapiens

<400> SEQUENCE: 17
aataatggct agtacacatt                                                   20

<210> SEQ ID NO 18
<211> LENGTH: 81
<212> TYPE: RNA
<213> ORGANISM: Artificial sequence
<220> FEATURE:
<223> OTHER INFORMATION: partial gRNA sequence

<400> SEQUENCE: 18
guuuuaguac ucuggaaaca gaaucuacua aaacaaggca aaaugccgug uuuaucucgu       60
caacuuguug gcgagauuuu u                                                 81

<210> SEQ ID NO 19
<211> LENGTH: 101
<212> TYPE: RNA
<213> ORGANISM: Artificial sequence
<220> FEATURE:
<223> OTHER INFORMATION: sgRNA6

<400> SEQUENCE: 19
guaucugaaa ggugaccggc guuuuaguac ucuggaaaca gaaucuacua aaacaaggca       60
aaaugccgug uuuaucucgu caacuuguug gcgagauuuu u                          101

<210> SEQ ID NO 20
<211> LENGTH: 102
<212> TYPE: RNA
<213> ORGANISM: Artificial sequence
<220> FEATURE:
<223> OTHER INFORMATION: sgRNA11

<400> SEQUENCE: 20
guuaugugua gcauuaaugc aguuuuagua cucuggaaac agaaucuacu aaaacaaggc       60
aaaaugccgu guuuaucucg ucaacuuguu ggcgagauuu uu                         102

<210> SEQ ID NO 21
<211> LENGTH: 102
<212> TYPE: RNA
<213> ORGANISM: Artificial sequence
<220> FEATURE:
<223> OTHER INFORMATION: sgRNA5
```

```
<400> SEQUENCE: 21
gcauuauuua uuaaucuggg aguuuuagua cucuggaaac agaaucuacu aaaacaaggc      60
aaaaugccgu guuuaucucg ucaacuuguu ggcgagauuu uu                        102

<210> SEQ ID NO 22
<211> LENGTH: 102
<212> TYPE: RNA
<213> ORGANISM: Artificial sequence
<220> FEATURE:
<223> OTHER INFORMATION: sgRNA9

<400> SEQUENCE: 22
gagaaugcuu aucauuuaag gguuuuagua cucuggaaac agaaucuacu aaaacaaggc      60
aaaaugccgu guuuaucucg ucaacuuguu ggcgagauuu uu                        102

<210> SEQ ID NO 23
<211> LENGTH: 102
<212> TYPE: RNA
<213> ORGANISM: Artificial sequence
<220> FEATURE:
<223> OTHER INFORMATION: sgRNA12

<400> SEQUENCE: 23
gauacaaagc uauaaaguca gguuuuagua cucuggaaac agaaucuacu aaaacaaggc      60
aaaaugccgu guuuaucucg ucaacuuguu ggcgagauuu uu                        102

<210> SEQ ID NO 24
<211> LENGTH: 1053
<212> TYPE: PRT
<213> ORGANISM: Staphylococcus aureus

<400> SEQUENCE: 24
```

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

```
Leu Asp Gln Ser Phe Ile Asp Thr Tyr Ile Asp Leu Glu Thr Arg
            195                 200                 205
Arg Thr Tyr Tyr Glu Gly Pro Gly Gly Ser Pro Phe Gly Trp Lys
210                 215                 220
Asp Ile Lys Glu Trp Tyr Glu Met Leu Met Gly His Cys Thr Tyr Phe
225                 230                 235                 240
Pro Glu Glu Leu Arg Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
            260                 265                 270
Glu Lys Leu Glu Tyr Tyr Glu Lys Phe Gln Ile Ile Glu Asn Val Phe
            275                 280                 285
Lys Gln Lys Lys Lys Pro Thr Leu Lys Gln Ile Ala Lys Glu Ile Leu
290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
            355                 360                 365
Thr Asn Leu Asn Ser Glu Leu Thr Gln Glu Glu Ile Glu Gln Ile Ser
            370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
            500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
            530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Asn Ser Lys Lys Gly Asn Arg Thr Pro Phe Gln Tyr Leu
            580                 585                 590
Ser Ser Ser Asp Ser Lys Ile Ser Tyr Glu Thr Phe Lys Lys His Ile
            595                 600                 605
```

```
Leu Asn Leu Ala Lys Gly Lys Gly Arg Ile Ser Lys Thr Lys Lys Glu
            610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
   1010                1015                1020
```

```
Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 25
<211> LENGTH: 1137
<212> TYPE: PRT
<213> ORGANISM: Artificial sequence
<220> FEATURE:
<223> OTHER INFORMATION: artificial saCas9 amino acid sequence

<400> SEQUENCE: 25

Met Gly Gly Arg Arg Val Arg Trp Glu Val Tyr Ile Ser Arg Ala Leu
1               5                   10                  15

Trp Leu Thr Thr Gly Ala Thr Met Ala Pro Lys Lys Arg Lys Val
            20                  25                  30

Gly Ile His Gly Val Pro Ala Ala Lys Arg Asn Tyr Ile Leu Gly Leu
            35                  40                  45

Asp Ile Gly Ile Thr Ser Val Gly Tyr Gly Ile Ile Asp Tyr Glu Thr
    50                  55                  60

Arg Asp Val Ile Asp Ala Gly Val Arg Leu Phe Lys Glu Ala Asn Val
65                  70                  75                  80

Glu Asn Asn Glu Gly Arg Arg Ser Lys Arg Gly Ala Arg Arg Leu Lys
                85                  90                  95

Arg Arg Arg Arg His Arg Ile Gln Arg Val Lys Lys Leu Leu Phe Asp
                100                 105                 110

Tyr Asn Leu Leu Thr Asp His Ser Glu Leu Ser Gly Ile Asn Pro Tyr
            115                 120                 125

Glu Ala Arg Val Lys Gly Leu Ser Gln Lys Leu Ser Glu Glu Glu Phe
        130                 135                 140

Ser Ala Ala Leu Leu His Leu Ala Lys Arg Arg Gly Val His Asn Val
145                 150                 155                 160

Asn Glu Val Glu Glu Asp Thr Gly Asn Glu Leu Ser Thr Lys Glu Gln
                165                 170                 175

Ile Ser Arg Asn Ser Lys Ala Leu Glu Glu Lys Tyr Val Ala Glu Leu
            180                 185                 190

Gln Leu Glu Arg Leu Lys Lys Asp Gly Glu Val Arg Gly Ser Ile Asn
        195                 200                 205

Arg Phe Lys Thr Ser Asp Tyr Val Lys Glu Ala Lys Gln Leu Leu Lys
    210                 215                 220

Val Gln Lys Ala Tyr His Gln Leu Asp Gln Ser Phe Ile Asp Thr Tyr
225                 230                 235                 240

Ile Asp Leu Leu Glu Thr Arg Arg Thr Tyr Tyr Glu Gly Pro Gly Glu
                245                 250                 255

Gly Ser Pro Phe Gly Trp Lys Asp Ile Lys Glu Trp Tyr Glu Met Leu
            260                 265                 270

Met Gly His Cys Thr Tyr Phe Pro Glu Glu Leu Arg Ser Val Lys Tyr
        275                 280                 285

Ala Tyr Asn Ala Asp Leu Tyr Asn Ala Leu Asn Asp Leu Asn Asn Leu
    290                 295                 300

Val Ile Thr Arg Asp Glu Asn Glu Lys Leu Glu Tyr Tyr Glu Lys Phe
305                 310                 315                 320

Gln Ile Ile Glu Asn Val Phe Lys Gln Lys Lys Pro Thr Leu Lys
                325                 330                 335
```

-continued

```
Gln Ile Ala Lys Glu Ile Leu Val Asn Glu Asp Ile Lys Gly Tyr
                340                 345                 350
Arg Val Thr Ser Thr Gly Lys Pro Glu Phe Thr Asn Leu Lys Val Tyr
        355                 360                 365
His Asp Ile Lys Asp Ile Thr Ala Arg Lys Glu Ile Ile Glu Asn Ala
    370                 375                 380
Glu Leu Leu Asp Gln Ile Ala Lys Ile Leu Thr Ile Tyr Gln Ser Ser
385                 390                 395                 400
Glu Asp Ile Gln Glu Leu Thr Asn Leu Asn Ser Glu Leu Thr Gln
                405                 410                 415
Glu Glu Ile Glu Gln Ile Ser Asn Leu Lys Gly Tyr Thr Gly Thr His
                420                 425                 430
Asn Leu Ser Leu Lys Ala Ile Asn Leu Ile Leu Asp Glu Leu Trp His
            435                 440                 445
Thr Asn Asp Asn Gln Ile Ala Ile Phe Asn Arg Leu Lys Leu Val Pro
            450                 455                 460
Lys Lys Val Asp Leu Ser Gln Gln Lys Glu Ile Pro Thr Thr Leu Val
465                 470                 475                 480
Asp Asp Phe Ile Leu Ser Pro Val Val Lys Arg Ser Phe Ile Gln Ser
                485                 490                 495
Ile Lys Val Ile Asn Ala Ile Ile Lys Lys Tyr Gly Leu Pro Asn Asp
                500                 505                 510
Ile Ile Ile Glu Leu Ala Arg Glu Lys Asn Ser Lys Asp Ala Gln Lys
            515                 520                 525
Met Ile Asn Glu Met Gln Lys Arg Asn Arg Gln Thr Asn Glu Arg Ile
    530                 535                 540
Glu Glu Ile Ile Arg Thr Thr Gly Lys Glu Asn Ala Lys Tyr Leu Ile
545                 550                 555                 560
Glu Lys Ile Lys Leu His Asp Met Gln Glu Gly Lys Cys Leu Tyr Ser
                565                 570                 575
Leu Glu Ala Ile Pro Leu Glu Asp Leu Leu Asn Asn Pro Phe Asn Tyr
            580                 585                 590
Glu Val Asp His Ile Ile Pro Arg Ser Val Ser Phe Asp Asn Ser Phe
            595                 600                 605
Asn Asn Lys Val Leu Val Lys Gln Glu Glu Asn Ser Lys Lys Gly Asn
    610                 615                 620
Arg Thr Pro Phe Gln Tyr Leu Ser Ser Ser Asp Ser Lys Ile Ser Tyr
625                 630                 635                 640
Glu Thr Phe Lys Lys His Ile Leu Asn Leu Ala Lys Gly Lys Gly Arg
                645                 650                 655
Ile Ser Lys Thr Lys Lys Glu Tyr Leu Leu Glu Glu Arg Asp Ile Asn
            660                 665                 670
Arg Phe Ser Val Gln Lys Asp Phe Ile Asn Arg Asn Leu Val Asp Thr
    675                 680                 685
Arg Tyr Ala Thr Arg Gly Leu Met Asn Leu Leu Arg Ser Tyr Phe Arg
    690                 695                 700
Val Asn Asn Leu Asp Val Lys Val Lys Ser Ile Asn Gly Gly Phe Thr
705                 710                 715                 720
Ser Phe Leu Arg Arg Lys Trp Lys Phe Lys Lys Glu Arg Asn Lys Gly
                725                 730                 735
Tyr Lys His His Ala Glu Asp Ala Leu Ile Ile Ala Asn Ala Asp Phe
            740                 745                 750
```

Ile Phe Lys Glu Trp Lys Lys Leu Asp Lys Ala Lys Lys Val Met Glu
        755                 760                 765

Asn Gln Met Phe Glu Glu Lys Gln Ala Glu Ser Met Pro Glu Ile Glu
        770                 775                 780

Thr Glu Gln Glu Tyr Lys Glu Ile Phe Ile Thr Pro His Gln Ile Lys
785                 790                 795                 800

His Ile Lys Asp Phe Lys Asp Tyr Lys Tyr Ser His Arg Val Asp Lys
                805                 810                 815

Lys Pro Asn Arg Glu Leu Ile Asn Asp Thr Leu Tyr Ser Thr Arg Lys
                820                 825                 830

Asp Asp Lys Gly Asn Thr Leu Ile Val Asn Asn Leu Asn Gly Leu Tyr
                835                 840                 845

Asp Lys Asp Asn Asp Lys Leu Lys Lys Leu Ile Asn Lys Ser Pro Glu
        850                 855                 860

Lys Leu Leu Met Tyr His His Asp Pro Gln Thr Tyr Gln Lys Leu Lys
865                 870                 875                 880

Leu Ile Met Glu Gln Tyr Gly Asp Glu Lys Asn Pro Leu Tyr Lys Tyr
                885                 890                 895

Tyr Glu Glu Thr Gly Asn Tyr Leu Thr Lys Tyr Ser Lys Lys Asp Asn
        900                 905                 910

Gly Pro Val Ile Lys Lys Ile Lys Tyr Gly Asn Lys Leu Asn Ala
        915                 920                 925

His Leu Asp Ile Thr Asp Asp Tyr Pro Asn Ser Arg Asn Lys Val Val
930                 935                 940

Lys Leu Ser Leu Lys Pro Tyr Arg Phe Asp Val Tyr Leu Asp Asn Gly
945                 950                 955                 960

Val Tyr Lys Phe Val Thr Val Lys Asn Leu Asp Val Ile Lys Lys Glu
                965                 970                 975

Asn Tyr Tyr Glu Val Asn Ser Lys Cys Tyr Glu Glu Ala Lys Lys Leu
        980                 985                 990

Lys Lys Ile Ser Asn Gln Ala Glu Phe Ile Ala Ser Phe Tyr Asn Asn
        995                 1000                1005

Asp Leu Ile Lys Ile Asn Gly Glu Leu Tyr Arg Val Ile Gly Val
        1010                1015                1020

Asn Asn Asp Leu Leu Asn Arg Ile Glu Val Asn Met Ile Asp Ile
        1025                1030                1035

Thr Tyr Arg Glu Tyr Leu Glu Asn Met Asn Asp Lys Arg Pro Pro
        1040                1045                1050

Arg Ile Ile Lys Thr Ile Ala Ser Lys Thr Gln Ser Ile Lys Lys
        1055                1060                1065

Tyr Ser Thr Asp Ile Leu Gly Asn Leu Tyr Glu Val Lys Ser Lys
        1070                1075                1080

Lys His Pro Gln Ile Ile Lys Lys Gly Lys Arg Pro Ala Ala Thr
        1085                1090                1095

Lys Lys Ala Gly Gln Ala Lys Lys Lys Lys Gly Ser Tyr Pro Tyr
        1100                1105                1110

Asp Val Pro Asp Tyr Ala Tyr Pro Tyr Asp Val Pro Asp Tyr Ala
        1115                1120                1125

Tyr Pro Tyr Asp Val Pro Asp Tyr Ala
        1130                1135

<210> SEQ ID NO 26
<211> LENGTH: 3255

```
<212> TYPE: DNA
<213> ORGANISM: Artificial sequence
<220> FEATURE:
<223> OTHER INFORMATION: artificial saCas9 nucleotide sequence

<400> SEQUENCE: 26
atggccccaa agaagaagcg gaaggtcggt atccacggag tcccagcagc caagcggaac    60
tacatcctgg gcctggacat cggcatcacc agcgtgggct acggcatcat cgactacgag   120
acacgggacg tgatcgatgc cggcgtgcgg ctgttcaaag aggccaacgt ggaaacaac    180
gagggcaggc ggagcaagag aggcgccaga aggctgaagc ggcggaggcg catagaatc    240
cagagagtga agaagctgct gttcgactac aacctgctga ccgaccacag cgagctgagc   300
ggcatcaacc cctacgaggc cagagtgaag ggcctgagcc agaagctgag cgaggaagag   360
ttctctgccg ccctgctgca cctggccaag agaagaggcg tgcacaacgt gaacgaggtg   420
gaagaggaca ccggcaacga gctgtccacc aaagagcaga tcagccggaa cagcaaggcc   480
ctggaagaga atacgtggc cgaactgcag ctggaacggc tgaagaaaga cggcgaagtg    540
cggggcagca tcaacagatt caagaccagc gactacgtga agaagccaa acagctgctg    600
aaggtgcaga aggcctacca ccagctggac cagagcttca tcgacaccta catcgacctg   660
ctggaaaccc ggcggaccta ctatgaggga cctggcgagg gcagccct cggctggaag      720
gacatcaaag aatggtacga gatgctgatg ggccactgca cctacttccc cgaggaactg   780
cggagcgtga agtacgccta caacgccgac ctgtacaacg ccctgaacga cctgaacaat   840
ctcgtgatca ccagggacga gaacgagaag ctggaatatt acgagaagtt ccagatcatc   900
gagaacgtgt tcaagcagaa gaagaagccc accctgaagc agatcgccaa agaaatcctc   960
gtgaacgaag aggatattaa ggctacagag tgaccagca ccggcaagcc cgagttcacc    1020
aacctgaagg tgtaccacga catcaaggac attaccgccc ggaaagagat tattgagaac  1080
gccgagctgc tggatcagat tgccaagatc ctgaccatct accagagcag cgaggacatc  1140
caggaagaac tgaccaatct gaactccgag ctgacccagg aagagatcga gcagatctct  1200
aatctgaagg gctataccgg cacccacaac ctgagcctga aggccatcaa cctgatcctg  1260
gacgagctgt ggcacaccaa cgacaaccag atcgctatct tcaaccggct gaagctggtg  1320
cccaagaagg tggacctgtc ccagcagaaa gagatcccca ccaccctggt ggacgacttc  1380
atcctgagcc ccgtcgtgaa gagaagcttc atccagagca tcaaagtgat caacgccatc  1440
atcaagaagt acggcctgcc caacgacatc attatcgagc tggcccgcga gaagaactcc  1500
aaggacgccc agaaaatgat caacgagatg cagaagcgga accggcagac caacgagcgg  1560
atcgaggaaa tcatccggac caccggcaaa gaacgcca agtacctgat cgagaagatc  1620
aagctgcacg acatgcagga aggcaagtgc ctgtacagcc tggaagccat ccctctggaa  1680
gatctgctga caaccccctt caactatgag gtggaccaca tcatccccag aagcgtgtcc  1740
ttcgacaaca gcttcaacaa caaggtgctc gtgaagcagg aagaaacag caagaagggc  1800
aaccggaccc cattccagta cctgagcagc agcgacagca gatcagcta cgaaaccttc  1860
aagaagcaca tcctgaatct ggccaagggc aagggcagaa tcagcaagac caagaaagag  1920
tatctgctgg aagaacggga catcaacagg ttctccgtgc agaaagactt catcaaccgg  1980
aacctggtgg ataccagata cgccaccaga ggcctgatga acctgctgcg gagctacttc  2040
agagtgaaca acctggacgt gaaagtgaag tccatcaatg gcggcttcac cagctttctg  2100
cggcggaagt ggaagtttaa gaaagagcgg aacaagggg acaagcacca cgccgaggac  2160
```

```
gccctgatca ttgccaacgc cgatttcatc ttcaaagagt ggaagaaact ggacaaggcc    2220
aaaaaagtga tggaaaacca gatgttcgag gaaaagcagg ccgagagcat gcccgagatc    2280
gaaaccgagc aggagtacaa agagatcttc atcacccccc accagatcaa gcacattaag    2340
gacttcaagg actacaagta cagccaccgg gtggacaaga agcctaatag agagctgatt    2400
aacgacaccc tgtactccac ccggaaggac gacaagggca cacccctgat cgtgaacaat    2460
ctgaacggcc tgtacgacaa ggacaatgac aagctgaaaa agctgatcaa caagagcccc    2520
gaaaagctgc tgatgtacca ccacgacccc cagacctacc agaaactgaa gctgattatg    2580
gaacagtacg gcgacgagaa gaatcccctg tacaagtact acgaggaaac cgggaactac    2640
ctgaccaagt actccaaaaa ggacaacggc cccgtgatca agaagattaa gtattacggc    2700
aacaaactga cgcccatct ggacatcacc gacgactacc ccaacagcag aaacaaggtc    2760
gtgaagctgt ccctgaagcc ctacagattc gacgtgtacc tggacaatgg cgtgtacaag    2820
ttcgtgaccg tgaagaatct ggatgtgatc aaaaaagaaa actactacga agtgaatagc    2880
aagtgctatg aggaagctaa gaagctgaag aagatcagca ccaggccga gtttatcgcc    2940 tccttctaca caacgatct gatcaagatc aacggcgagc tgtatagagt gatcggcgtg    3000
aacaacgacc tgctgaaccg gatcgaagtg aacatgatcg acatcaccta ccgcgagtac    3060
ctggaaaaca tgaacgacaa gaggcccccc aggatcatta agacaatcgc ctccaagacc    3120
cagagcatta agagtacag cacagacatt ctgggcaacc tgtatgaagt gaaatctaag    3180
aagcaccctc agatcatcaa aaagggcaaa aggccggcgg ccacgaaaaa ggccggccag    3240
gcaaaaaaga aaaag                                                    3255

<210> SEQ ID NO 27
<211> LENGTH: 31
<212> TYPE: DNA
<213> ORGANISM: mus musculus

<400> SEQUENCE: 27
gtggccggca agagtcagta tcttctgggc g                                  31

<210> SEQ ID NO 28
<211> LENGTH: 31
<212> TYPE: DNA
<213> ORGANISM: Homo sapiens

<400> SEQUENCE: 28
gtgaccggca agagtcagta tcttctgggc g                                  31

<210> SEQ ID NO 29
<211> LENGTH: 1015
<212> TYPE: DNA
<213> ORGANISM: Artificial sequence
<220> FEATURE:
<223> OTHER INFORMATION: artificial mus musculus Mypt1 gene sequence
      with LoxP sites spanning exon 24

<400> SEQUENCE: 29
cttaaatata cctagtaaaa ttgaggtttg ctggagtatt gtttatcagt ccagacaaga    60
tttagataga tagatagata gatagataga tagatagata gatagataga tagatgtata    120
tacgtacgat aacttcgtat agcatacatt atacgaagtt attatatatg tatgtatgta    180
tgtgttttgt atatacacac acatatttta caaagttgta aggatcaaat atgaagctat    240
tttgctggtg ttttgagaag gacagtggtt tatgtgaatt tgtcattgtt atgttcttag    300
```

```
ctagaaggtc tttaataaag taacacatgc tctaaacaca ttgacattat aataagtgta    360
tgacattact aaatattaac attaattgtt aatctgggaa agaatgtcat tgagatagtt    420
tcagtgctgt taaactaaat gtaaatggtt tgtatctgaa aggtggccgg caagagtcag    480
tatcttctgg gcggtatgac ctgaccagtc ttacagttca tccatgactg ctgcttgctt    540
tcgcttaaca ctttacaaat gcttctcata aagggaaaa taaaacagga cactgcaata    600
atacattgtg tgttggcttt gcctgccact ctttgaaatg aattgaaaaa taaatgttgt    660
agttgctgtc ctatattcac cgcattaatg ctacacactg tatcaacctc tgactaaatc    720
tgtatagctg tagagtaaac tgaataacta actcacagta aacattgtga gcagaagaga    780
tgagtctctg agaataactt cgtatagcat acattatacg aagttataag ctttcgtttg    840
taagtgtaaa gcgcacatag tttaggcacg gttgcttctt gctcctctgc tcctgacact    900
gtagtataag tgcatctttg tgtgtgcgtg ttctttttcta tatagccttc agccttgata    960
ttggcttact ctatccctaa gtttatctga actagaaaga caaccatttg gatat        1015

<210> SEQ ID NO 30
<211> LENGTH: 540
<212> TYPE: DNA
<213> ORGANISM: Homo sapiens

<400> SEQUENCE: 30
tgtctataca ataatgttta ggcatgccga tgttggaata acatggtact taaaagacga    60
tcagtaggat tctgtctact ttttaaaatc atacaccta aaaacattaa catttacagt    120
aaatgtactg cttgactaaa tatcagcatt atttattaat ctgggaaaga gtgtcttgga    180
aatagtttca gtgtgattaa actaaattta aatggtttgt atctgaaagg tgaccggcaa    240
gagtcagtat cttctgggcg gtatgaccta accagttttta cagctcatca attactgctg    300
cttgcttttt gcataacacc ccagaatgct tatcatttaa gggagaataa aacagtacac    360
tgcaataatg tgttgtgtgt tggctttgcc tgtcactctt tgaaacaagt ttaaaataaa    420
cgctgcagtt gcttttctat tacattcact gcattaatgc tacacataat gtcaacctaa    480
atacaaagct ataagtcag ttggataaat aatggctagt acacattgtg agtggaggaa    540

<210> SEQ ID NO 31
<211> LENGTH: 24
<212> TYPE: DNA
<213> ORGANISM: Artificial sequence
<220> FEATURE:
<223> OTHER INFORMATION: oligonucleotide

<400> SEQUENCE: 31
caccgtatct gaaaggtgac cggc                                          24

<210> SEQ ID NO 32
<211> LENGTH: 24
<212> TYPE: DNA
<213> ORGANISM: Artificial sequence
<220> FEATURE:
<223> OTHER INFORMATION: oligonucleotide

<400> SEQUENCE: 32
aaacgccggt cacctttcag atac                                          24

<210> SEQ ID NO 33
<211> LENGTH: 25
<212> TYPE: DNA
<213> ORGANISM: Artificial sequence
```

```
<220> FEATURE:
<223> OTHER INFORMATION: oligonucleotide

<400> SEQUENCE: 33
caccgttatg tgtagcatta atgca                                         25

<210> SEQ ID NO 34
<211> LENGTH: 25
<212> TYPE: DNA
<213> ORGANISM: Artificial sequence
<220> FEATURE:
<223> OTHER INFORMATION: oligonucleotide

<400> SEQUENCE: 34
aaactgcatt aatgctacac ataac                                         25

<210> SEQ ID NO 35
<211> LENGTH: 25
<212> TYPE: DNA
<213> ORGANISM: Artificial sequence
<220> FEATURE:
<223> OTHER INFORMATION: oligonucleotide

<400> SEQUENCE: 35
caccgcatta tttattaatc tggga                                         25

<210> SEQ ID NO 36
<211> LENGTH: 25
<212> TYPE: DNA
<213> ORGANISM: Artificial sequence
<220> FEATURE:
<223> OTHER INFORMATION: oligonucleotide

<400> SEQUENCE: 36
aaactcccag attaataaat aatgc                                         25

<210> SEQ ID NO 37
<211> LENGTH: 25
<212> TYPE: DNA
<213> ORGANISM: Artificial sequence
<220> FEATURE:
<223> OTHER INFORMATION: oligonuceotide

<400> SEQUENCE: 37
caccgagaat gcttatcatt taagg                                         25

<210> SEQ ID NO 38
<211> LENGTH: 25
<212> TYPE: DNA
<213> ORGANISM: Artificial sequence
<220> FEATURE:
<223> OTHER INFORMATION: oligonucleotide

<400> SEQUENCE: 38
aaacccttaa atgataagca ttctc                                         25

<210> SEQ ID NO 39
<211> LENGTH: 25
<212> TYPE: DNA
<213> ORGANISM: Artificial sequence
<220> FEATURE:
<223> OTHER INFORMATION: oligonucleotide

<400> SEQUENCE: 39
caccgataca aagctataaa gtcag                                         25
```

```
<210> SEQ ID NO 40
<211> LENGTH: 25
<212> TYPE: DNA
<213> ORGANISM: Artificial sequence
<220> FEATURE:
<223> OTHER INFORMATION: oligonucleotide

<400> SEQUENCE: 40
aaacctgact ttatagcttt gtatc                                    25
```

COMPOSITIONS AND METHODS FOR GENETICALLY MODIFYING MYOSIN PHOSPHATASE TARGET SUBUNIT (MYPT1) GENE FOR LOWERING BLOOD PRESSURE

CROSS-REFERENCE TO RELATED APPLICATIONS

This application claims the benefit of U.S. Provisional Appl. No. 62/312,196, filed on Mar. 23, 2016, the contents of which are hereby incorporated by reference in their entirety.

STATEMENT OF FEDERALLY SPONSORED RESEARCH AND DEVELOPMENT

This invention was made with government support under the Grant Number HL066171 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 32,306 Byte ASCII (Text) file named "sequence_listing_ST25.txt," created on Mar. 22, 2017.

FIELD OF THE INVENTION

The invention relates to genetic modification and components for editing of a target nucleic acid sequence, and applications thereof in connection with lowering blood pressure.

BACKGROUND OF THE INVENTION

High blood pressure (hypertension) requiring medical therapy is prevalent particularly as people age, affecting about ⅓ to about ½ of the U.S. population and about 1 billion people and increasing worldwide. It is the leading risk factor, of 67 risk factors studied, for world-wide death and disability, including devastating strokes and heart and kidney failure. In the U.S. only about 50% of patients on drug therapies for hypertension achieve the traditional goal of 140/90 mm Hg, while the recently published SPRINT study (The Sprint Research Group, *N Engl J Med* 2015; 373:2103-2116) supports an even lower target of systolic BP of 120 mmHg. Patients fail to reach these BP targets for a number of reasons: often 3 or more medicines must be taken every day, and some multiple times each day. Compliance is often poor due to the number of medicines, dosing regimens and drug side effects. The cost of taking these and additional medicines each day for a lifetime may be prohibitive for the economically disadvantaged.

Myosin phosphatase (MP) is the primary mediator of smooth muscle relaxation and a key target of signaling pathways that regulate vessel tone (reviewed in (Dippold et al., *Microcirculation* 21: 239-248, 2014; Grassie et al., *ArchBiochemBiophys* 510: 147-159, 2011; Hartshorne et al., *J BiolChem* 279: 37211-37214, 2004). Nitric oxide (NO) signaling through the second messenger cGMP increases MP activity thereby decreasing force at any calcium concentration (Lee et al., *Journal of Biological Chemistry* 272: 5063-5068, 1997; Wu et al., *Biochem Biophys Res Comm* 220: 658-663, 1996), i.e. calcium de-sensitization of force production. While the exact mechanism by which NO/cGMP may activate MP has not been determined, in vitro and biochemical studies support a model in which the cGMP-dependent protein kinase (cGK1α) protein is targeted to the myosin phosphatase target subunit (Mypt1) via Leucine zipper motifs within coiled-coil domains present in the C-terminus of Mypt1 and N-terminus of cGK1 (Given et al., *AJP—Cell Physiology* 292: C432-C439, 2007; Huang et al., *J Biol Chem* 279: 597-603, 2004; Khatri et al., *J Biol Chem* 276: 37250-37257, 2001; Sharma et al., *Journal of Biological Chemistry* 283: 32860-32869, 2008; Surks et al., *Science* 286: 1583-1587, 1999).

Isoforms of Mypt1 are generated by alternative splicing of the 31 nt exon #24 (E24). Inclusion of E24 changes the reading frame and introduces a premature stop codon, thereby coding for a Mypt1 variant that lacks the C-terminal LZ motif (LZ−). The splicing of E24 and thus generation of Mypt1 LZ+/− isoforms is highly tissue-specific, developmentally regulated and modulated in disease (reviewed in Dippold et al., *Microcirculation* 21: 239-248, 2014; Reho et al., *Am J Physiol Heart Circ Physiol* 306: H163-172, 2014). A correlation has been shown between the relative expression of the Mypt1 E24−/LZ+ isoform and sensitivity to NO/cGMP-mediated calcium de-sensitization of force production, comparing phasic vs tonic smooth muscle (Khatri et al., *J Biol Chem* 276: 37250-37257, 2001; Payne et al., *J Mot Cell Cardiol* 40: 274-282, 2006), large vs small arteries (Payne et al., *Am J Physiol Heart Circ Physiol* 286: H1801-H1810, 2004; Reho et al., *Am J Physiol Heart Circ Physiol* 307: H563-573, 2014; Zheng et al., *Am J Physiol Cell Physiol* 308: C289-296, 2015), and in animal models of vascular disease in which expression of the Mypt1 E24/LZ isoforms is altered (Han et al., *J Vasc Res* 50: 100-108, 2013; Karim et al., *Circulation Research* 95: 612-618, 2004; Konik et al., *J Mot Cell Cardiol* 65: 147-155, 2013; Lu et al., *Am J Physiol Cell Physiol* 294: C564-0571, 2008; Ma et al., *AJP—Lung Cellular and Molecular Physiology* ajplung, 2010; Payne et al., *Am J Physiol Heart Circ Physiol* 286: H1801-H1810, 2004; Reho et al., *Am J Physiol Heart Circ Physiol* 308: H1039-1050, 2015; Zhang et al., *Circulation Research* 100: 730-737, 2007; Zhang et al., *JMCC* 47: 57-65, 2009). It has been appreciated since the discovery of NO as the endothelial-derived relaxing factor that smooth muscle tissues vary in their sensitivity to NO and cGMP-mediated relaxation (Diamond, *J PharmacolExpTher* 225: 422-426, 1983; Feletou et al., *Blood Vessels* 26: 21-32, 1989; Pannen et al., *Life Sciences* 62: 2025-2033, 1998; Pfitzer et al., *Pflugers Arch* 407: 87-91, 1986), yet mechanisms for this differential sensitivity remain poorly described.

CRISPRs (Clustered Regularly Interspaced Short Palindromic Repeats) evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complimentary to the viral genome, mediates targeting of a Cas9 protein to the sequence in the viral genome. The Cas9 protein cleaves and thereby silences the viral target.

Recently, the CRISPR/Cas system has been adapted for genome editing in eukaryotic cells. The introduction of site-specific double strand breaks (DSBs) allows for target sequence alteration through one of two endogenous DNA repair mechanisms—either non-homologous end-joining (NHEJ) or homology-directed repair (HDR).

There is a significant need to develop new therapeutics and methods for lowering blood pressure in patients. There is also a significant need to address problems associated with poor patient compliance, such as the number of medicines administered, dosing regimens and drug side effects.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

In one aspect, the invention provides a method of lowering blood pressure in a subject, comprising genetically modifying a myosin phosphatase target subunit (Mypt1) gene in a vascular smooth muscle cell of the subject, whereby the genetic modification of Mypt1 results in a deletion or inactivation of exon 24.

In one embodiment, exon 24 is deleted by a Cre-lox system, wherein the exon 24 is flanked by loxP sites, and the cell further comprises a gene encoding Cre recombinase.

In another embodiment, the method comprises administering to the cell a CRISPR/Cas system comprising: (a) a gRNA molecule comprising a targeting domain which is complementary with a target domain sequence of the Mypt1 gene and (b) a Cas9 molecule.

In another embodiment, the invention provides a vector comprising a CRISPR/Cas system for genetically modifying a Mypt1 gene, wherein the genetic modification of Mypt1 results in a deletion or inactivation of exon 24.

In one embodiment, the vector is a viral vector. In one embodiment, the virus is an adeno-associated virus (AAV). In another embodiment, the invention provides a host cell comprising the vector.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 11. An AAV targeting vector for genomic editing.

DETAILED DESCRIPTION OF THE INVENTION

Figure 1B:
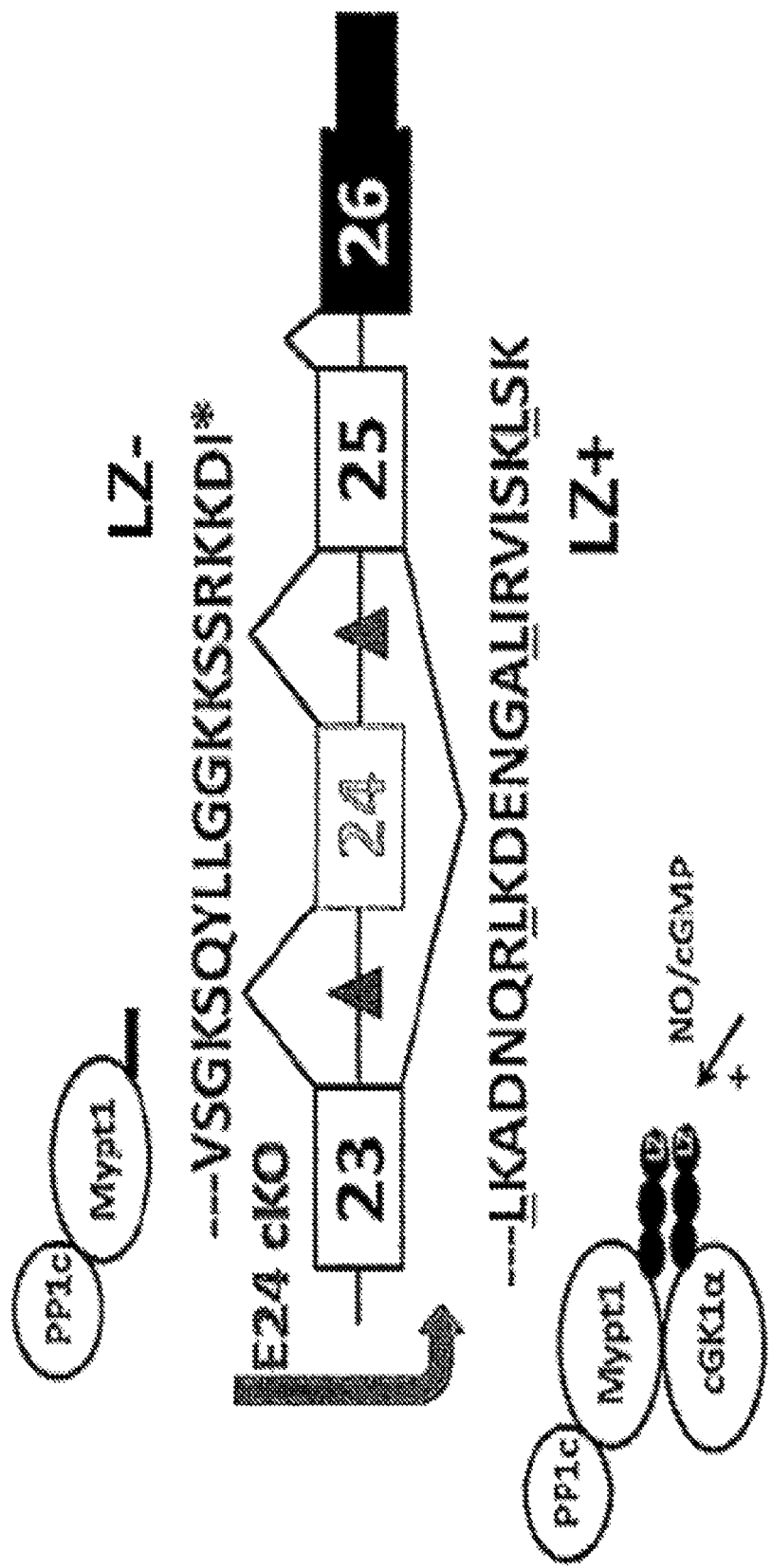
FIG. 1. Cre-Lox mediated deletion of Mypt1 Exon 24 in vascular smooth muscle. (A) Sequence of the Mouse Mypt1 gene including E24 and flanking introns. The highly conserved and putative splicing regulatory sequence is shaded. Exon sequence is bracketed and labeled "Ex24," and splice site sequence is grayed and adjacent to Ex24. Inserted LoxP sequences are labeled as such and underlined. (B) Schematic diagram of alternative splicing of Mypt1 E24. Skipping of E24 codes for the C-terminal leucine zipper (LZ) motif as shown that mediates hetero-dimerization with the N-terminal LZ motif in cGK1α. Inclusion of the 31 nt E24 changes the reading frame and codes for a unique C-terminal sequence, designated LZ−, and a premature termination codon. In the presence of Cre recombinase, intronic LoxP sites undergo recombination resulting in deletion of E24 (E24 cKO) (C) Total RNA was purified and reverse transcribed from the mesenteric arterial arcade (MA), aorta (Ao), portal vein (PV) and femoral artery (FA) of control (Cre+) and E24 cKO mice (heterozygotes: Cre+//F/+; homozygotes: Cre+//F/F). These experiments used the smooth muscle-specific and Tamoxifen-inducible smMHC-Cre.sup.ER. In all experiments mice were treated with Tamoxifen at age 3 weeks and studied as adults (age 8-12 weeks) as described in Methods. All mice in all experiments were Cre+ and treated with Tamoxifen, thus only the Mypt1 E24 genotype is shown in the graphs. PCR was performed on cDNAs using a single set of primers flanking E24 to amplify Mypt1 E24+ and E24− splice variants in a single reaction. PCR products were gel separated and quantified with a LI-COR imager and graphed as percent Mypt1 E24+ (LI-COR Biotechnology, Lincoln, Nebr.). (D) Protein lysates from mouse mesenteric arterial arcade were subjected to Western blot analysis. Membranes were probed with rabbit polyclonal antibodies specific for the LZ− and LZ+ isoforms of Mypt1 (.about.130 kDa) and then stripped and re-probed with an antibody that recognizes all Mypt1 isoforms. The LZ+ antibody also recognizes the LZ motif present in the Mypt1 family member p85. The ratio of Mypt1 LZ−/LZ+ for mice of the different genotypes is plotted, normalized to the control value (n=3 each) *, † $p<0.05$ vs control.

The invention is based on the surprising discovery that blood pressure can be lowered in a subject by deleting or inactivating exon 24 of a myosin phosphatase target subunit (Mypt1).

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, e.g., Sambrook et al. *Molecular Cloning: A Laboratory Manual*, $2^{nd}$ edition (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR 2: A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "a cell" includes a plurality of cells, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of".

As used herein, the term "about" means plus or minus 10% of the numerical value of the number with which it is being used.

The terms "nucleic acid," and "polynucleotide," are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids. The term "sequence" relates to a nucleotide sequence of any length, which can be DNA or RNA; can be linear, circular or branched and can be either single-stranded or double stranded.

The term "identity" relates to an exact nucleotide-to-nucleotide or amino acid-to-amino acid correspondence of two polynucleotides or polypeptide sequences, respectively. Two or more sequences (polynucleotide or amino acid) can be compared by determining their percent identity. Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

"Sequence similarity" between polynucleotides can be determined by hybridization of polynucleotides under conditions that allow formation of stable duplexes between homologous regions, followed by digestion with single-stranded-specific nuclease(s), and size determination of the digested fragments.

In one embodiment, the invention provides a method of lowering blood pressure in a subject, comprising genetically modifying a myosin phosphatase target subunit (Mypt1) gene in a vascular smooth muscle cell of the subject, whereby the genetic modification of Mypt1 results in a deletion or inactivation of exon 24.

"Subject," as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In one embodiment, the subject is a human. In some embodiments, the subject is a mouse.

Isoforms of the myosin phosphatase regulatory subunit (Mypt1) are generated by alternative splicing of a 31 nucleotide exon 24. In some embodiments, the Mypt1 exon 24 is deleted or inactivated from a mammalian subject. Mouse exon 24 sequence is shown in FIGS. 1A and 1s represented by SEQ ID NO:27. In some embodiments, exon 24 is deleted or inactivated in a human subject. In some embodiments, human exon 24 is represented by SEQ ID NO:28.

The genetic modification of Mypt1 is not limiting. In some embodiments, exon 24 is deleted or inactivated by a Cre-lox system, wherein exon 24 is flanked by loxP sites, and the cell further comprises a gene encoding Cre recombinase. In some embodiments, expression of Cre recombinase can be controlled by providing the subject with an inducer. In some embodiments, the inducer is an effective amount of Tamoxifen.

In some embodiments, only one allele of Mypt1 is genetically modified in the cell to delete or inactivate exon 24. In some embodiments, two alleles of Mypt1 are genetically modified in the cell. Without being bound by theory, it is believed that deletion or inactivation of exon 24 renders Mypt1 sensitive to nitric oxide in the vascular smooth muscle cell, thereby lowering blood pressure.

In some embodiments, the subject has a systolic blood pressure prior to treatment of at least 140 mm Hg. In some embodiments, the subject has a systolic blood pressure prior to treatment of at least 160 mm Hg. In some embodiments, the subject has a diastolic blood pressure prior to treatment of at least 90 mm Hg. In some embodiments, the subject has a diastolic blood pressure prior to treatment of at least 100 mm Hg. In some embodiments, the subject has a systolic blood pressure prior to treatment of at least 160 mm Hg and a diastolic blood pressure of at least 100 mm Hg. In some embodiments, the subject's systolic blood pressure can be lowered by at least about 5 mm Hg, by at least about 10 mm Hg, by at least about 15 mm Hg, by at least about 20 mm Hg, by at least about 25 mm Hg, by at least about 30 mm Hg, by at least about 35 mm Hg, by at least about 40 mm Hg, by at least about 45 mm Hg, or by at least about 50 mm Hg. In some embodiments, the subject's diastolic blood pressure can be lowered by at least about 2 mm Hg, by at least about 5 mm Hg, by at least about 10 mm Hg, by at least about 15 mm Hg, by at least about 20 mm Hg, by at least about 25 mm Hg, by at least about 30 mm Hg, by at least about 35 mm Hg, or by at least about 40 mm Hg.

In some embodiments, the genetic modification of Mypt1 comprises a genomic editing approach. "Genomic editing" of an animal gene can be achieved, for example, by a single cleavage event, by cleavage followed by non-homologous end joining, by cleavage followed by homology-directed repair mechanisms, by cleavage followed by physical integration of a donor sequence, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript. See, U.S. Patent Publication Nos. 20030232410; 20050208489; 20050026157; 20050064474; 20060188987; 20060063231; and International Publication WO 07/014,275, the disclosures of which are incorporated by reference in their entireties for all purposes.

For example, genomic editing can be performed using a nuclease, including CRISPR associated proteins (Cas proteins, e.g., Cas9), Zinc finger nuclease (ZFN), Transcription Activator-Like Effector Nuclease (TALEN), and meganucleases. Nucleases can be naturally existing nucleases, genetically modified, and/or recombinant. Gene editing can also be performed using a transposon-based system (e.g. PiggyBac, Sleeping beauty). For example, gene editing can be performed using a transposase.

In some embodiments, exon 24 of a subject, such as a human, is deleted or inactivated using a CRISPR/Cas system of genomic editing. In some embodiments of the disclosure, one or more targeted "nucleases," e.g. CRISPR/Cas9, TALEN or ZFN, as described herein create a double-stranded break in the target sequence (e.g., cellular chromatin) at a predetermined site. A "target site" or "target sequence" is a nucleic acid sequence that defines a general region of a nucleic acid to which a binding molecule may bind, provided sufficient conditions for binding exist.

In some embodiments, the region on human Mypt1 targeted for genomic editing is from 155881 bp to 156420 bp (SEQ ID NO:30) of the human Mypt1 gene (PPP1R12A) (gene sequence ID ENSG00000058272). This region corresponds to a 540 bp-long region containing exon 24 and flanking intronic sequence for gRNA targets.

In some embodiments, the method comprises administering to the cell a CRISPR/Cas system comprising: (a) a gRNA molecule comprising a targeting domain which is complementary with a target domain sequence of the Mypt1 gene and (b) a Cas9 molecule, wherein the CRISPR/Cas system is capable of deleting or inactivating exon 24 of the Mypt1 gene.

In some embodiments, the method comprises administering a nucleic acid composition that comprises: (a) a first nucleotide sequence encoding the gRNA molecule and (b) a second nucleotide sequence encoding the Cas9 molecule.

In some embodiments, the invention provides a nucleic acid encoding a gRNA that is compatible for use with a Cas9 molecule, wherein the gRNA comprises a targeting domain which is complementary with a target domain sequence of the Mypt1 gene A gRNA molecule, as that term is used herein, refers to a nucleic acid that promotes the specific targeting or homing of a gRNA molecule/Cas9 molecule complex to a target nucleic acid. As set forth herein, the target nucleic acid is a myosin phosphatase target subunit (Mypt1) gene, specifically, a Mypt1 gene in vascular smooth muscle cells. The gRNA molecule/Cas9 molecule complex effects a genetic modification of Mypt1 and results in deletion or inactivation of exon 24, thereby lowering blood pressure in the subject.

The gRNA molecule can be unimolecular (having a single RNA molecule), sometimes referred to herein as "chimeric" gRNAs, or modular (comprising more than one, and typically two, separate RNA molecules). In one embodiment, the gRNA molecule can be used with a Cas9 protein from *Staphylococcus aureus*.

The gRNA comprises a targeting domain (which is complementary to the target nucleic acid) and other sequences that are necessary to bind Cas9. The targeting domain comprises a nucleotide sequence that is complementary, e.g., at least 80, 85, 90, or 95% complementary, e.g., fully complementary, to the target sequence on the target nucleic acid. The targeting domain is part of an RNA molecule and will therefore comprise the base uracil (U), while any DNA encoding the gRNA molecule will comprise the base thymine (T). While not wishing to be bound by theory, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence. In an embodiment, the target domain itself comprises, in the 5' to 3' direction, an optional secondary domain, and a core domain. In an embodiment, the core domain is fully complementary with the target sequence. In an embodiment, the targeting domain is 5 to 50, 10 to 40, e.g., 10 to 30, e.g., 15 to 30, e.g., 15 to 25 nucleotides in length. In an embodiment, the targeting domain is 15, 16, 17, 18, 19, 20, 21, 22, 23, 24 or 25 nucleotides in length. The strand of the target nucleic acid with which the targeting domain is complementary is referred to herein as the complementary strand. Some or all of the nucleotides of the domain can have a modification, e.g., a modification described herein. Guidance on the selection of targeting domains can be found, e.g., in Fu et al., *Nat Biotechnol* 2014 (doi: 10.1038/nbt.2808) and Sternberg S H et al., Nature 2014 (doi: 10.1038/nature13011).

The gRNA comprises a targeting domain that effects a genetic modification of Mypt1 and results in a deletion or inactivation of exon 24. In some embodiments, the gRNA comprises a targeting domain and SEQ ID NO:18, which enables the gRNA to be compatible with a Cas9 protein from *Staphylococcus aureus*.

In some embodiments, the gRNA comprises a targeting domain which is complementary with a target domain sequence which comprises any one or a combination of SEQ ID NO:1; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; and SEQ ID NO:17.

In some embodiments, the gRNA is selected from any one or a combination of SEQ ID NO:19-23.

In some embodiments, the targeting domain is 10 to 100, 10 to 90, 10 to 80, 10 to 70, 10 to 60, 10 to 50, 10 to 40, 10 to 30, 10 to 20 or 10 to 15 nucleotides in length. In other embodiments, the targeting domain is 20 to 100, 20 to 90, 20 to 80, 20 to 70, 20 to 60, 20 to 50, 20 to 40, 20 to 30, or 20 to 25 nucleotides in length. In some embodiments, the targeting domain is 16, 17, 18, 19, 20, 21, 22, 23, 24 or 25 nucleotides in length.

In some embodiments, the targeting domain has full complementarity with the target sequence. In some embodiments, the targeting domain has or includes 1, 2, 3, 4, 5, 6, 7 or 8 nucleotides that are not complementary with the corresponding nucleotide of the targeting domain.

In some embodiments, the target domain includes 1, 2, 3, 4 or 5 nucleotides that are complementary with the corresponding nucleotide of the targeting domain within 5 nucleotides of its 5' end. In an embodiment, the target domain includes 1, 2, 3, 4 or 5 nucleotides that are complementary with the corresponding nucleotide of the targeting domain within 5 nucleotides of its 3' end.

In some embodiments, the target domain includes 1, 2, 3, or 4 nucleotides that are not complementary with the corresponding nucleotide of the targeting domain within 5 nucleotides of its 5' end. In some embodiments, the target domain includes 1, 2, 3, or 4 nucleotides that are not complementary with the corresponding nucleotide of the targeting domain within 5 nucleotides of its 3' end.

In some embodiments, the degree of complementarity, together with other properties of the gRNA, is sufficient to allow targeting of a Cas9 molecule to the targeted region of Mypt1.

In some embodiments, the targeting domain comprises two consecutive nucleotides that are not complementary to the target domain ("non-complementary nucleotides"), e.g., two consecutive noncomplementary nucleotides that are within 5 nucleotides of the 5' end of the targeting domain, within 5 nucleotides of the 3' end of the targeting domain, or more than 5 nucleotides away from one or both ends of the targeting domain.

In some embodiments, no two consecutive nucleotides within 5 nucleotides of the 5' end of the targeting domain, within 5 nucleotides of the 3' end of the targeting domain, or within a region that is more than 5 nucleotides away from one or both ends of the targeting domain, are not complementary to the targeting domain.

In some embodiments, there are no noncomplementary nucleotides within 5 nucleotides of the 5' end of the targeting domain, within 5 nucleotides of the 3' end of the targeting domain, or within a region that is more than 5' nucleotides away from one or both ends of the targeting domain.

In some embodiments, the targeting domain comprises one or more modifications, e.g., modifications that render it less susceptible to degradation or more bio-compatible, e.g., less immunogenic. By way of example, the backbone of the targeting domain can be modified with a phosphorothioate. In one embodiment, a nucleotide of the targeting domain can comprise a 2' modification (e.g., a modification at the 2' position on ribose), e.g., a 2' acetylation, e.g., a 2' methylation, or other modification.

Methods for designing gRNAs are described herein, including methods for selecting, designing and validating target domains. Targeting domains discussed herein can be incorporated into the gRNAs described herein. Methods for selection and validation of target sequences as well as off-target analyses are described, e.g., Mali et al., 2013 *Science* 339(6121): 823-826; Hsu et al., 2013 *Nat Biotechnol*, 31(9): 827-32; Fu et al., 2014 *Nat Biotechnol*, doi: 10.1038/nbt.2808. PubMed PMID: 24463574; Heigwer et al., 2014 *Nat Methods* 11(2):122-3. doi: 10.1038/nmeth.2812. PubMed PMID: 24481216; Bae et al., 2014 *Bioinformatics* PubMed PMID: 24463181; Xiao A et al., 2014 *Bioinformatics* PubMed PMID: 24389662.

For example, a software tool can be used to optimize the choice of gRNA within a user's target sequence, e.g., to minimize total off-target activity across the genome. Off target activity may be other than cleavage. For each possible gRNA choice, e.g., using *S. pyogenes* Cas9, the tool can identify all off-target sequences (e.g., preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted using an experimentally-derived weighting scheme. Each possible gRNA is then ranked according to its total predicted off-target cleavage; the top-ranked gRNAs represent those that are likely to have the greatest on-target and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate gRNA molecules can be evaluated by art-known methods.

Cas Molecules

Cas molecules of a variety of species can be used in the methods and compositions described herein. In some embodiments, the molecule is Cas9. In some embodiments, the Cas9 is from *Staphylococcus aureus*. In some embodiments, the Cas9 is from *S. pyogenes*, *S. thermophiles*, or *Neisseria meningitides*. Additional Cas9 species include: *Acidovorax avenae, Actinobacillus pleuropneumonias. Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum,* gamma proteobacterium, *Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis. Streptococcus* sp., *Subdoligranulum* sp., *Tistrella mobilis, Treponema* sp., or *Verminephmrobacter eiseniae*.

A Cas9 molecule, as that term is used herein, refers to a molecule that can interact with a gRNA molecule and, in concert with the gRNA molecule, localize (e.g., target or home) to a site which comprises a target domain and PAM sequence.

The Cas9 molecule is capable of cleaving a target nucleic acid molecule. The ability of a Cas9 molecule to interact with and cleave a target nucleic acid is PAM sequence dependent. A PAM sequence is a sequence in the target nucleic acid. In an embodiment, cleavage of the target nucleic acid occurs upstream from the PAM sequence. Cas9 molecules from different bacterial species can recognize different sequence motifs (e.g., PAM sequences). In some embodiments, a Cas9 molecule of *S. pyogenes* recognizes the sequence motif NGG and directs cleavage of a target nucleic acid sequence 1 to 10, e.g., 3 to 5, base pairs upstream from that sequence. See, e.g., Mali et al., *Science* 2013; 339(6121): 823-826. In some embodiments, a Cas9 molecule of *S. thermophilus* recognizes the sequence motif NGGNG and NNAGAAW (W=A or T) and directs cleavage of a core target nucleic acid sequence 1 to 10, e.g., 3 to 5, base pairs upstream from these sequences. See, e.g., Horvath et al., *Science* 2010; 327(5962):167-170, and Deveau et al., *J Bacteriol* 2008; 190(4): 1390-1400. In some embodiments, a Cas9 molecule of *S. mutans* recognizes the sequence motif NGG or NAAR (R=A or G) and directs cleavage of a core target nucleic acid sequence 1 to 10, e.g., 3 to 5 base pairs, upstream from this sequence. See, e.g., Deveau et al., *J Bacteriol* 2008; 190(4): 1390-1400. In some embodiments, a Cas9 molecule of *S. aureus* recognizes the sequence motif NNGRRT (R=A or G) and directs cleavage of a target nucleic acid sequence 1 to 10, e.g., 3 to 5, base pairs upstream from that sequence. In some embodiments, a Cas9 molecule of *N. meningitidis* recognizes the sequence motif NNNNGATT and directs cleavage of a target nucleic acid sequence 1 to 10, e.g., 3 to 5, base pairs upstream from that sequence. See, e.g., Hou et al., *PNAS Early Edition* 2013, 1-6. The ability of a Cas9 molecule to recognize a PAM sequence can be determined, e.g., using a transformation assay described in Jinek et al., *Science* 2012, 337:816.

Exemplary naturally occurring Cas9 molecules are described in Chylinski et al., *RNA Biology* 2013; 10:5, 727-737, which is incorporated herein by reference. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. pyogenes* (e.g., strain SF370, MGAS10270, MGAS10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. anginosus* (e.g.; strain F0211), *S. agalactiae* (e.g., strain NEM316, A909), *Listeria monocytogenes* (e.g., strain F6854), *Listeria innocua* (*L. innocua*, e.g., strain Clip11262) *Enterococcus italicus* (e.g., strain DSM 15952), or *Enterococcus faecium* (e.g., strain 1,231,408). Additional exemplary Cas9 molecules are a Cas9 molecule of *Neisseria meningitidis* (Hou et al. *PNAS Early Edition* 2013, 1-6) and a *S. aureus* Cas9 molecule.

In one embodiment, the Cas9 molecule is from *Staphylococcus aureus*. In some embodiments, *Staphylococcus aureus* Cas9 has the amino acid sequence of SEQ ID NO:24 (Accession No.: J7RUA5). In some embodiments, a *Staphylococcus aureus* Cas9 is modified with a nuclear localization signal. In some embodiments, the *Staphylococcus aureus* Cas9 modified with a nuclear localization signal has the sequence of SEQ ID NO:25. In some embodiments, the nucleotide sequence of modified *Staphylococcus aureus* Cas9 is SEQ ID NO:26.

In some embodiments, the nucleic acid sequence of Cas9 contains a nucleotide sequence that is highly identical, at least 90% identical, with a nucleotide sequence encoding Cas9 polypeptide. In some embodiments, the nucleic acid sequence of Cas9 comprises a nucleotide sequence that is at least 60%, 65%, 70%, 75%, 80%, 85%, 90%, 91%, 92%, 93%, 94%, 95%, 96%, 97%, 98% 99% or 100% identical with the encoding nucleotide sequence set forth in SEQ ID NO:26.

When a Cas9 polynucleotide is used for the production of Cas9 polypeptide, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, nuclear localization signal or other fusion peptide portions. The polynucleotide may also contain non-coding 5' and 3' sequences, such as transcribed, non-translated sequences, splicing and polyadenylation signals, ribosome binding sites and sequences that stabilize mRNA.

In some embodiments, the nucleotide sequence encoding Cas9 or a biologically active fragment or derivative thereof includes nucleic acid molecules comprising a polynucleotide having a nucleotide sequence at least 90%, 91%, 92%, 93%, 94%, 95%, 96%, 97%, 98% 99% or 100% identical to (a) a nucleotide sequence encoding Cas9 having the amino acid sequence in SEQ ID NO:24 or 25; or (b) a nucleotide sequence complementary to the nucleotide sequences in (a).

In some embodiments, the nucleotide sequences are at least 90% identical over their entire length to a polynucleotide encoding a Cas9 having the amino acid sequence set out in SEQ ID NO:24 or 25, and polynucleotides which are complementary to such polynucleotides. In some embodiments, the polynucleotides are at least 91%, 92%, 93%, 94%, 95%, 96%, 97%, 98%, or at least 99% identical. In some embodiments, the nucleic acid molecule encodes a biologically active fragment of Cas9 protein.

In some embodiments, a Cas9 molecule comprises an amino acid sequence having at least 60%, 65%, 70%, 75%, 80%, 85%, 90%, 95%, 96%, 97%, 98%, or 99% homology with SEQ ID NO:24 or 25 or a naturally occurring Cas9 molecule sequence, e.g., a Cas9 molecule from a species listed herein or described in Chylinski et al., *RNA Biology* 2013, 10:5, 727-737; Hou et al. *PNAS Early Edition* 2013, 1-6.

In some embodiments, the Cas9 protein comprises an amino acid sequence that differs from a sequence of SEQ ID NO: 24 or 25 by as many as 1, but no more than 2, 3, 4, or 5 residues.

Naturally occurring Cas9 molecules possess a number of properties, including: nickase activity, nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In some embodiments, a Cas9 molecule can include all or a subset of these properties. In typical embodiments, Cas9 molecules have the ability to interact with a gRNA molecule and, in concert with the gRNA molecule, localize to a site in a nucleic acid. Other activities, e.g., PAM specificity, cleavage activity, or helicase activity can vary more widely in Cas9 molecules.

Cas9 molecules with desired properties can be made in a number of ways, e.g., by alteration of a parental, naturally occurring Cas9 molecule to provide an altered Cas9 molecule having a desired property. One or more mutations or differences relative to a parental Cas9 molecule can be introduced. Such mutations and differences can comprise: substitutions (e.g., conservative substitutions or substitutions of non-essential amino acids); insertions; or deletions. In some embodiments, a Cas9 molecule can comprises one or more mutations or differences, e.g., at least 1, 2, 3, 4, 5, 10, 15, 20, 30, 40 or 50 mutations but less than 200, 100, or 80 mutations relative to a reference Cas9 molecule.

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule are described, e.g., in Jinek et al., Science 2012; 337(6096):816-821.

In some embodiments, the genomic editing of Mypt1 can be by homology-directed repair (HDR). In some embodiments, HDR comprises a Cas9 molecule/gRNA molecule complex and a template nucleic acid.

In some embodiments, the genomic editing of Mypt1 can be by nuclease-induced non-homologous end-joining (NHEJ). Nuclease-induced NHEJ can be used to remove (e.g., delete) sequence in a gene of interest. While not wishing to be bound by theory, it is believed that, in some embodiments, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair.

In some embodiments, NHEJ can be used to delete small sequence motifs. If a double-strand break is targeted near to a short target sequence, the deletion mutations caused by the NHEJ repair often span, and therefore remove, the unwanted nucleotides. It is also possible to introduce two double-strand breaks, one on each side of the sequence, can result in NHEJ between the ends with removal of the entire intervening sequence. Both of these approaches can be used to delete specific DNA sequences. In some embodiments, exon 24 is deleted or inactivated by NHEJ, wherein a pair of gRNAs are employed to introduce two double-strand breaks, one on each side of the exon 24 sequence, resulting in deletion of exon 24. In some embodiments, the pair of gRNAs disrupt the exon 24 splice site, resulting in transcripts that lack exon 24. In some embodiments, a single gRNA is employed resulting in either deletion or inactivation of exon 24.

In some embodiments, the method utilizes a pair of gRNAs. In some embodiments, the pair of gRNAs comprise a targeting domain which is complementary with a target domain sequence comprising SEQ ID NO:10 and SEQ ID NO:15; SEQ ID NO:10 and SEQ ID NO:13; SEQ ID NO:10 and SEQ ID NO:16; SEQ ID NO:9 and SEQ ID NO:15; SEQ ID NO:9 and SEQ ID NO:13; or SEQ ID NO:9 and SEQ ID NO:16.

In some embodiments, the pair of gRNAs comprises SEQ ID NO:19 and SEQ ID NO:20; SEQ ID NO:19 and SEQ ID NO:22; SEQ ID NO:19 and SEQ ID NO:23; SEQ ID NO:21 and SEQ ID NO:20; SEQ ID NO:21 and SEQ ID NO:22; and SEQ ID NO:22 and SEQ ID NO:23.

In one embodiment, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In one embodiment, the cleavage site is between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In some embodiments, the methods of the present invention are combined with one or more other known treatments for lowering blood pressure. In some embodiments, the method is combined with administration of a diuretic (e.g., furosemide, hydrochlorothiazide, and spironolactone), beta-blocker (e.g., propranolol, metoprolol, and atenolol), alpha-blocker (e.g., doxazosin, prazosin, and terazosin), alpha/beta blocker (e.g., labetalol and carvedilol), centrally acting sympatholytic (e.g., methyldopa), peripherally acting sympatholytic (e.g., reserpine), calcium-channel blocker (e.g., nifedipine, verapamil, and diltiazem), dihydropyridine (e.g., amlodipine), direct vasodilator (e.g., hydralazine and minoxidil), angiotensin-converting enzyme (ACE) inhibitor (e.g., enalapril, captopril, lisinopril, and benazepril), and combinations thereof.

In some embodiments, the method results in a decreased incidence or probability of heart disease in the subject. In some embodiments, the method results in a decreased incidence or probability of a heart attack in the subject. In some embodiments, the method results in a decreased incidence or probability of a stroke or other adverse vascular event in the subject.

Vectors and Host Cells

The present invention also relates to vectors that comprise the CRISPR/Cas9 system of the present invention, and host cells which are genetically engineered with vectors of the invention and the production of polypeptides and nucleic acids of the invention by recombinant techniques. Cell-free translation systems can also be employed to produce such proteins using RNAs derived from the constructs of the invention.

Representative examples of appropriate hosts include bacterial cells, such as streptococci, staphylococci, *E. coli*, *Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, and 293 cells; and plant cells. A great variety of expression systems can be used, including DNA or RNA vectors.

The components for genetically modifying the cell can be delivered, formulated, or administered in a variety of forms. When a component is delivered encoded in nucleic acid the nucleic acid will typically include a control region, e.g., comprising a promoter, to effect expression. In some embodiments, useful promoters for Cas9 molecule sequences include CMV, EF-1a, MSCV, PGK, CAG control promoters. In some embodiments, useful promoters for gRNAs include H1, EF-1a and U6 promoters. Promoters with similar or dissimilar strengths can be selected to tune the expression of components. Sequences encoding a Cas9 molecule can comprise a nuclear localization signal (NLS), e.g., an SV40 NLS. In some embodiments, a promoter for a Cas9 molecule or a gRNA molecule can be, independently, inducible, tissue specific, or cell specific.

Nucleic acid encoding Cas9 and/or gRNA molecules can be administered to subjects or delivered into cells by art-known methods or as described herein. For example, Cas9-encoding and/or gRNA-encoding DNA can be delivered by vectors (e.g., viral or non-viral vectors), non-vector based methods (e.g., using naked DNA or DNA complexes), or a combination thereof.

In some embodiments, the Cas9 and one or more gRNAs are located on a single nucleic acid molecule. In some embodiments, the Cas9 and one or more gRNAs are located on separate nucleic acid molecules. In some embodiments, wherein multiple gRNAs are utilized, the Cas9 and one or more gRNAs are located on a single nucleic acid molecule and one or more additional gRNAs are located a different nucleic acid molecule.

In some embodiments, the Cas9- and/or gRNA-encoding nucleic acid is delivered by a vector such as a viral vector/virus or plasmid. In some embodiments, a vector can comprise a sequence that encodes a Cas9 molecule and/or a gRNA molecule. In some embodiments, a vector can also comprise a sequence encoding a signal peptide (e.g., for nuclear localization, nucleolar localization, mitochondrial localization), fused, e.g., to a Cas9 molecule sequence. For example, a vector can comprise a nuclear localization sequence (e.g., from SV40) fused to the sequence encoding the Cas9 molecule.

In some embodiments, one or more regulatory/control elements, e.g., a promoter, an enhancer, an intron, a polyadenylation signal, a Kozak consensus sequence, internal ribosome entry sites (IRES), a 2A sequence, and a splice acceptor or donor can be included in the vectors. In some embodiments, the promoter is recognized by RNA polymerase II (e.g., a CMV promoter). In other embodiments, the promoter is recognized by RNA polymerase III (e.g., a U6 promoter). In some embodiments, the promoter is a regulated promoter (e.g., inducible promoter). In other embodiments, the promoter is a constitutive promoter. In some embodiments, the promoter is a tissue specific promoter. In some embodiments, the promoter is a viral promoter. In other embodiments, the promoter is a non-viral promoter.

In some embodiments, the vector or delivery vehicle is a viral vector (e.g., for generation of recombinant viruses). In some embodiments, the virus is a DNA virus (e.g., dsDNA or ssDNA virus). In other embodiments, the virus is an RNA virus (e.g., an ssRNA virus). Exemplary viral vectors/viruses include retroviruses, lentiviruses, adenovirus, adeno-associated virus (AAV), vaccinia viruses, poxviruses, and herpes simplex viruses.

In some embodiments, the virus infects dividing cells. In other embodiments, the virus infects non-dividing cells. In some embodiments, the virus infects both dividing and non-dividing cells. In some embodiments, the virus can integrate into the host genome. In some embodiments, the virus is engineered to have reduced immunity, e.g., in humans. In some embodiments, the virus is replication-competent. In other embodiments, the virus is replication-defective, e.g., having one or more coding regions for the genes necessary for additional rounds of virion replication and/or packaging replaced with other genes or deleted. In some embodiments, the virus causes transient expression of the Cas9 molecule and/or the gRNA molecule. In other embodiments, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In some embodiments, the Cas9- and/or gRNA-encoding nucleic is delivered by a recombinant retrovirus. In some embodiments, the retrovirus (e.g., Moloney murine leukemia virus) comprises a reverse transcriptase, e.g., that allows integration into the host genome. In some embodiments, the retrovirus is replication-competent. In other embodiments, the retrovirus is replication-defective, e.g., having one of more coding regions for the genes necessary for additional rounds of virion replication and packaging replaced with other genes, or deleted.

In some embodiments, the Cas9- and/or gRNA-encoding nucleic acid is delivered by a recombinant lentivirus. In some embodiments, the lentivirus is replication-defective and does not comprise one or more genes required for viral replication.

In some embodiments, the Cas9- and/or gRNA-encoding nucleic acid is delivered by a recombinant adenovirus. In some embodiments, the adenovirus is engineered to have reduced immunity in human.

In some embodiments, the Cas9- and/or gRNA-encoding nucleic acid is delivered by a recombinant AAV. In some embodiments, the AAV can incorporate its genome into that of a host cell, e.g., a vascular smooth muscle cell. In some embodiments, the AAV is a self-complementary adeno-associated virus (scAAV), e.g., a scAAV that packages both strands which anneal together to form double stranded DNA. AAV serotypes that can be used in the methods of the invention include, e.g., AAV1, AAV2, modified AAV2 (e.g., modifications at Y444F, Y500F, Y730F and/or S662V), AAV3, modified AAV3 (e.g., modifications at Y705F, Y731 F and/or T492V), AAV4, AAV5, AAV6, modified AAV6 (e.g., modifications at S663V and/or T492V), AAV8, AAV 8.2, AAV9, AAV rh 10, and pseudotyped AAV, such as AAV2/8, AAV2/5 and AAV2/6 can also be used in the disclosed methods.

In some embodiments, the Cas9- and/or gRNA-encoding nucleic acid is delivered by a hybrid virus, e.g., a hybrid of one or more of the viruses described herein.

In some embodiments, a packaging cell can be used to form a virus particle that is capable of infecting a host or target cell. Such a cell can include a 293 cell, which can package adenovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed. For example, an AAV vector used in gene therapy typically only possesses inverted terminal repeat (ITR) sequences from the AAV genome which are required for packaging and gene expression in the host or target cell. The missing viral functions can be supplied in trans by the packaging cell line. The viral nucleic acid can be packaged in a cell line, which contains a helper plasmid encoding the other AAV genes, namely rep and cap, but lacking ITR sequences. The cell line can also be infected with adenovirus as a helper. The helper virus can promote replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In some embodiments, the Cas9- and/or gRNA-encoding nucleic is delivered by a non-vector based method (e.g., using naked DNA or DNA complexes). For example, the nucleic acid can be delivered by organically modified silica or silicate (Ormosil), electroporation, gene gun, sonoporation, magnetofection, lipid-mediated transfection, dendrimers, inorganic nanoparticles, calcium phosphates, or a combination thereof.

In some embodiments, the Cas9- and/or gRNA-encoding nucleic acid is delivered by a combination of a vector and a non-vector based method. For example, a virosome comprises a liposome combined with an inactivated virus (e.g., HIV or influenza virus), which can result in more efficient gene transfer than either a viral or a liposomal method alone.

In some embodiments, nucleic acid encoding Cas9 molecules (or Cas9 polypeptide) and/or gRNA molecules can be delivered into cells by microinjection, electroporation, lipid-mediated transfection, peptide-mediated delivery, or a combination thereof. Delivery can be accompanied by DNA encoding a gRNA or by a gRNA.

The CRISPR/Cas9 constructs described herein may be delivered or introduced into a target cell by any suitable means, including, for example, by injection of mRNA or accordingly nucleic acid, for example, a CDNA, CRNA, or IRNA. See, Hammerschmidt et al. (1999) *Methods Cell Biol.* 59:87-115.

The mode of administering the CRISPR/Cas9 system is not limiting. Systemic modes of administration can include oral and parenteral routes. Parenteral routes include, by way of example, intravenous, intraarterial, intraosseous, intramuscular, intradermal, subcutaneous, intranasal and intraperitoneal routes.

In some embodiments, the Cas9 molecule and the gRNA molecule are delivered by different modes, or as sometimes referred to herein as differential mode. Different or differential modes, as used herein, refer modes of delivery that confer different pharmacodynamic or pharmacokinetic properties on the subject component molecule, e.g., a Cas9 molecule or gRNA molecule. For example, the modes of delivery can result in different tissue distribution, different half-life, or different temporal distribution, e.g., in a selected compartment, tissue, or organ.

Pharmaceutical Compositions

In another embodiment, the invention provides a pharmaceutical composition capable of genetically modifying a myosin phosphatase target subunit (Mypt1) gene in a vascular smooth muscle cell of the subject, whereby the genetic modification of Mypt1 results in a deletion or inactivation of exon 24. In some embodiments, the composition comprises one or more components of a CRISPR/Cas9 system as described herein. In some embodiments, the composition comprises a gRNA molecule comprising a targeting domain which is complementary with a target domain sequence of the Mypt1 gene and (b) a Cas9 molecule. In some embodiments, the composition comprises a nucleic acid composition comprising (a) a first nucleotide sequence encoding the gRNA molecule and (b) a second nucleotide sequence encoding the Cas9 molecule.

In some embodiments, the target domain sequence is selected from any one or combination of SEQ ID NO:1; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; and SEQ ID NO:17. In some embodiments, the gRNA is any one or a combination of SEQ ID NOS: 19-23. In some embodiments, Cas9 molecule is from *Staphylococcus aureus* and has the amino acid sequence of SEQ ID NO:24 or 25.

In some embodiments, the composition comprises an adeno-associated virus (AAV), such as AAV9, that encodes SEQ ID NO:24 or 25 and any one or a combination of SEQ ID NOS:19-23.

The pharmaceutical compositions can be formulated according to known methods for preparing pharmaceutically acceptable useful compositions, and may include a pharmaceutically acceptable carrier. The carrier may be liquid, solid, or semi-solid for example. Formulations are described in a number of sources which are well known to those of skill in the art. The physical and/or chemical characteristics of compositions of the inventions may be modified or optimized according to skill in the art, depending on the mode of administration. The compositions may be in any suitable form, depending on the desired method of administration.

The term "therapeutically effective amount" means the total amount of each active component of the pharmaceutical composition or method that is sufficient to show meaningful patient benefits, i.e, a decrease in the subject's blood pressure.

The pharmaceutical composition may be adapted for administration by any appropriate route, for example by the oral, rectal, nasal, topical, vaginal or parenteral routes.

Pharmaceutical compositions adapted for parenteral administration include aqueous and non-aqueous sterile injection solutions which may contain anti-oxidants, buffers, bacteriostats, and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in freeze-dried conditions requiring only the addition of a sterile liquid immediately prior to use. Extemporaneous injection solutions and suspensions may be prepared from sterile powders, granules, and tablets. The pharmaceutical compositions may contain preserving agents, solubilizing agents, stabilizing agents, wetting agents, emulsifiers, salts, buffers, antioxidants, etc.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1. A Splice Variant of the Myosin Phosphatase Regulatory Subunit Tunes Arterial Reactivity and Suppresses Response to Salt Loading The cGMP activated kinase cGK1a is targeted to its substrates via Leucine Zipper (LZ)-mediated hetero-dimerization and thereby mediates vascular smooth muscle (VSM) relaxation. One target is myosin phosphatase (MP) which when activated by cGK1a results in VSM relaxation even in the presence of activating calcium. Variants of MP regulatory subunit Mypt1 are generated by alternative splicing of the 31 nt Exon 24 (E24) which by changing the reading frame codes for isoforms that contain or lack the C-terminal LZ motif (E24+/LZ−; E24−/LZ+). Expression of these isoforms is vessel-specific, developmentally regulated and modulates in disease and is described herein to confer sensitivity to NO/cGMP mediated vasorelaxation. As described herein, mice underwent Tamoxifen-inducible and smooth muscle-specific deletion of E24 (E24 cKO) after weaning. Deletion of a single allele of E24 (shift to Mypt1 LZ+) enhanced vasorelaxation of $1^{st}$ order mesenteric arteries (MA1) to DEA/NO, and to cGMP in permeabilized and calcium clamped arteries, and lowered blood pressure. There was no further effect of deletion of both E24 alleles, indicating high sensitivity to shift of Mypt1 isoforms. However, a unique property of MA1s from homozygous E24 cKOs was significantly reduced force generation to α-adrenergic activation. Furthermore two weeks of high salt (4% NaCl) diet increased MA1 force generation to phenylephrine in control mice, a response that was markedly suppressed in the E24 cKO homozygotes. Thus, Mypt1 E24 splice variants tune arterial reactivity and are worthy targets for lowering vascular resistance in disease states.

Molecular mechanisms determining differential sensitivity of smooth muscles to nitric oxide-mediated relaxation have not been defined. This study uses a genetic mouse model to demonstrate that splice variants of myosin phosphatase set vascular smooth muscle sensitivity to NO and cGMP-mediated relaxation and thereby control blood pressure.

The testing of this MP "LZ hypothesis" and determination of the magnitude of the effect of the isoforms in determining vasodilator response to NO/cGMP in vivo requires a model in which the expression of the Mypt1 E24/LZ isoforms can be manipulated as independent variables in vivo. To accomplish this LoxP sites were inserted into the introns flanking mouse Mypt1 E24. Crossing these mice into a line in which Cre is conditionally expressed specifically within smooth muscle (SMMHCCre$^{ER}$) (Wirth et al., Nat Med 14: 64-68, 2008) and treatment with Tamoxifen leads to the deletion of E24 (E24 cKO), thereby shifting smooth muscle towards the Mypt1 E24−/LZ+ isoform. In initial studies, heterozygous E24 cKO mice were used to recapitulate changes in Mypt1 E24/LZ isoforms in models of arterial maturation (Reho et al., Am J Physiol Heart Circ Physiol 307: H563-573, 2014) and sepsis (Reho et al., Am J Physiol Heart Circ Physiol 308: H1039-1050, 2015). It is shown that shift towards the Mypt1 E24−/LZ+ isoform lowered blood pressure (BP) and increased sensitivity to cGMP-mediated relaxation of the mesenteric arteries from otherwise normal adult mice. The goals of the current study were two-fold: 1) to determine the dose-response relationship between expression of Mypt1 E24/LZ+/− variants and arterial function and BP 2) to test the hypothesis that forced expression of the Mypt1 E24−/LZ+ isoform (E24 cKO) will have salutary effects on arterial function and BP in a disease model, in this instance the stress of a high salt diet.

Materials and Methods

Animal Model

All animal protocols were reviewed and approved by the Institutional Animal Care and Use Committee at the University of Maryland and adhere to NIH guidelines. Using Zinc Finger Nuclease methodology in the inbred C57Bl/6J mouse line (Sage Labs, Boyertown, Pa.), LoxP sequences were inserted in the introns flanking mouse Mypt1 E24 outside of conserved putative cis-regulatory splicing sequences (FIG. 1 and (Dippold et al., Am J Physiol Regul Integr Comp Physiol 307: R256-270, 2014; Shukla et al., Circ Res 103: 485-492, 2008)) (NCBI reference sequence: NC_000076.6 genomic coordinates 109001-115256). Targeted integration genotyping was achieved by placing restriction enzyme sequences (BsiWI and Hind III) next to each LoxP site. Mice with the E24 floxed allele were then bred to the smooth muscle specific SMMHCCre$^{ER}$ mouse (Wirth et al., Nat Med 14: 64-68, 2008). Cre was activated in male mice via intraperitoneal injection of Tamoxifen (Sigma; 50 mg/kg in sunflower oil) for 3 consecutive days at 3 weeks of age. These mice are described as E24 cKO. Control Cre+ mice without foxed alleles were treated in the same manner. Mice were studied at 8-12 weeks of age. A subset of mice was placed on a high salt (4% NaCl) diet for 2 weeks prior to study. The control mice in these experiments were continued on their normal salt diet (0.4% NaCl).

RNA Analysis

Blood vessels were dissected from the mice and stored in RNA later prior to homogenization and column purification of RNA (RNEasy® Kit for column purification of RNA, Qiagen, Valencia, Calif.). Total RNA (100 ng) was reverse transcribed using SuperScript™ III enzyme (1000 U; ThermoFisher Scientific, Waltham, Mass.) and cDNAs were subjected to conventional and quantitative real-time PCR as previously described (Reho et al., Am J Physiol Heart Circ Physiol 307: H563-573, 2014). The Mypt1 E24 alternative exon splice variants were amplified in a single PCR using IR-labeled primers that flank the alternative Mypt1 E24 exon. PCR products (E24+ and E24−) were gel separated, amplicon bands directly quantified with an Odyssey® digital imaging system (LI-COR Biotechnology, Lincoln, Nebr.) and data reported as % Mypt1 E24 inclusion. Taqman™ probes (Applied Biosystems, ThermoFisher Scientific, Waltham, Mass.) were used to quantify mRNAs by real-time PCR and normalized to cyclophilin A (Ppia) which was invariant. Data are expressed as fold-change of transcripts using the $2^{-ddCt}$ method.

Protein Analysis

Mesenteric arteries and aortas were homogenized using a Bullet Blender® (Next Advance, Inc., Troy, N.Y.) in a lysis buffer containing 125 mM Tris-HCl (pH 6.8), 20% sucrose, 10% SDS, and 1% proteinase inhibitor cocktail. Protein lysates (10.mu.g) were loaded into 4-15% Tris-glycine gels (Mini-PROTEAN® TGX™; Bio-Rad, Hercules, Calif.), separated at 80V for 1.5 hr, and transferred to nitrocellulose at 25V for 2 hrs. Membranes were blocked with LI COR Odyssey® blocking buffer and incubated with primary antibodies overnight at 4 C. Rabbit polyclonal antibodies specific for the Mypt1 LZ+ and LZ− isoforms were used at 1:3000 dilutions as previously described (Reho et al., Am J Physiol Heart Circ Physiol 307: H563-573, 2014). Membranes were incubated with secondary IRDye® antibodies (800CW and 680LT) (1:10000) (Abcam, Cambridge, UK), imaged in the LI COR Odyssey® digital scanner and quantified with Image Studio™ 3.0 software (LI-COR, Lincoln, Nebr.). Membranes were then stripped and re-probed with a rabbit polyclonal antibody that detects all isoforms of Mypt1

(ab24670; Abcam). The LZ− signal in each sample was divided by the LZ+ signal in each sample, and then by the Mypt1 signal for internal normalization, which was invariant. The values of the Mypt1 LZ−/LZ+ ratios are reported as fold-change vs control samples.

Vascular Function

First-order mesenteric arteries (2 mm length; 200-250 µm ID) were dissected free of connective tissue in a HEPES-bicarbonate physiological saline solution containing the following concentrations (in mM): 112 NaCl, 25.7 NaHCO$_3$, 4.9 KCl, 2.0 CaCl$_2$, 1.2 MgSO$_4$, 1.2 KH$_2$PO$_4$, 11.5 glucose, and 10 HEPES. The solution was at pH 7.4 and maintained at 37 C for experiments. Arteries were mounted on a 4-chamber wire myograph (Model 610M, Danish Myo Technology, Aarhus, Denmark). Force was continuously recorded and measured at steady state. Starting tension (IC$_{90}$) was equally applied to all arteries as previously described (Reho et al., *Am J Physiol Heart Circ Physiol* 307: H563-573, 2014). Arteries were then primed with 2 separate dose of phenylephrine (10 µM) and allowed to equilibrate for 20 minutes in fresh, heated HEPES-bicarbonate buffer. Intact arteries were subjected to dose response to phenylephrine (α-adrenergic agonist; 1 nM-100 µM), U46619 (thromboxane mimetic; 1 nM-10 µM), and angiotensin II (1 nM-10 µM). Maximal response of MAs to depolarization was assessed with 100 mM KCl. A subset of arteries was permeabilized with α-toxin (1000 U/mL) and subjected to calcium clamp in high relaxing solution (pCa9) containing the following (in mM): 60 KMS, 5 EGTA, 0.02 CaCl$_2$, 9.26 MgCl$_2$, 5.2 Na$_2$ATP, 25 creatine phosphate, and 25 BES with pH 7.1 (intracellular pH) by 1N KOH. Permeabilized arteries were subjected to dose response of calcium. Phenylephrine-induced calcium sensitization was performed under calcium clamp at a sub-maximal concentration of calcium (pCa6; 1 µM) with intracellular calcium stores depleted by preincubation of arteries with 10 µM A-23187. Vessels were activated with 10 µM phenylephrine with or without preincubation with L-NAME (100 µM). Vasorelaxation responses to the NO donor DEA/NO were assessed in intact arteries activated with a sub-maximal concentration of phenylephrine (10 µM). Dose response to 8-Br-cGMP (1 nM-100 µM) were assessed in α-toxin permeabilized, calcium-clamped (pCa6; 1 µM) arteries. Relaxation data are presented as percent of maximal force. All chemicals were purchased from Sigma-Aldrich (St Louis, Mo.).

Telemetry Blood Pressure

Arterial pressure was measured via telemetry in conscious mice (12-16 weeks of age) using PA-C10 transmitters (Data Sciences, St. Paul, Minn.), detected using telemetry receiving platforms and analyzed using Dataquest software as previously described (Escano et al., *Am J Physiol Regul Integr Comp Physiol* 297: 2, 2009). The transmitters were implanted into the left carotid artery and mice were allowed to recover for one week prior to turning on the transmitters. Blood pressure was measured continuously over the course of 3 consecutive days (day and night readings) at 10 min intervals and reported as the average of the mean arterial pressure over the 3 day period.

Statistics

All data are presented as means±SEM. Data were analyzed and graphed using SigmaPlot software (SYSTAT, Chicago, Ill.). mRNA and protein data and mean arterial pressures were analyzed using a one way ANOVA. Vascular function data were analyzed via One way ANOVA and a Bonferroni post-hoc test or Two way repeated measures ANOVA and a Bonferroni post-hoc test. EC$_{50}$ were calculated via standard curve analysis. Significance was accepted with a p<0.05.

Results

Efficient Deletion of E24 from Mypt1 in Vascular Smooth Muscle

Figure 1C:
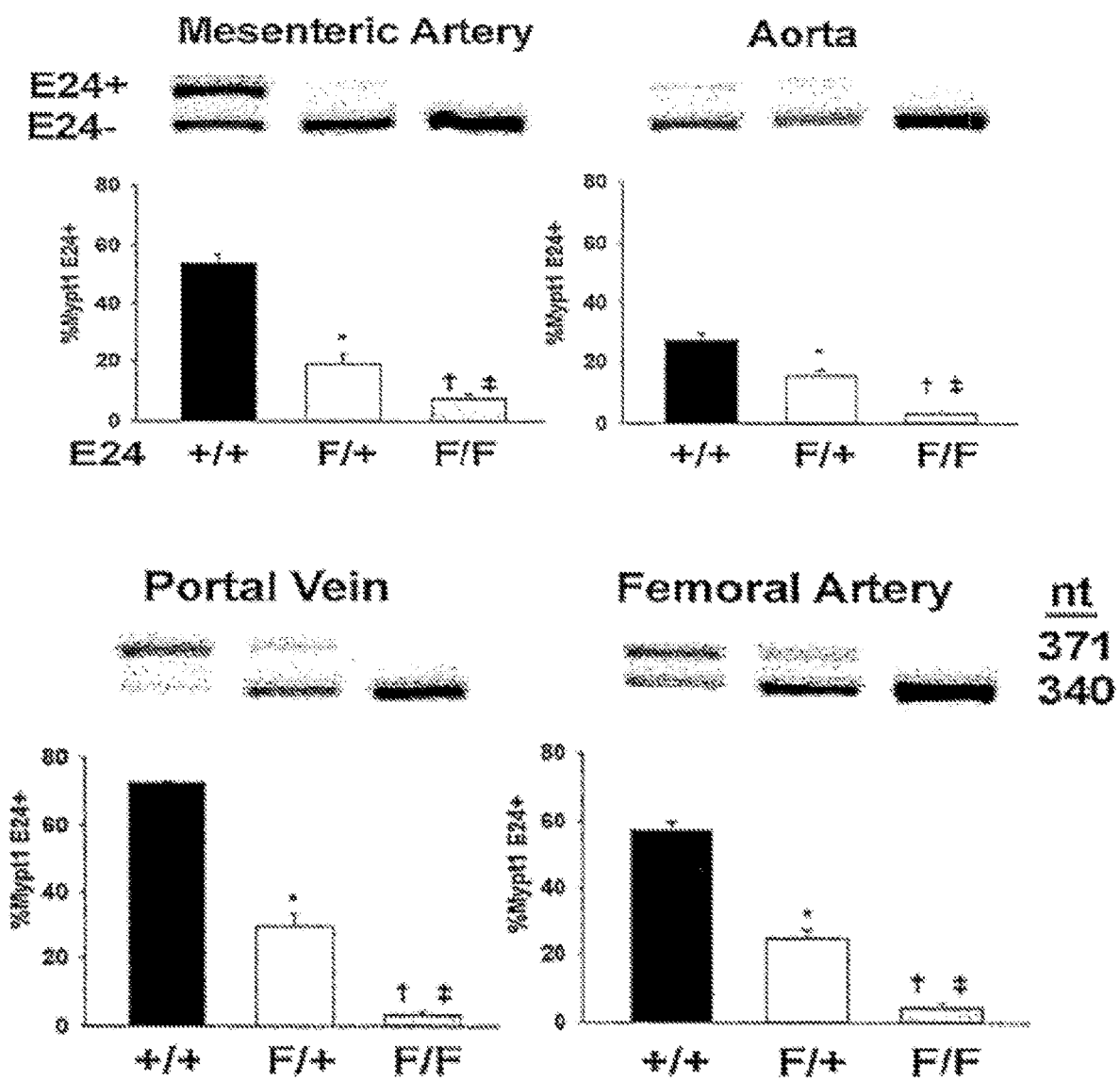

Treatment of male mice with Tamoxifen (50 mg/kg IP) for 3 consecutive days at 3 weeks of age resulted in efficient smMHCCre$^{ER}$-mediated deletion of E24 from the Mypt1 mRNA measured at 8-12 weeks of age (FIG. 1C). In mice with one foxed allele (F/+), there was an approximate 50% relative reduction in Mypt1 transcripts that were E24+ while in the homozygotes (F/F) there was nearly complete deletion of E24. The absolute magnitude of the change was dependent upon the basal level. The phasic smooth muscle of the portal vein has the highest basal level of inclusion and thus the largest absolute drop, while the mesenteric and femoral arteries are intermediate, and the tonic smooth muscle of the aorta the lowest level of inclusion and thus the smallest, yet still significant, reduction. The Mypt1 E24 ratios in the control mice (Cre+ treated with Tamoxifen; FIG. 1C) were not different from un-treated wild-type mice (see (Reho et al., *Am J Physiol Heart Circ Physiol* 307: H563-573, 2014)). Similarly, mice of the genotype Cre+//F/F that were not treated with Tamoxifen had normal Mypt1 E24 ratios (MA: % Mypt1 E24+: 51.9±1.2%), indicating that insertion of LoxP sites, or treatment with Tamoxifen in the absence of recombination, did not alter the splicing of Mypt1 E24.

Figure 1D:
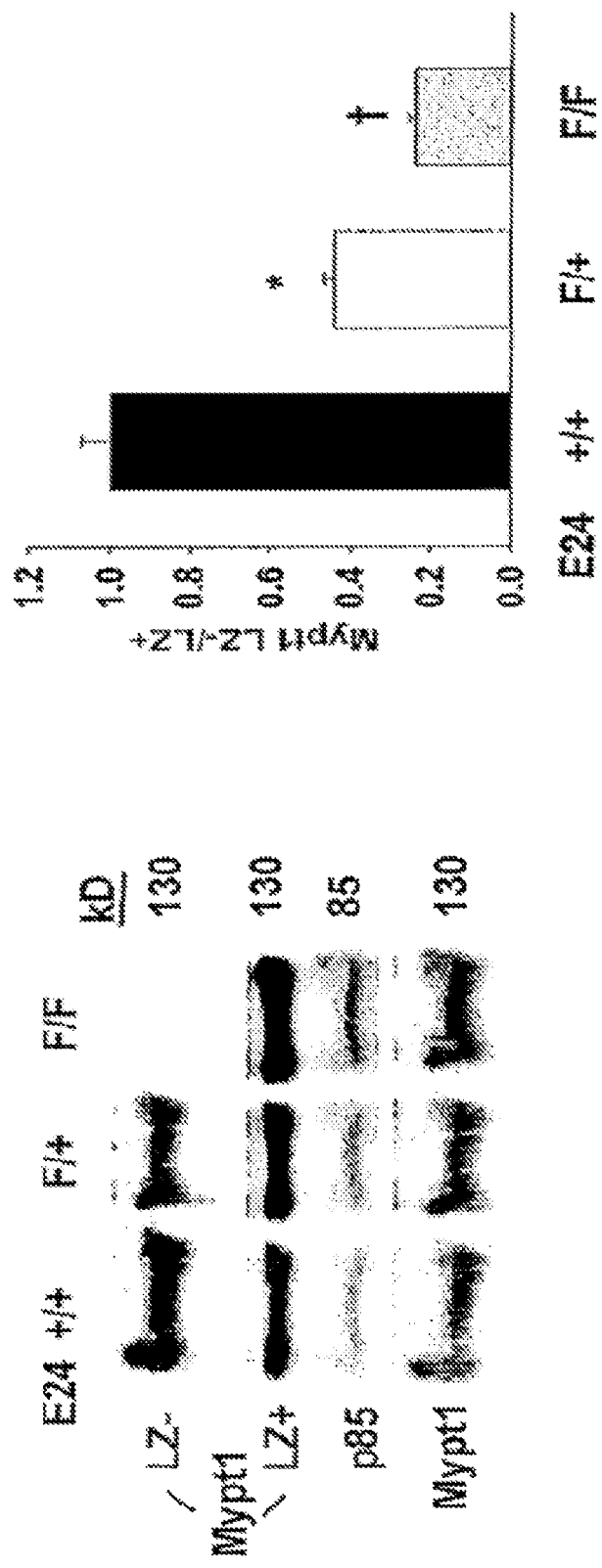

Isoform-specific antibodies confirmed that cKO of E24 caused the predicted reduction in the LZ− isoform of Mypt1 in the mesenteric arteries, with no change in the level of total Mypt1 and a corresponding increase in the Mypt1 LZ+ isoform (FIG. 1D). Again a dose-response was observed between the number of Mypt1 E24 floxed alleles and the decrease in the LZ− isoform and ratio of LZ−/LZ+(p<0.05).

Conditional KO of Mypt1 E24 Lowers Systemic Blood Pressure

Figure 2:
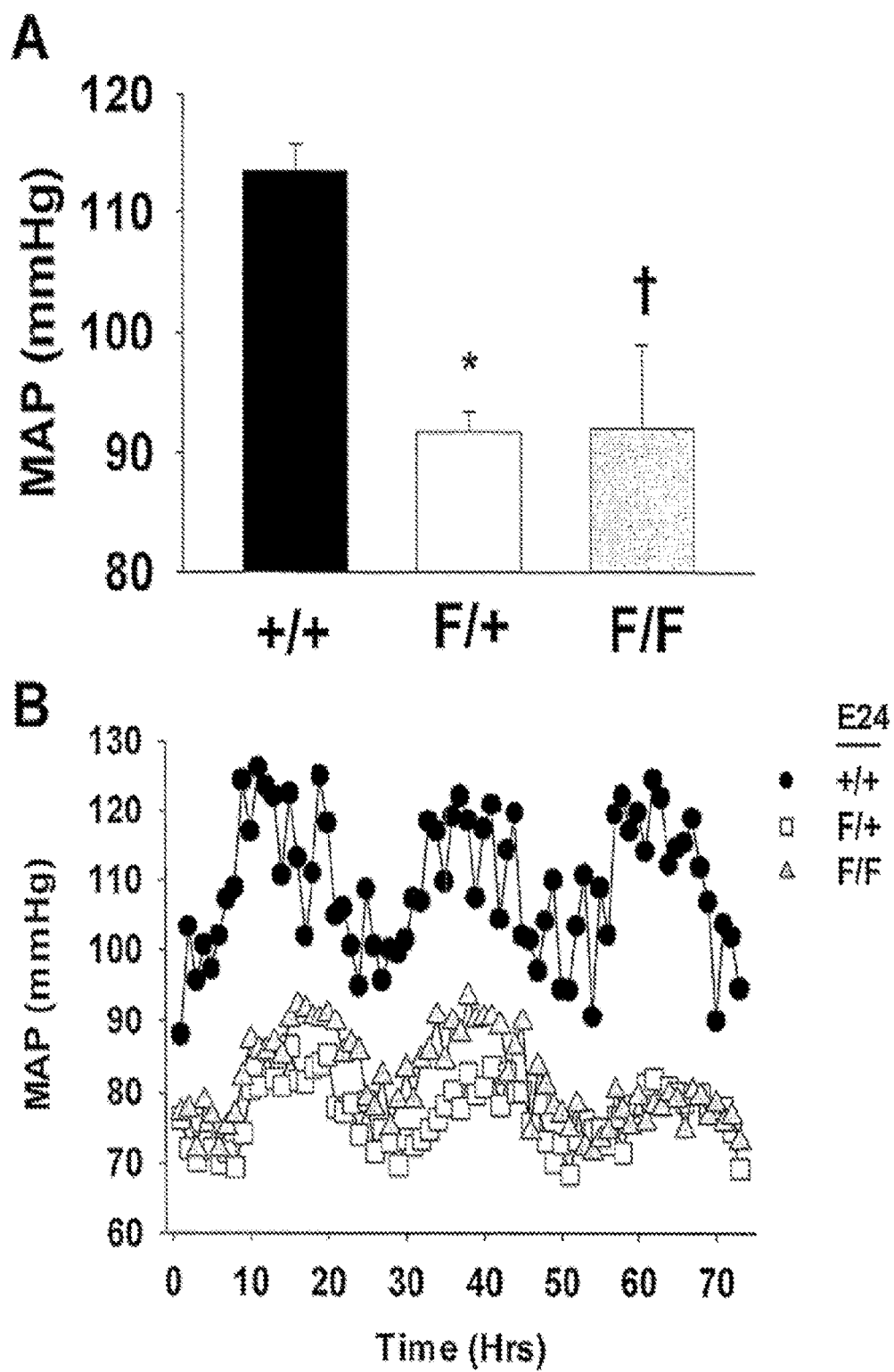
FIG. 2. Mypt1 E24 cKO lowers systemic blood pressure. Conscious blood pressure was continuously recorded over the course of 3 days 1 week after the implantation of the telemetry devices as described in Methods. Adult male mice were of genotypes as shown; all were Cre+ and treated with Tamoxifen. (A) Mean arterial pressure (MAP) (B) representative tracings of circadian fluctuations in MAP in a representative mouse from each group over the course of 72 hrs of recording. All data are expressed as means±SEM; n=3-5/group. *, †$p<0.05$ vs control.

Arterial pressure was measured by telemetry in conscious mice over the course of three consecutive days at age 12 weeks. Mice that were heterozygous for deletion of E24 had a ∼15 mmHg decrease in their mean arterial pressure (MAP) as compared to control mice (FIG. 2A; p<0.05). There was no further reduction in MAP in mice that were homozygous for deletion of E24. There was no change in the diurnal pattern of BP in these mice (FIG. 2B).

Conditional KO of Mypt1 E24 Increases Mesenteric Arterial Sensitivity to NO and cGMP To test the role of the Mypt1 LZ in determining arterial function, 1$^{st}$ order mesenteric arteries (MA1s) from E24 cKO mice were studied ex vivo by wire myography. MA1s from E24 cKO heterozygotes after pre-constriction with PE (10 µM) had markedly increased sensitivity of relaxation to the NO donor DEA/NO (FIG. 3A; EC$_{50}$: CON: 18.2±5.6 µM vs E24 F/+: 3.3±0.5 nM; p<0.05). The maximal response was also significantly increased with complete relaxation of E24 cKO MA1s at the highest concentration of DEA/NO.

Figure 3:
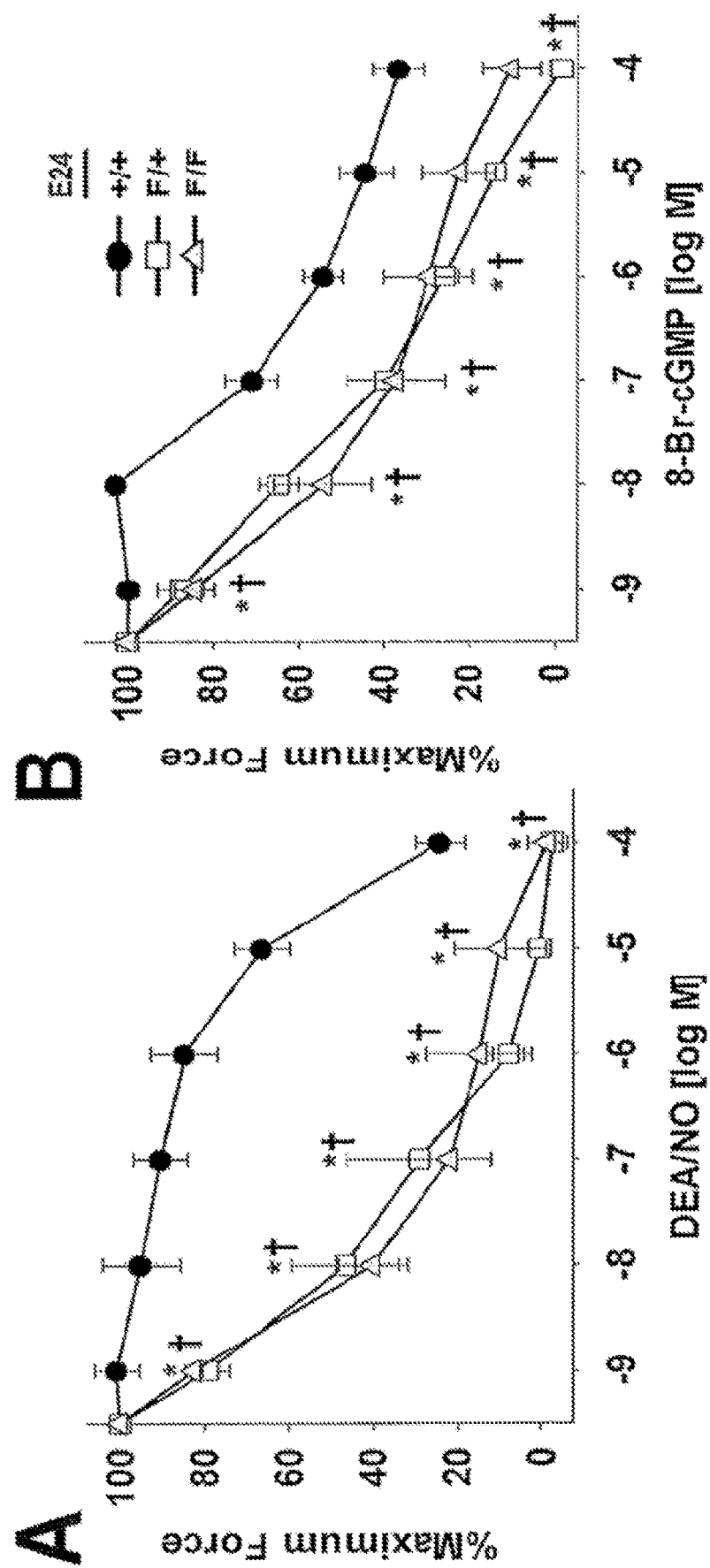
FIG. 3. Mypt1 E24 cKO increases mesenteric arterial relaxation to DEA/NO and 8-Br-cGMP. First-order mesenteric arteries (MA1) were harvested from adult mice with the genotypes as shown (all were Cre+ and treated with Tamoxifen) and mounted on a wire myograph. Force was continuously recorded from (A) intact and (B) α-toxin permeabilized $1^{st}$ order mesenteric arteries (MA1s). (A) MA1s were activated by 10 μM Phenylephrine followed by dose response to the NO donor DEA/NO. (B) MA1s were activated with sub-maximal concentrations of calcium (pCa6; 1 μM) followed by dose response to 8-bromo-cGMP (8-Br-cGMP). Data are presented as percentages of the maximum force generated. All data are expressed as means±SEM; n=5-6/group. *$p<0.05$ control vs heterozygotes; †$p<0.05$ control vs homozygotes.

MA1s from E24 cKO homozygotes exhibited the same dose-response to DEA/NO as did the heterozygotes (FIG. 3A; $EC_{50}$: E24 F/F: 2.1±0.5 nM; p<0.05 vs control). In MAs that were α-toxin permeabilized and activated with calcium (pCa6; sensitivity of relaxation to the cGMP analogue 8-Br-cGMP was markedly increased in MA1s from the Mypt1 E24 cKO heterozygotes (FIG. 3B; $EC_{50}$: CON: 95.2±11.0 nM; E24 F/+: 3.0±2.5 nM; p<0.05). The maximal response was also significantly increased with complete relaxation of E24 cKO MA1s at the highest concentration of 8-Br-cGMP. MA1s from E24 cKO homozygotes exhibited the same dose-response to 8-Br-cGMP as did the heterozygotes ($EC_{50}$: E24 F/F: 6.0±1.5 nM; p<0.05).

Conditional KO of Mypt1 E24 and Vasoconstrictor Responses

Figure 4A:
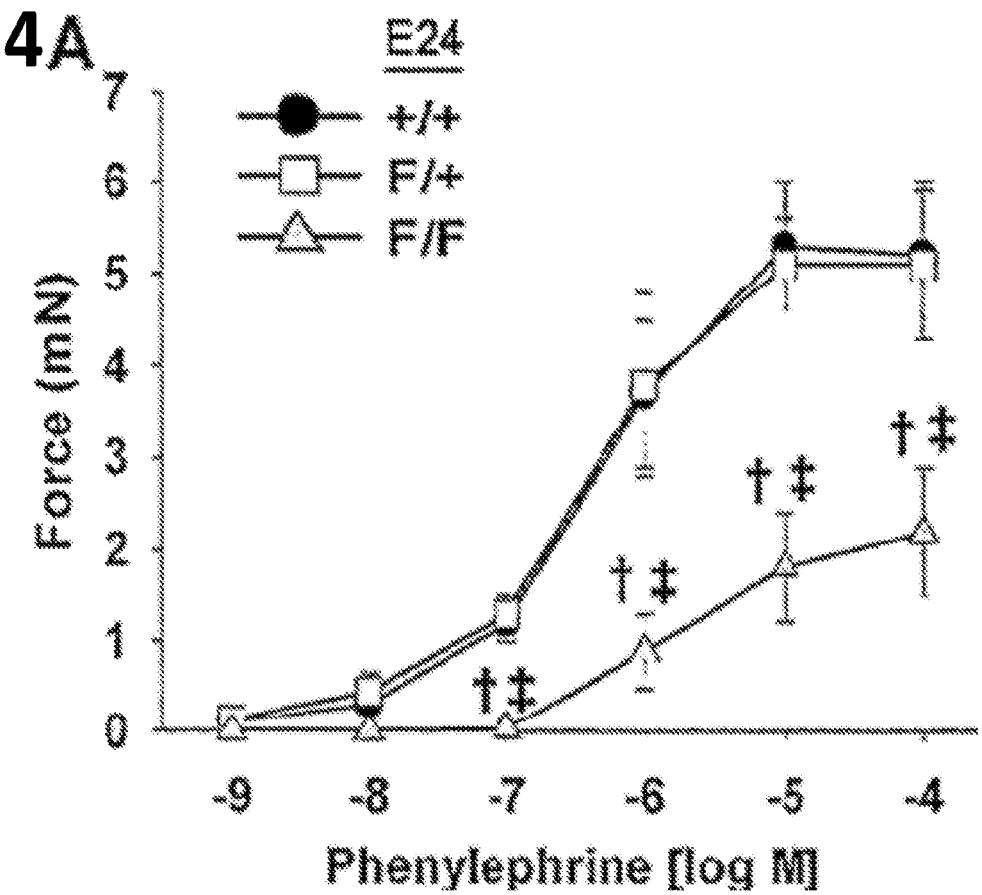
FIG. 4. Mypt1 E24 cKO reduces MA force generation to the α-adrenergic agonist phenylephrine selectively in homozygotes. Force (in mN) was continuously recorded in intact (A-D) and α-toxin permeabilized (E-F) MA1s from adult mice with the genotypes as shown (all mice were Cre+ and treated with Tamoxifen). Dose response to (A) phenylephrine (B) the thromboxane mimetic U-46619 (C) Angiotensin II. Force generation to (D) 100 mM KCl depolarization, (E) calcium, (F) submaximal concentration of calcium (pCa6; 1 μM) followed by PE (10 μM) with and without L-NAME pre-incubation (100 μM) to suppress synthesis of endogenous NO. All data are expressed as means±SEM; n=5-6/group. $p<0.05$ control vs homozygotes; ‡$p<0.05$ heterozygotes vs homozygotes.
Figure 4B:
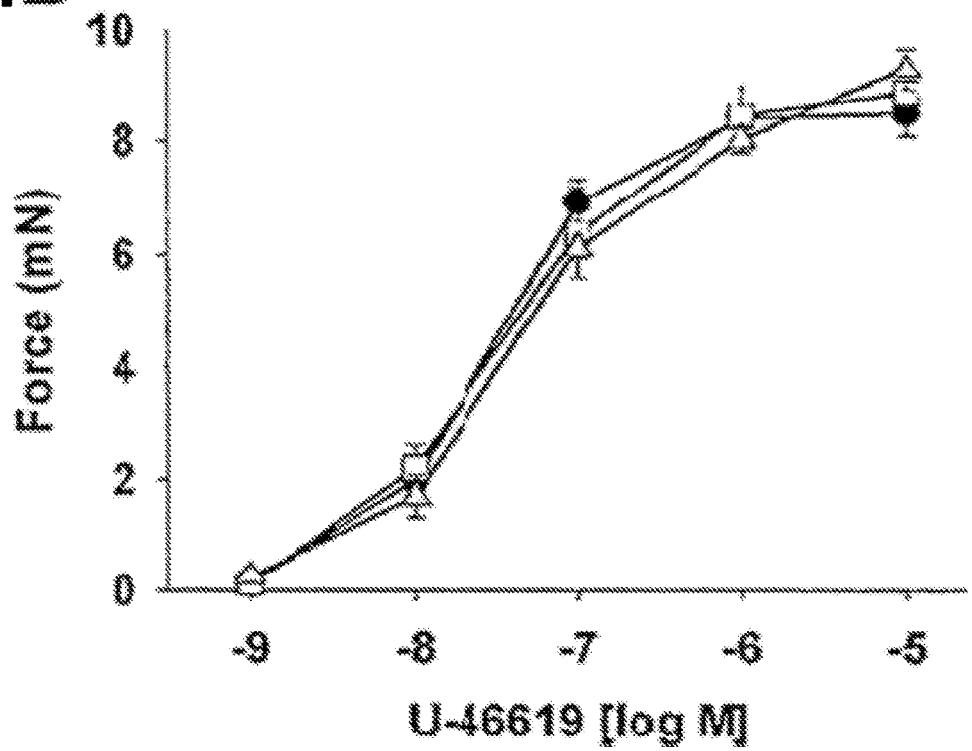
Figure 4C:
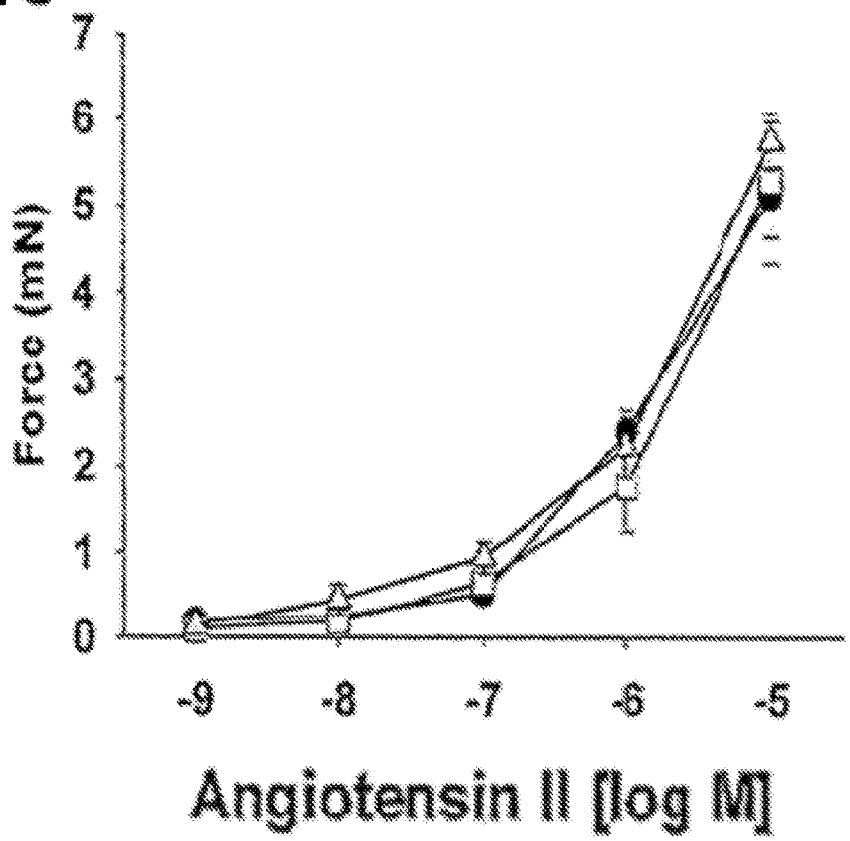
Figure 4D:
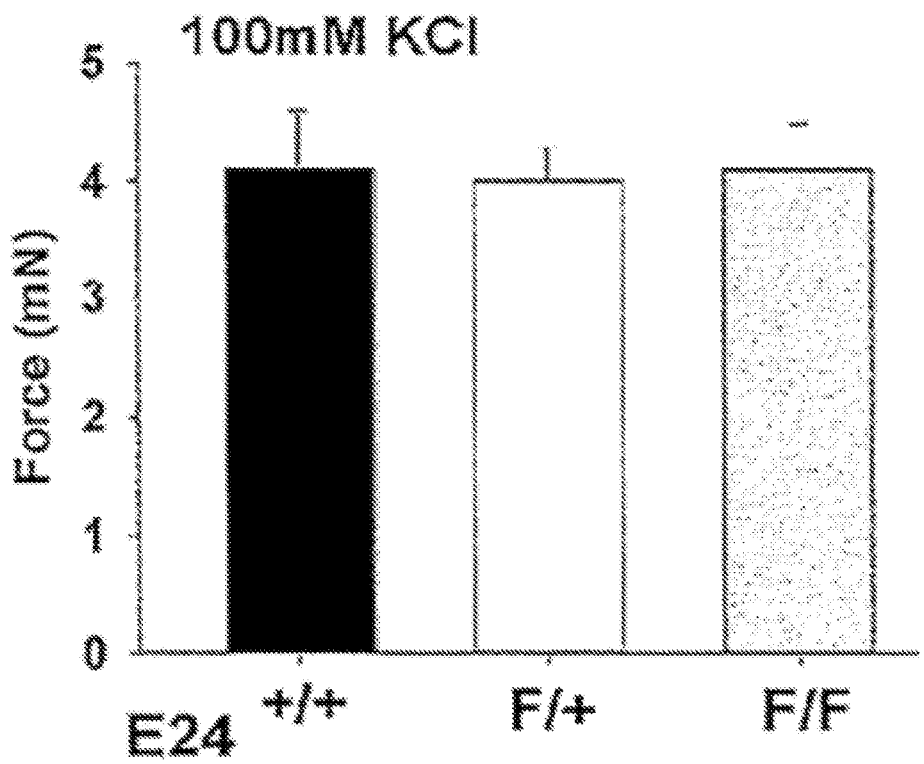
Figure 4E:
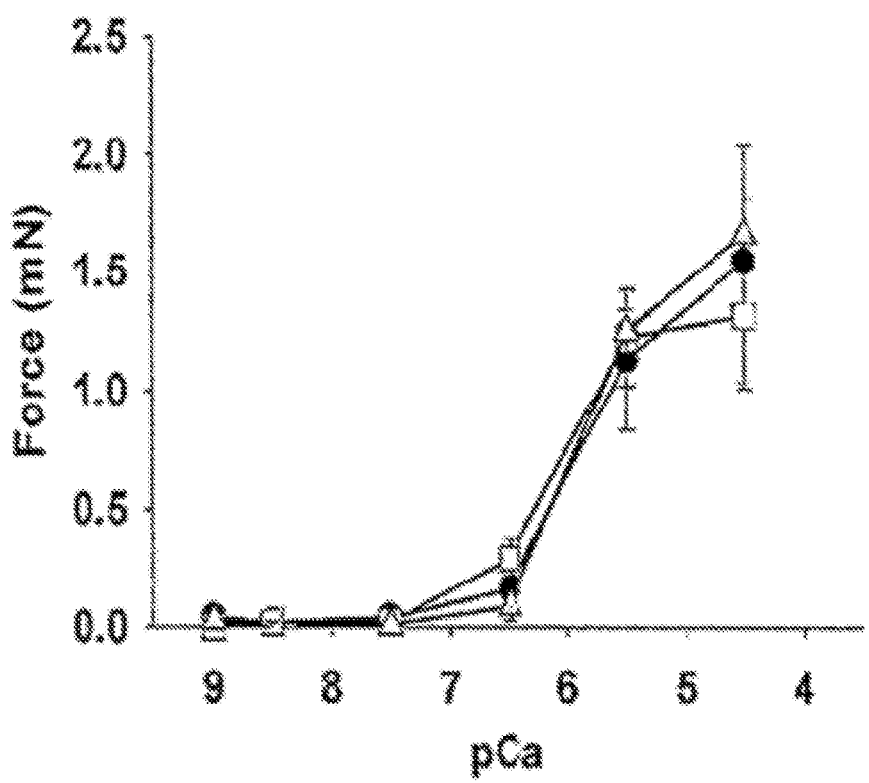
Figure 4F:
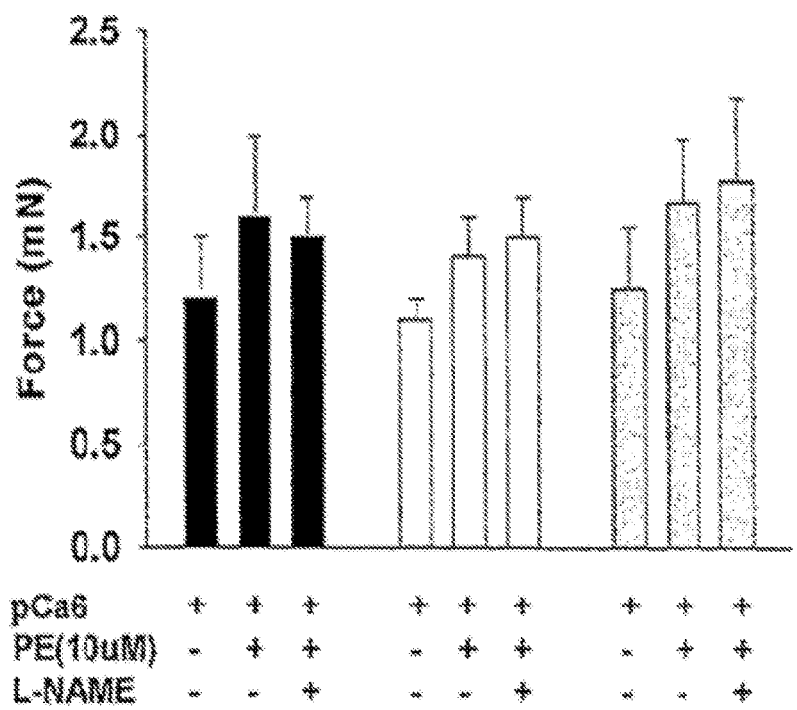
Figure 5A:
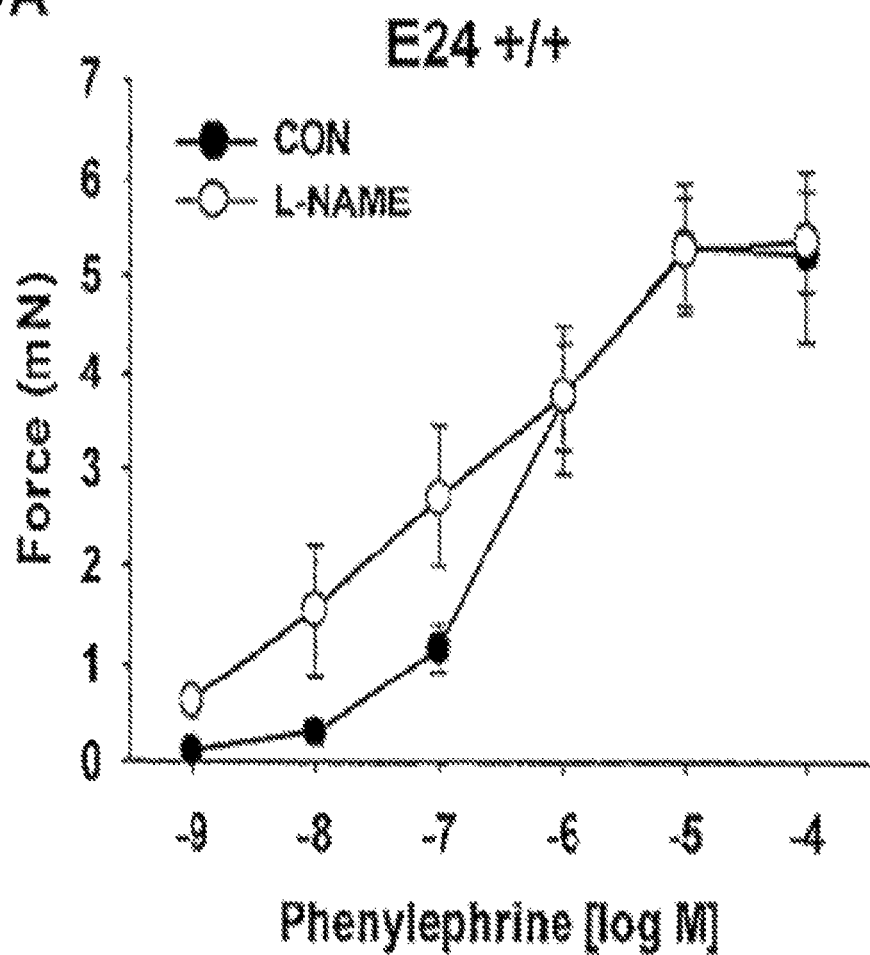
FIG. 5. Suppression of endogenous NO synthesis does not normalize MA force production to phenylephrine in E24 cKO homozygotes. Force (in mN) was continuously recorded in intact MA1s from adult mice with the genotypes as shown (all mice were Cre+ and treated with Tamoxifen). Dose response to PE with and without preincubation with L-NAME (100 µM) in control (A), E24 heterozygote (B), and E24 homozygote (C) mice. All data are expressed as means±SEM; n=5-6/group. *p<0.05.
Figure 5C:
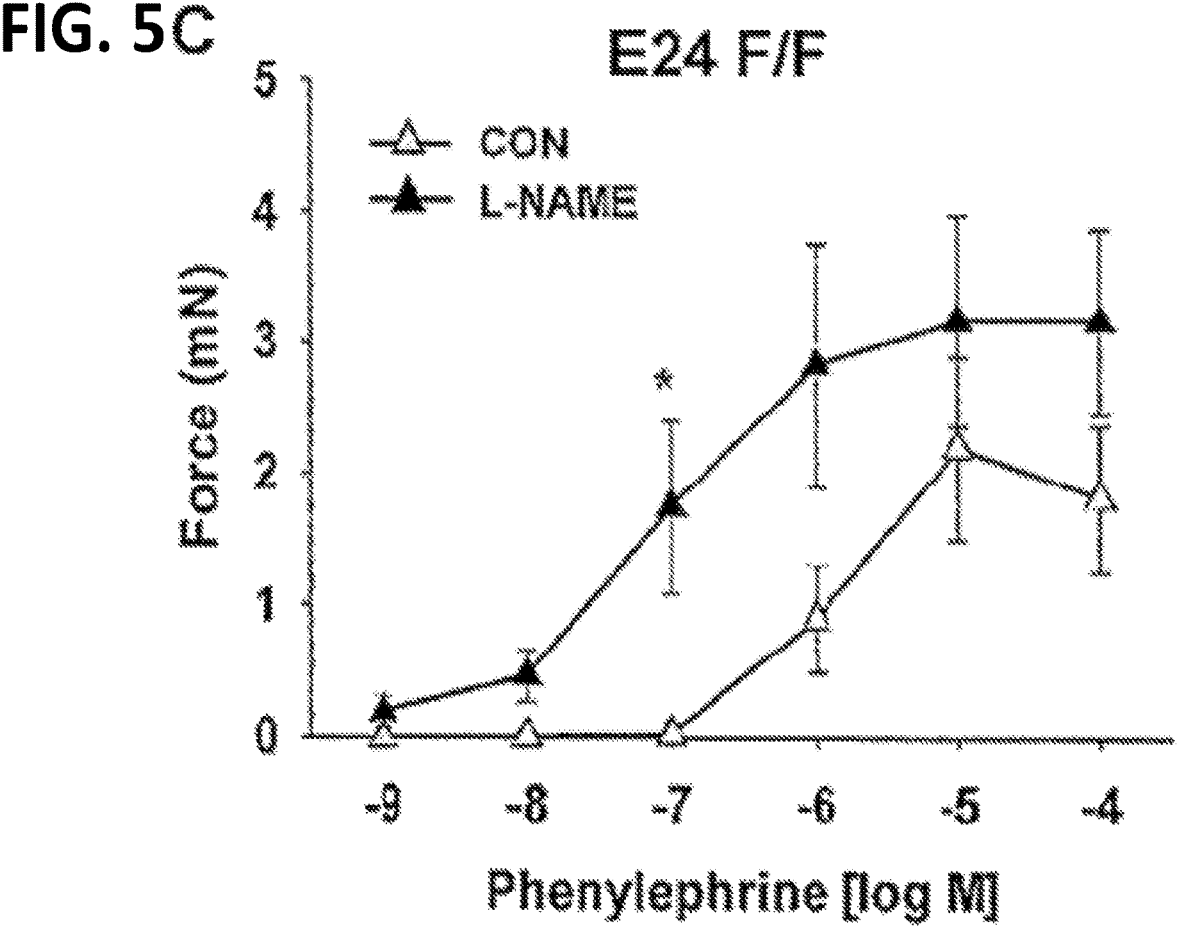

MA1s from E24 cKO heterozygotes had normal force generation to a variety of contractile agonists including the α-adrenergic agonist PE, the thromboxane mimetic U46619 and Angiotensin II (FIG. 4A-C). Similarly, force generation to depolarization induced with 100 mM KCl (FIG. 4D) and to calcium in α-toxin permeabilized preparations (FIG. 4E) was unchanged. Interestingly, MA1s from E24 cKO homozygotes had markedly reduced force generation that was selective for PE (FIG. 4A) as there was no change in the response to the other contractile agents (FIG. 4B-E). There was no change in the sensitivity of the MA1 E24 cKO homozygotes to PE ($EC_{50}$: CON: 0.5±0.1 μM; E24 F/+: 0.6±0.2 μM; E24 F/F: 0.9±0.2 μM). Pre-incubation with the arginine analogue L-NAME (100 μM) to suppress endogenous NO synthesis increased but did not normalize force production to PE in E24 cKO MA1 (FIG. 5C), compared to control where there was no change (FIG. 5A) and E24 cKO heterozygote MA1s where L-NAME significantly increased PE induced force production (FIG. 5B), suggesting an intrinsic and specific defect in the contractile response to this agonist in the E24 cKO homozygote mice. This did not appear to be a function of a change in the expression of ala-adrenergic receptor mRNAs in the MAs as there was no difference between groups (E24 F/+: 1.1±0.3; E24 F/F: 1.1±0.2; fold change vs CON; n=5-6). In MA1s that were α-toxin permeabilized and activated with sub-maximal calcium (pCa6; 1 μM), there was no difference between the groups in the increment in force with addition of PE (10 μM) and no effect in this assay of suppression of NO synthesis by pre-incubation with L-NAME (100 μM) (FIG. 4F).

Figure 6:
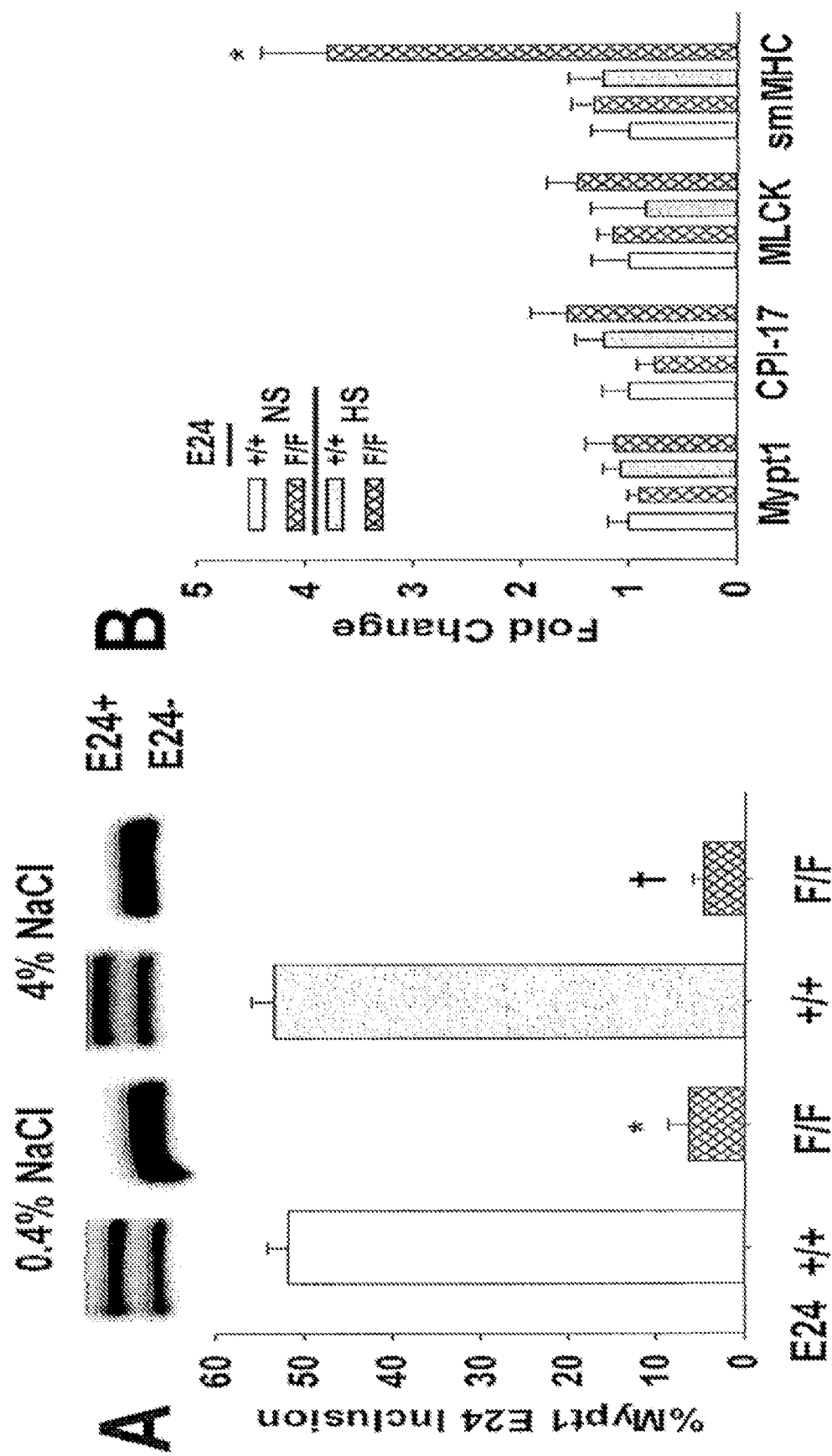
FIG. 6. Effect of 2 weeks of a high salt diet (4% NaCl) on mesenteric arterial gene expression. Adult mice of the genotypes as shown (all were Cre+ and treated with Tamoxifen) were fed a normal chow or high salt (4% NaCl) diet for 2 weeks. The mesenteric arterial arcade was isolated and (A) assayed for Mypt1 E24 splice variants as described above (B) Contractile gene mRNAs were assayed by qPCR using Taqman based probes and normalized to the invariant cyclophilin A (CycloA). Data are expressed as fold change. All data are expressed as means±SEM; n=4-5/group. Mypt1: myosin phosphatase targeting subunit 1; CPI-17: C-kinase potentiated inhibitory protein 1; MLCK: myosin light chain kinase; smMHC: smooth muscle myosin heavy chain. *p<0.05.

Conditional KO of Mypt1 E24 Suppresses Increased Arterial Contractility on a High Salt Diet To determine how E24 cKO may affect vascular function under conditions of stress, adult mice were fed a high salt (4% NaCl) diet for 2 weeks. High salt feeding did not change the ratio of Mypt1 E24+/– splice variants (FIG. 6A) nor the levels of Mypt1, CPI-17, and MLCK mRNAs (FIG. 6B) in the MAs of control and E24 cKO (F/F) mice. Interestingly, only in the E24 cKO mice on a high salt diet was smMHC mRNA significantly increased by ~4 fold (FIG. 6B).

Figure 7A:
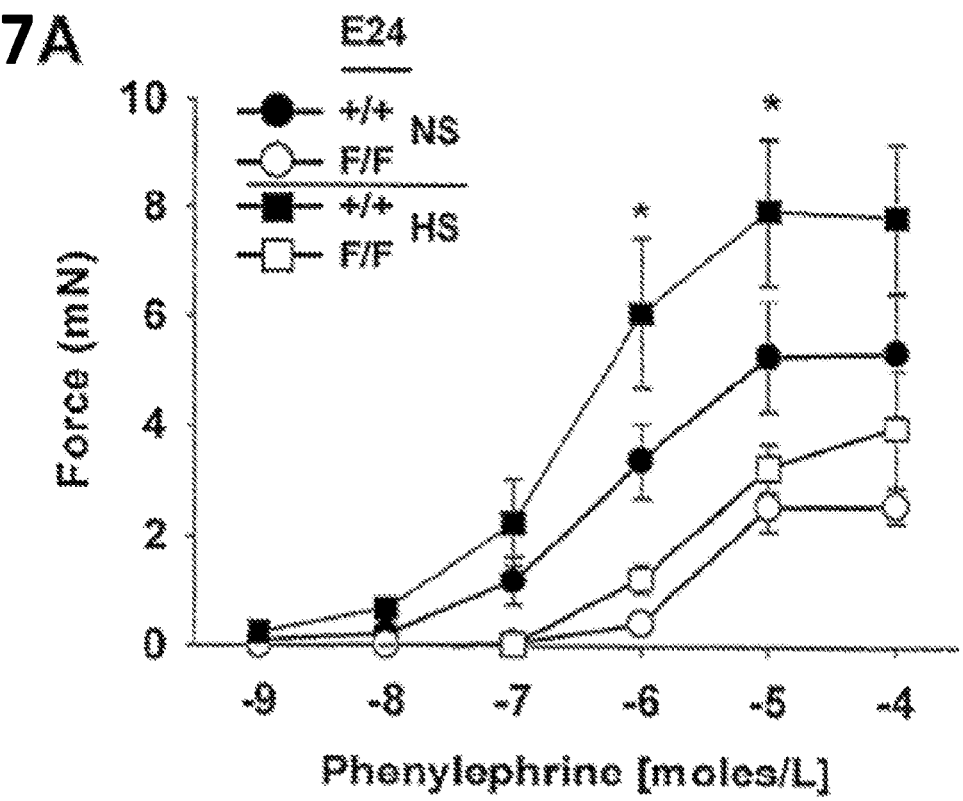
FIG. 7. Mypt1 E24 cKO specifically suppresses augmentation in MA1 force generation to phenylephrine after 2 weeks of high salt diet. MA1 s were harvested from adult mice of the genotypes shown (all were Cre+ and treated with Tamoxifen) on normal chow or high salt diet (4% NaCl) for 2 weeks. Force (mN) was continuously recorded from (A-C) intact and (D) α-toxin permeabilized arteries. (A) Dose-response to the α-adrenergic agonist PE. (B) Maximal force generated with 100 mM KCl depolarization. (C) Dose response to calcium. (D) Force was activated with sub-maximal concentration of calcium (pCa6; 1 µM) followed by dose response to 8-Br-cGMP. All data are expressed as means±SEM; n=3-4/group. *p<0.05 CON: normal chow vs high salt; †p<0.05 E24 cKO: normal chow vs high salt.
Figure 7B:
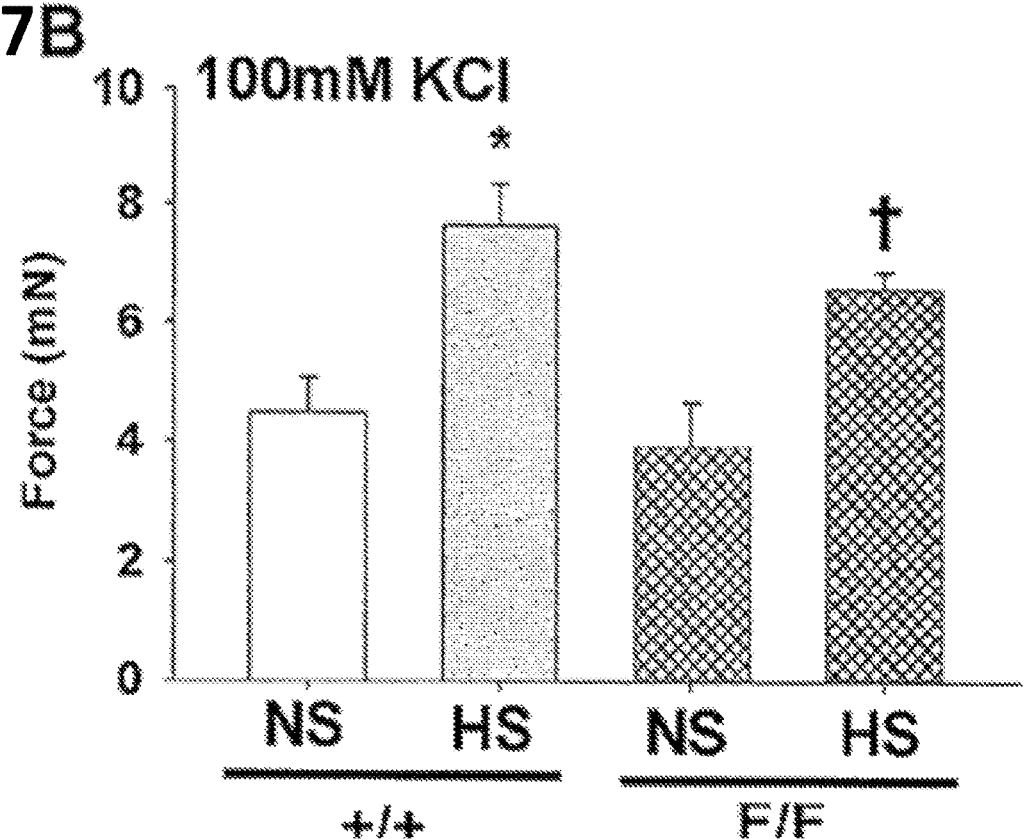
Figure 7C:
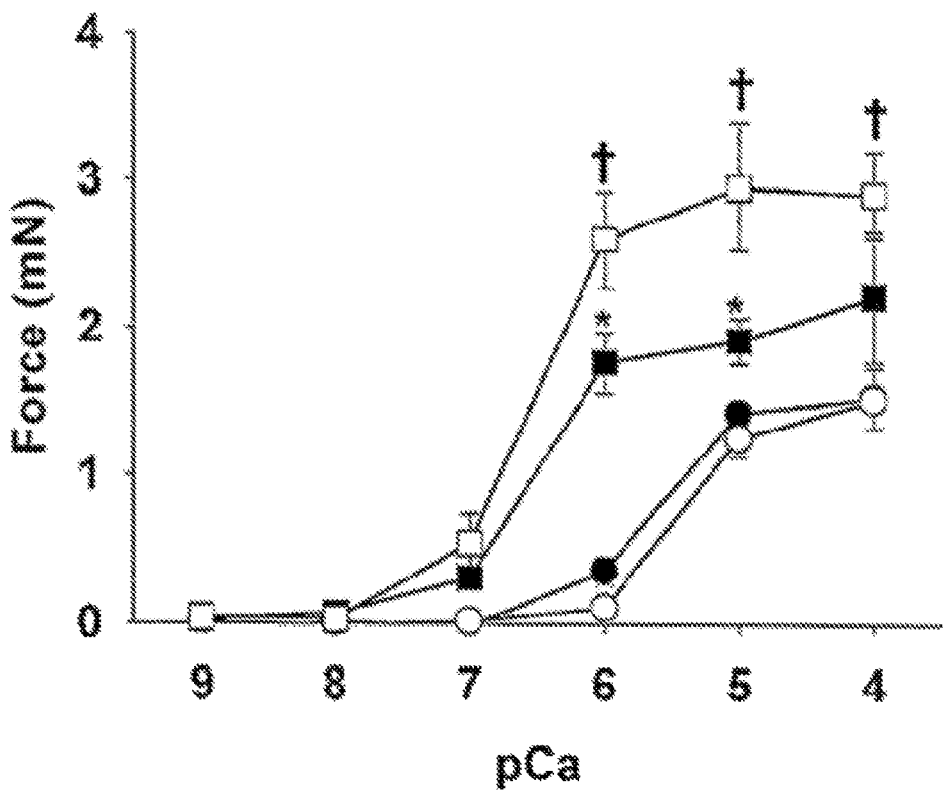
Figure 7D:
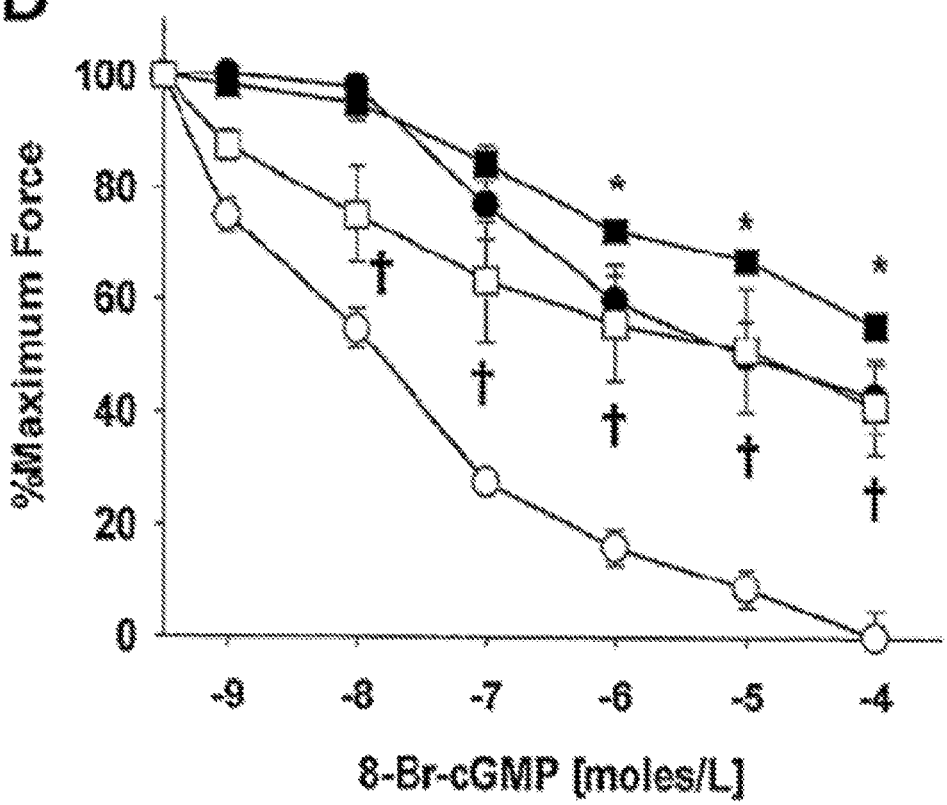

The effect of the high salt diet on MA contractile function was next examined. In MA1s from control mice on a high salt diet for 2 weeks, maximum force to the α-adrenergic agonist PE was markedly increased while there was no change in the sensitivity (FIG. 7A; $EC_{50}$: CON+NS: 0.9±0.4 μM; CON+HS: 1.0±0.5 μM; p>0.05). As noted above, MA1s from E24 cKO homozygotes had reduced maximal force generation to PE under basal condition, and in contrast to the control mice, had no augmentation in force production after 2 weeks of the high salt diet (FIG. 7A) and no change in the sensitivity (E24 F/F+NS: 0.4±0.2 μM; E24 F/F+HS: 3.0±1.0 μM). The suppressed response of E24 cKO MA1 to PE was again specific. MA1s from both control and E24 cKO mice had increased force generation to KCl depolarization (FIG. 7B) and to calcium (FIG. 7C) after 2 weeks of the high salt diet. In contrast the high salt diet reduced vasorelaxant sensitivity of MA1s to 8-Br-cGMP in α-toxin permeabilized and calcium activated (pCa6; 1 μM) preparations (FIG. 7D), with the magnitude of the shift greater in the E24 cKO as compared to the control mice.

In conclusion, Mypt1 E24 splice variant isoforms tune arterial reactivity under basal and pathological conditions and thereby control blood pressure. Sensitivity to NO/cGMP-mediated vasorelaxation is highly sensitive to increasing expression of the Mypt1 E24–/LZ+ isoform. Targeting of E24 may thus be a worthy goal for the treatment of the many human conditions in which systemic vascular resistance and blood pressure are increased.

Example 2. Viral Delivery of a Guide RNA for Genomic Editing of Mypt1 Exon 24 to Lower Blood Pressure The goal of this example is to develop an adeno-associated viral (AAV) vector for the purpose of editing of the Myosin Phosphatase gene Mypt1 in vascular smooth muscle in vivo. It is hypothesized that targeting of Mypt1 Exon 24 (E24) using this newly created AAV (AAV E24) for the purpose of genome editing will effectively and permanently lower vascular resistance and blood pressure. Control and hypertensive mice and rats will be injected with AAV E24; the endpoints to be measured over the following weeks include efficiency of Mypt1 E24 deletion in the arteries, arterial function and blood pressure.

Genome editing using Crispr/Cas9 enzymes and guide RNA is a technology adapted from lower organisms that enables precise and efficient targeting of DNA sequences in mammalian cells. The current example will use this novel approach to target Exon 24 of Myosin Phosphatase (MP) subunit Mypt1. MP causes vascular smooth muscle to relax thereby lowering blood pressure (BP). The activity of the MP enzyme is regulated by signals that lower or raise blood pressure. The presence of alternative Exon 24 (E24) in Mypt1 mRNA renders the MP enzyme resistant to activation by nitric oxide (NO) and other signals that may relax the smooth muscle and thereby lower blood pressure.

It is shown in Example 1 in a mouse model that Cre-Lox mediated deletion of Mypt1 E24 increases sensitivity to nitric oxide and thereby lowers BP. The goal of the current example is to use AAV-directed genome editing to inactivate Mypt1 E24 in blood vessels of hypertensive humans. This is an entirely novel approach to the treatment of hypertension in which the vascular smooth muscle is sensitized to endogenous signals that lower BP and increase blood flow. Infusion of adeno-associated viral vector (AAV) will be used to deliver the guide RNA and Cas9 to the blood vessels. Guide RNA containing the sequence to specifically target Mypt1 E24 will be subcloned into AAV expressing saCas9 (See, e.g., *Nature*, 520:186). This AAV will then be infused into rats and mice with normal and elevated BP. This AAV construct should delete Mypt1 E24 in the vascular smooth muscle and thereby permanently lower BP by –25 mmHg.

Recent pre-clinical animal studies by 3 different groups have shown that AAV directed genome editing, as proposed here, corrects Dystrophin expression and improves functional status in a mouse model of Duchenne's Muscular Dystrophy (Science 2016: 351:400,403,407). Other AAV vectors are in Phase III clinical trials, e.g. for treatment of hemophilia (Nature Rev Genet 2014:15, 445).

AAVE24 would initially be tested in patients in whom BP has been poorly controlled for many years putting them at high risk for stroke, heart and kidney failure, and death. This therapy requires a one-time treatment, and, based on animal studies, should lower systolic BP by −25 mmHg. This effect should be permanent or at least long lasting, unlike current medicines which must be taken daily for one's lifetime. This would bring many patients to goal BP while enabling others to substantially reduce the number of BP medicines they are taking, thereby improving compliance. Each 1 mmHg drop in BP causes a 2% reduction in cardiovascular morbidity and mortality. Thus AAV E24 could have a huge impact on the treatment of hypertension, and thus the health of economically disadvantaged populations where hypertension and its sequelae are endemic.

Construction and production of AAV for E24 editing: Plasmid pX601AAVCMVsgRNA was obtained from Addgene (#61591) and will be amplified for the purpose of sub-cloning the guide RNA targeting E24. According to web-based algorithm (Feng lab website: genome-engineering.org) this sequence is CGGCAAGAGTCAGTATCTTC (SEQ ID NO:1). Note this sequence (and E24) is identical in rodents and humans. This DNA and flanking sequence will be subcloned into the Bsa1 restriction site of pX601 vector by standard methods.

Testing efficacy of AAVE24 in vitro: Cultured HEK293 cells will be infected with AAVE24 at multiplicity of infection (MOI) of 10:1. After 7 days cells will be harvested and genomic DNA and mRNA purified. PCR assays will be used to test efficiency of AAV-mediated E24 deletion in the gene and the mRNA.

AAVE24 efficacy in vivo: AAV (10" units) is infused by tail vein into mature mice and rats. Normal mature and E24 cKO mice (described above) will be used. E24 cKO mice as control provide an elegant means of testing for off-target effects of AAVE24. Animals in each group will receive AAVE24 (experimental group) or AAV empty vector (control group). BP will be measured weekly by tailcuff and at termination (6 weeks). E24 deletion will be assayed by PCR in mRNA and genomic DNA of blood vessels and other tissues as previously described. Arteries will also be harvested and their function measured by wire myography as previously described. It is expected that lower BP and increased sensitivity to NO mediated vasorelaxation will be shown while general properties are unchanged.

AAVE24 or control AAV ($10^{11}$ units each) will be infused by tail vein into mature Spontaneously Hypertensive Rats (SHR) with the same experimental plan as described for mice. This will determine the magnitude of BP lowering in an animal model of hypertension.

Example 3. Genomic Editing of Mypt1 Exon 24 to Lower Blood Pressure

Myosin phosphatase target subunit 1 (MYPT1) is an important regulator of contraction and relaxation of vascular smooth muscle (VSM), playing a direct role in maintaining blood pressure. An alternative exon (E 24) was identified in MYPT1 (also known as PPP1R12A) gene that functions as a toggle to VSM sensitivity to endogenous vasodilators. When E24 is excluded from the mature messenger RNA (mRNA), there is full sensitivity of VSM to vasodilators and consequently decreased blood pressure. Excision or inactivation of alternative exon 24 from the genomic DNA results in its systematic exclusion from mRNA, and the transcription of PPP1R12A protein variant lacking exon 24, thereby converting VSM cells to maximum sensitivity to the endogenous vasodilators.

Derived from a prokaryotic adaptive immune system that uses RNA-guided nucleases to induce double stranded breaks in target DNA, the CRISPR-Cas genome editing technology was adapted to target loci of interest in eukaryotic, particularly mammalian cells. Cas9 are endonucleases that can be targeted specifically to any genomic locus via a 20-nucleotide guide (sgRNA) sequence that determines the specificity of Cas9 to its target, provided that the sequence is unique to the rest of the genome and that the target is present immediately upstream of a Protospacer Adjacent Motif (PAM). Cas9-mediated DNA cleavage occurs ~3 bp upstream of the PAM. The PAM sequence is specific to each Cas9 species and must be NNGRRT for *Staphylococcus aureus* Cas9 (SaCas9). In the present example, the alternative exon 24 was removed from the genomic DNA sequence of PPP1R12A using plasmid-delivered sgRNA-SaCas9 construct(s).

Material and Methods

Design and Selection of sgRNAs

Design of the sgRNAs was performed on the Benchling.com platform using the Design CRISPR Guides function. The target region on human PPP1R12A gene was set from 155881 bp to 156420 bp (gene sequence ENSG00000058272) allowing the screening of a 540 bp-long region flanking PPP1R12A exon 24 for potential sgRNA targets. Guides were subsequently evaluated for potential use in the mouse and rat by aligning the sequence of each sgRNA with the PPP1R12A murine sequences using MEGA 7.0.21 software. Guides with predicted efficiency and specificity scores exceeding 10% and 60%, respectively, alignments showing less than 8 mismatches between the sgRNA sequence and the human and murine PPP1R12A sequences and targeting a region immediately upstream of a NNGRRT PAM sequence in all 3 species of interest, were selected for experimental in vitro evaluation.

Vector and sgRNA Constructs

The px601-AAV-CMV::NLS-SaCas9-3xHA-bGHpA; U6::BsaI-sgRNA (px601) plasmid bearing both SaCas9 and a customizable U6-driven sgRNA scaffold for packaging into a single AAV vector has been previously described (Ran et al., Nature. 2015 Apr. 9; 520(7546):186-91) and graciously made available by Feng Zhang (Addgene Plasmid #61591). The constructs containing the sgRNAs that were selected for experimental evaluation as described above were generated by cloning the annealed oligos containing the sgRNAs sequences into the px601 plasmid. Briefly, the sgRNA sequences were ordered as standard oligos (Integrated DNA Technologies, Coralville, Iowa) with 5'-CACC and 5'AAAC overhangs to the sense and antisense oligos, respectively. A "G" nucleotide was added to the 5' end of the sgRNA when its sequence did not begin with a guanine in order to enhance the transcription from the U6 promoter. Cloning of the sgRNAs into the px601 vector was performed according to the Zhang Lab protocol (Feng Zhang lab, Massachusetts Institute of Technology, Cambridge, Mass.) In brief, in an in vitro reaction the oligos were phosphorylated with T4 polynucleotide kinase and annealed by heating to 95° C. followed by slow cooling. The parent pX601 plasmid was cut with the Bsa1 enzyme in an in vitro reaction. The Bsa1 cut plasmid was mixed with annealed oligos in an in vitro reaction with Quick Ligase enzyme (NEB) resulting in ligation of the oligos into the plasmid DNA. The sgRNA-px601 constructs were treated with Plasmid-Safe™ ATP-Dependent DNase (Biosearch Technologies/Epicentre, Middleton, Wis.) and heat-shock transformed into E. coli Endura™ Chemically Competent cells (Biosearch Technologies/Lucigen, Middleton, Wis.) according to the protocol supplied with the cells. A negative control containing the Bsa1-digested vector without sgRNA oligo insert was also transformed into competent cells. A total of 100 µL of transformed cells were spread on LB agar plates containing ampicillin and incubated overnight at 37° C. One day after transformation, the plates were inspected for colony growth. When colonies were present, 2 colonies were picked from each positive plate. Each single colony was inoculated into a 5 mL culture of LB medium with 100 µg mL$^{-1}$ ampicillin and grown overnight at 37° C. in a shaking incubator. The plasmids were consequently purified from liquid cultures using the ChargeSwitch®-Pro Plasmid Miniprep Kit (ThermoFisher Scientific, Waltham, Mass.) for ion-exchange purification according to the manufacturer's directions and the plasmid DNA was sequenced using U6-Forward primer: 5'-GAGGGCCTATTTCCCATATTCC-3' (SEQ ID NO:2) in order to confirm the presence of the sgRNA inserts in px601 vector.

Cellular Cultures

Human-derived HEK293T cells were maintained in Dulbecco's modified Eagle medium (DMEM, Life technologies), supplemented with 10% FBS and 1% penicillin/streptomycin solution. Cells were kept at 37° C. in a 5% $CO_2$ incubator.

Transfection Experiments

HEK293T cells were seeded at a density of 1.times.10.sup.5 cells/well in 24-well plates. After 24 hours, while cell confluence reached approximately 80%, cells were transfected with 1.mu.g of sgRNA-px601 vector (experimental conditions) or px601 vector (empty vector) or pIRES-EYFP vector (positive transfection control). All transfections were performed in duplicates using Lipofectamine® 3000 Reagent (Life Technologies/ThermoFisher Scientific, Waltham, Mass.) according to the manufacturer's protocol. Twenty-four hours after transfection, a volume of 0.5 mL of culture medium was added per well (reaching a total volume of 1 mL per well). Cells were harvested 72 hours after transfection; culture medium was removed, cells were trypsinized using Gibco™ TrypLE™ Express (Life Technologies/ThermoFisher Scientific), pelleted and cell pellets were stored at −20° C. The transfection efficiency was evaluated immediately prior to harvesting of cells, by inspection of HEK293T cells transfected with pIRES-EYFP vector using a Leica MZ-FLIII fluorescence microscope equipped with a GFP filter set (Leica Microscopy Systems Ltd., Heerbrugg, Switzerland).

DNA Analysis

Genomic DNA was purified from the transfected cells using PureLink™ Genomic DNA Mini Kit (Invitrogen/ThermoFisher Scientific, Waltham, Mass.) as per the manufacturer's protocol. In order to investigate if genome editing occurred, locus PCR amplifying a 754 pb-region flanking the exon 24 of PPP1R12A gene was performed using primers MYPT12AE24F 5'-ATGTTTAGGCATGCC-GATGT-3' (SEQ ID NO:3) (intronic region 155894 bp to 155913 bp on PPP1R12A ENSG00000058272) and MYPT12AE24R 5'-GCTTTGACTTTCTGGGAAGATG-3' (SEQ ID NO:4) (intronic region 156626 bp to 156647 bp on PPP1R12A ENSG00000058272). PCR conditions were as follows: 95° C. 5 min, then 95° C. 30 s, 53° C. 45 s, 72° C. 60 s for 30 cycles, with 5 min of final extension step at 72° C. PCR products were resolved by 2% agarose gel electrophoresis. When PCR product size was shorter than the control PCR product, genome editing occurred. For PCR products that could not be separated from the control product on 2% agarose gel due to the low resolution of the gel, a surveyor nuclease assay was performed using the Surveyor® Mutation Detection Kit (Integrated DNA Technologies, Coralville, Iowa) as per manufacturer's protocol for better visualization of the edits. The Surveyor® Mutation Detection Kit uses an endonuclease that cleaves DNA with high specificity at sites of mismatches and other distortions, allowing the detection of known and unknown DNA mutations. Briefly, target DNA is amplified by PCR from both wild-type (WT) and mutated DNA, WT and mutant DNA are then hybridized to form heteroduplexes, which are subsequently cleaved by the surveyor endonuclease. When no mutation is present, only homoduplexes are formed and no endonuclease-mediated cleavage is observed.

Results

In Silico sgRNA Evaluation

Figure 8:
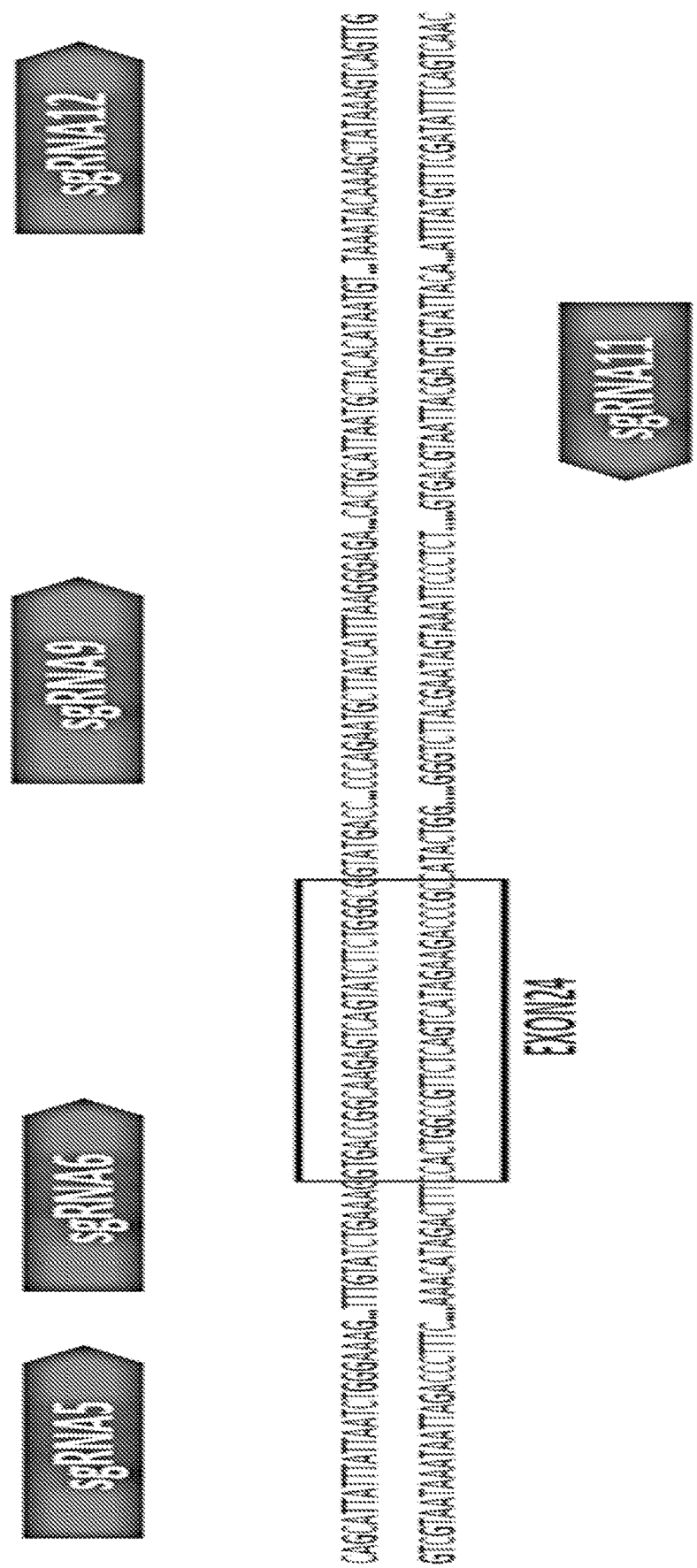
FIG. 8. Guide RNAs (sgRNAs) selected for experimental evaluation: Sequence of the target region flanking the exon 24 of PPP1R12A gene. The exon 24 of PPP1R12A is identified by a red box. Five sgRNAs (sgRNA5, sgRNA6, sgRNA9, sgRNA11 and sgRNA12) selected for in vitro evaluation are represented by grey pentagons positioned at the level of their target region on the genomic PPP1R12A sequence. sgRNA5 and sgRNA6 are located upstream the exon 24 of PPP1R12A gene with sgRNA6 overlapping the 3' end of the exon's splicing site. sgRNA9, sgRNA11 and sgRNA12 are located downstream the exon. All sgRNAs were evaluated individually and in combination with other sgRNAs located on the opposite side of the exon (sgRNAs 5+9, sgRNAs 5+11, sgRNAs 5+12, sgRNAs 6+9, sgRNAs 6+11, sgRNAs 6+12).

A total of 13 sgRNAs were identified by Benchling for potential use to target the PPP1R12A exon 24 flanking region. Four sgRNAs were eliminated for low predicted efficiency scores (sgRNAs 1, 4, 8, 10) (Table 1). Five other sgRNAs (sgRNAs 2, 3, 7, 9, 13) were eliminated due to important mismatches between the human and the murine DNA sequences and/or lacking PAM in the murine sequences, based on the alignment results (data not shown). Five sgRNAs were selected for further in vitro evaluation. All sgRNAs were evaluated individually, as well as in combination with other sgRNAs targeting the opposite side of the PPP1R12A exon 24, with the goal of total or partial excision of exon 24 (FIG. 8).

In Vitro sgRNA-Px601 Constructs Testing

Figure 9A:
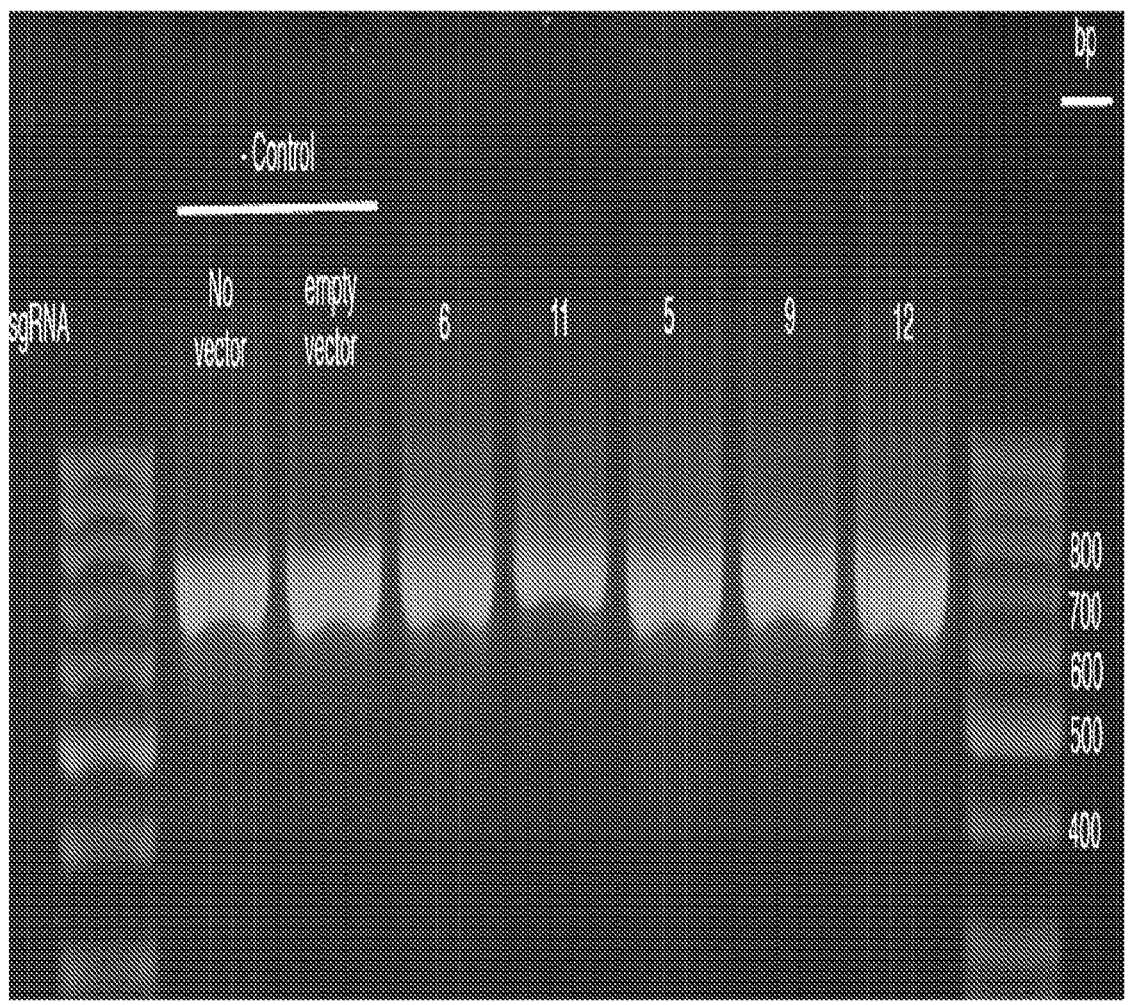
FIG. 9. The sgRNA-px601 constructs containing sgRNA6, sgRNA11, sgRNA5, sgRNA9 and sgRNA12 allowed effective genome editing in vitro. Genomic PCR targeting the PPP1R12A (Mypt1) exon 24 flanking region amplifies a 754 pb-DNA fragment (control). (A) sgRNA-px601 constructs tested individually yielded genomic edits that were below the resolution of the 2% agarose gel. (B) Surveyor nuclease yielded products of 250 bp and 500 bp after cleavage of heteroduplexes generated by hybridization of control DNA and DNA edited by sgRNA6-px601. Similarly, products of 320 bp and 430 bp, 120 bp and 630 bp, 330 bp and 420 bp, 270 bp and 480 bp were observed for DNA edited by sgRNA11-px601, sgRNA5-px601, sgRNA9-px601 and sgRNA12-px601, respectively. As expected, for each experimental condition, the sum of the sizes of both nuclease products was equal to the size of the control DNA (~750 bp). Only 1 product was observed for control DNA treated by surveyor endonuclease, reflecting the absence of mutations. (C) sgRNA-px601 6+11, 6+9, 6+12, 5+11, 5+9 and 5+12 duets yielded genomic edits which sizes were approximately 500 bp, 600 bp, 470 bp, 450 pb, 570 bp and 420 bp, respectively with a range of efficiencies extending up to ~40% (sgRNAs 6+11 and sgRNAs 5+11).
Figure 9B:
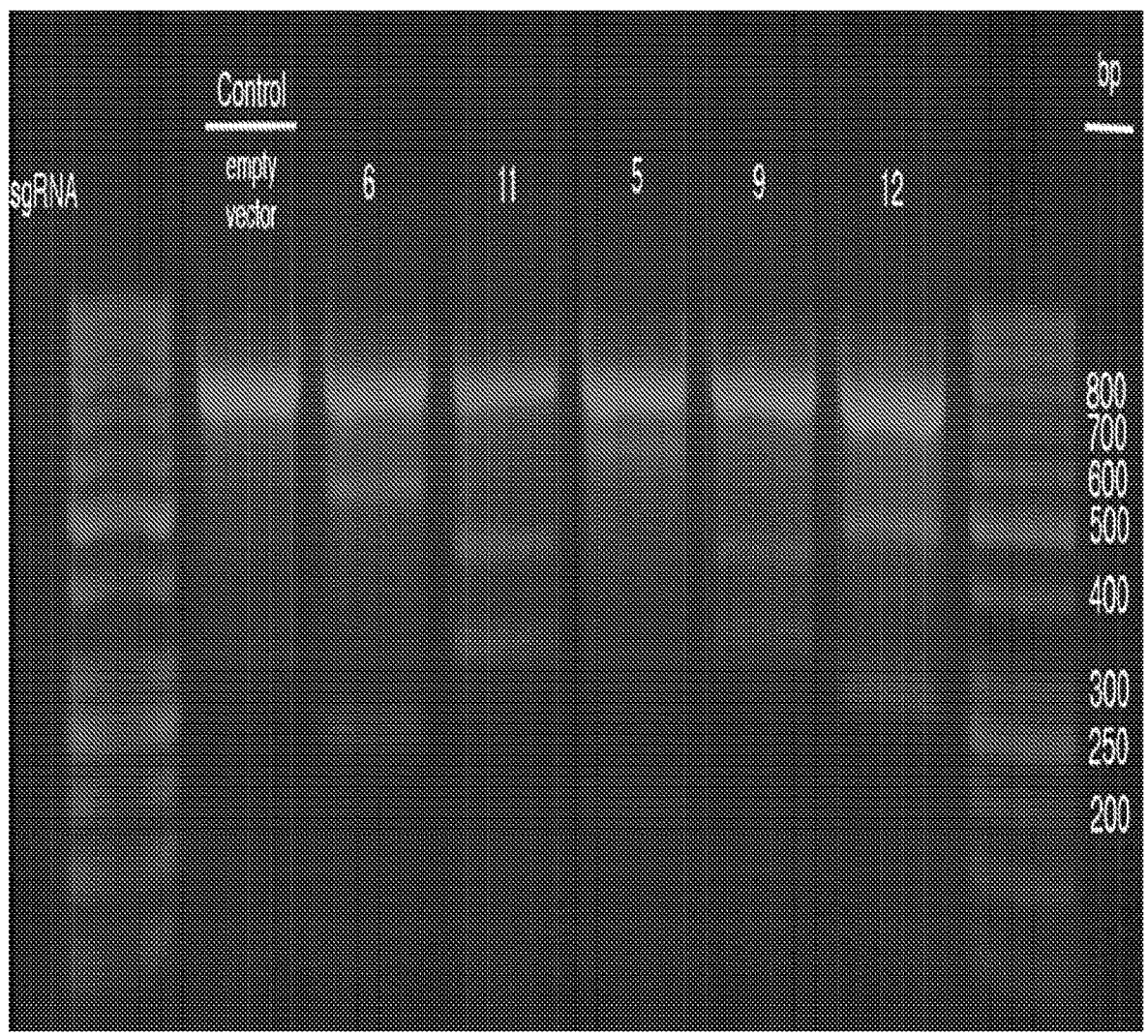
Figure 9C:
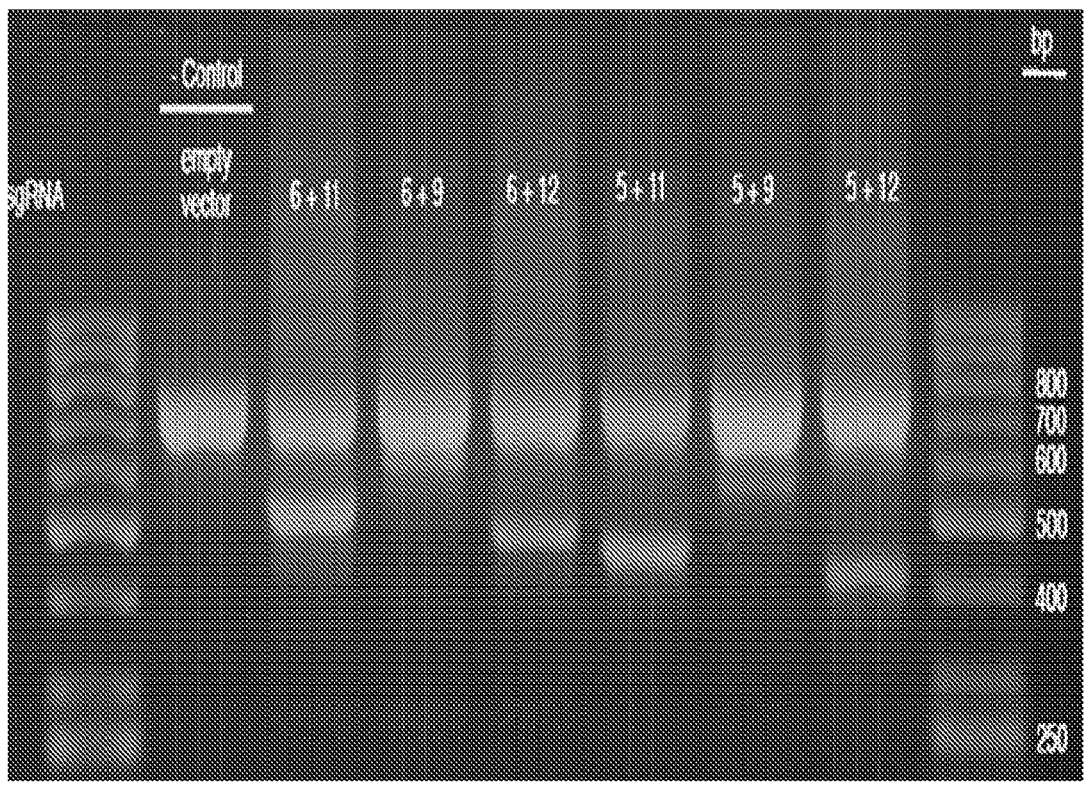

When sgRNA-px601 constructs were tested individually, the genomic DNA edits, predicted to be in the 3-50 bp range, were below the resolution of the 2% agarose gel used for separation and visualization of genomic PCR products (FIG. 9A). For each sgRNA tested, treatment of PCR products by surveyor endonuclease yielded 2 bands on the gel, indicating successful editing of the targeted Mypt1 sequence by sgRNA-px601 construct. As expected, for each experimental condition, the sum of the sizes of both nuclease products equals ~750 bp, the size of the parent (control) genomic DNA fragment as follows (in bP). sgRNA: 6: 250/500; 11: 320/430; 5: 120/630; 9:330/420; 12: 270/480. Only 1 product was observed for control DNA treated by surveyor endonuclease, reflecting the formation of homoduplexes only, due to the absence of mutations (FIG. 9B). Cells transfected with combinations of sgRNA-px601 6+11, 6+9, 6+12, 5+11, 5+9 and 5+12 had genomic edits of approximately (bp) 500, 600, 470, 450, 570 and 420 observed by standard PCR and separation of products by 2% agarose gel electrophoresis (FIG. 9C). Measuring of band intensities suggests that efficiency of Mypt1 E24 editing ranged from 10% (sgRNAs 6+9 and 5+9) to 40% (sgRNAs 6+11 and 5+11). As ~50% of cells in each experiment are successfully transfected as indicated by GFP expression, the true efficiency of this genome editing approach is likely double this number.

TABLE 1

| Guide name | Position: start-end | Strand | Sequence | PAM | Specificity score | Efficiency score |
|---|---|---|---|---|---|---|
| sgRNA1 | 155894-155913 | 1 | ATGTTTAGGCATGCCGATGT (SEQ ID NO: 5) | TGGAAT | 95 | 1 |
| sgRNA2 | 155925-155944 | 1 | GGTACTTAAAAGACGATCAG (SEQ ID NO: 6) | TAGGAT | 93 | 24 |
| sgRNA3 | 155974-155955 | -1 | ATGTGATTTTAAAAAGTAGA (SEQ ID NO: 7) | CAGAAT | 38 | 20 |
| sgRNA4 | 156000-155981 | -1 | ACTGTAAATGTTAATGTTTT (SEQ ID NO: 8) | TAGGGT | 43 | 1 |
| sgRNA5 | 156027-156046 | 1 | CATTATTTATTAATCTGGGA (SEQ ID NO: 9) | AAGAGT | 59 | 14 |
| sgRNA6 | 156099-156118 | 1 | GTATCTGAAAGGTGACCGGC (SEQ ID NO: 10) | AAGAGT | 92 | 46 |
| sgRNA7 | 156182-156201 | 1 | TTGCTTTTTGCATAACACCC (SEQ ID NO: 11) | CAGAAT | 82 | 29 |
| sgRNA8 | 156223-156204 | -1 | CCCTTAAATGATAAGCATTC (SEQ ID NO: 12) | TGGGGT | 76 | 2 |
| sgRNA9 | 156203-156222 | 1 | AGAATGCTTATCATTTAAGG (SEQ ID NO: 13) | GAGAAT | 68 | 37 |
| sgRNA10 | 156300-156281 | -1 | TTTATTTTAAACTTGTTTCA (SEQ ID NO: 14) | AAGAGT | 42 | 7 |
| sgRNA11 | 156349-156330 | -1 | TTATGTGTAGCATTAATGCA (SEQ ID NO: 15) | GTGAAT | 73 | 87 |
| sgRNA12 | 156361-156380 | 1 | ATACAAAGCTATAAAGTCAG (SEQ ID NO: 16) | TTGGAT | 60 | 32 |
| sgRNA13 | 156388-156407 | 1 | AATAATGGCTAGTACACATT (SEQ ID NO: 17) | GTGAGT | 72 | 13 |

Candidate sgRNAs for Genome Editing Targeting the Exon 24 of PPP1R12A

List of sgRNAs identified by Benchling for genome editing targeting the exon 24 of human PPP1R12A gene. sgRNAs are distributed between positions 155894 bp and 156407 bp of PPP1R12A gene sequence ENSG00000058272. All guides are 20 bp-long and have a NNGRRT PAM sequence immediately downstream their 3' end. The efficiency score measures the expected activity of the sgRNA on the target. The specificity score measures how specific the sgRNA is to the target location. Both scores are from 0-100, higher scores predicting better activity and specificity.

Various gRNAs can be generated by hybridizing the oligonucleotides below followed by cloning them into an Addgene pX601 plasmid for delivery.

sgRNA6 For
(SEQ ID NO: 31)
5'-CACC GTA TCT GAA AGG TGA CCG GC-3' sgRNA6 Rev
(SEQ ID NO: 32)
5'-AAAC GCC GGT CAC CTT TCA GAT AC-3'

-continued sgRNA11 For
(SEQ ID NO: 33)
5'-CACC G TTA TGT GTA GCA TTA ATG CA-3' sgRNA11 Rev
(SEQ ID NO: 34)
5'-AAAC TGC ATT AAT GCT ACA CAT AAC-3' sgRNA5 For
(SEQ ID NO: 35)
5'-CACC G CAT TAT TTA TTA ATC TGG GA-3' sgRNA5 Rev
(SEQ ID NO: 36)
5'-AAAC TCC CAG ATT AAT AAA TAA TGC-3' sgRNA9 For
(SEQ ID NO: 37)
5'-CACC G AGA ATG CTT ATC ATT TAA GG-3'

-continued

```
sgRNA9 Rev
                                           (SEQ ID NO: 38)
5'-AAAC CCT TAA ATG ATA AGC ATT CTC-3' sgRNA12 For
                                           (SEQ ID NO: 39)
5'-CACC G ATA CAA AGC TAT AAA GTC AG-3' sgRNA12 Rev
                                           (SEQ ID NO: 40)
5'-AAAC CTG ACT TTA TAG CTT TGT ATC-3'.
```

The present example uses CRISPR/Cas 9 for the novel purpose of targeting Mypt1 E24 as a method to lower blood pressure and cure hypertension and related diseases with a single treatment. Using in silico predictions of potentially efficient sgRNAs, followed by in vitro testing of candidate sgRNAs cloned into a vector containing the cassette for SaCas9 enzyme, ultimate genome "editor"—efficient genome editing of Mypt1 E24 in human-derived cells in vitro was effected. Interestingly, a total or partial excision of PPP1R12A E24 was achieved using relevant combinations of sgRNA-px601 constructs targeting intronic regions flanking E24 with an efficiency that reached 40%. These in vitro results are extremely promising and arise as the first steps towards the development of a new long-term—possibly curative—treatment for hypertension. Provided herein is the proof of principle that the designed sgRNAs-AAV vector constructs can achieve an efficient excision or inactivation of E24 from PPP1R12A genomic sequence. As a follow-up step, a set of AAVs bearing the sequence of selected sgRNAs singly and in combination as described above will be tested in vivo. sgRNA-px601 plasmid constructs will be sent to the MGH Vector Core in Boston for production of AAV viruses, each bearing the sequence of a single selected sgRNA (sgRNA6, 5 and 11). Purified AAVs will be returned to us. sgRNA-AAV (experimental group) or empty AAV vector (control group) will be infused by tail vein into mature mice. BP will be monitored by telemetry for a total duration of 6 weeks and BP values will be statistically compared between experimental and control groups. Normal mature mice and E 24 cKO mice will be used. The E24 cKO mouse model is a genetically engineered mouse model (see Example 1) and would offer an elegant means of testing for off-target effects of sgRNA-AAV constructs. At the molecular level, PPP1R12A E24 deletion will be assayed by PCR at the genomic DNA level and the mRNA level in arteries.

All selected sgRNAs for in vitro evaluation were initially confirmed as being compatible with use in murine models, as well as in humans thanks to the presence of the sgRNA targets and the presence of the appropriate PAM sequence in their immediate vicinity in human, mouse and rat. This highly simplifies the progression of work from in vitro experimentation on human cells, to in vivo experimentation on murine models and ultimately clinical study in humans if positive results are obtained in rodents. Genome editing targeting PPP1R12A E24 as described above would allow permanent lowering of BP and appears as a potential cure for hypertension and its sequelae including heart failure and stroke. These remain the number one cause of morbidity and mortality in the United States, and now world-wide, despite the many drugs that are available to treat these conditions. This approach has never been reported in animal models nor used in humans.

Example 4. Tissue-Specific Splicing of Mypt1 Alternative E24 in Human Arteries and a Novel Mouse Mini-Gene Reporter Isoforms of the Myosin phosphatase regulatory subunit (Mypt1) are generated by alternative splicing of 31 nt Exon 24 (E24). Studies in rodents support a model in which the expression of Mypt1 E24 splice variants in the vascular smooth muscle determine the sensitivity to NO/cGMP mediated vasodilation and thus regulation of blood flow and pressure. The current study examined the expression of Mypt1 E24 splice variants in human vascular smooth muscle and developed a novel mouse model to report on splicing of Mypt1 E24 in mouse tissues. The pattern of E24 splicing present in rodents was conserved in humans. In the large conduit vessels such as the cephalic artery and caval vein, E24 was detected at very low levels in the mature Mypt1 mRNA. In contrast in small arteries dissected from skeletal muscle biopsies, the ratio of E24 inclusion to skipping in the Mypt1 mRNA was ~60:40. In an attempt to model this in the mouse, a splicing reporter mouse was developed in which mouse E24 and flanking intronic sequence was inserted into a GFP-RFP splicing reporter which was then inserted into the ROSA locus to generate the E24 splicing reporter mouse. Inclusion of E24 in the mini-gene context patterned that of the endogenous E24. However the magnitude of inclusion was substantially less than endogenous E24 in tissues where E24 inclusion is the predominant variant, such as bladder and small arteries. This low level of E24 inclusion precluded the use of RFP as an in situ reporter of E24 inclusion. In conclusion, tissue-specific alternative splicing of Mypt1 E24 is conserved within the human arterial system. The developed splicing reporter mouse was of limited success. Issues to be addressed in an improved model include the amount of flanking sequence containing regulatory information, the heterologous splicing context, and other technical aspects of the splicing reporter model.

The purpose of the present example was to 1) determine if the highly specific pattern of splicing of Mypt1 E24 observed in rodent and avian vascular smooth muscle is also present in humans. While highly conserved Mypt1 E24 and flanking intronic sequence was identified in the human genome, there has been limited analysis of its expression in human vascular and other smooth muscle tissues 2) develop and test a Mypt1 E24 mini-gene GFP-RFP reporter construct for its ability to report on splicing of E24 in diverse mouse smooth muscle tissues in vivo (Dippold et al., *Am J Physiol Regul Integr Comp Physiol.* 2014; 307(3):R256-70; Konik et al., *J Mol Cell Cardiol.* 2013; 65:147-55; Lartey et al., *PLoS ONE.* 2016; 11(10):e0164352).

Methods

Animals

Figure 10:
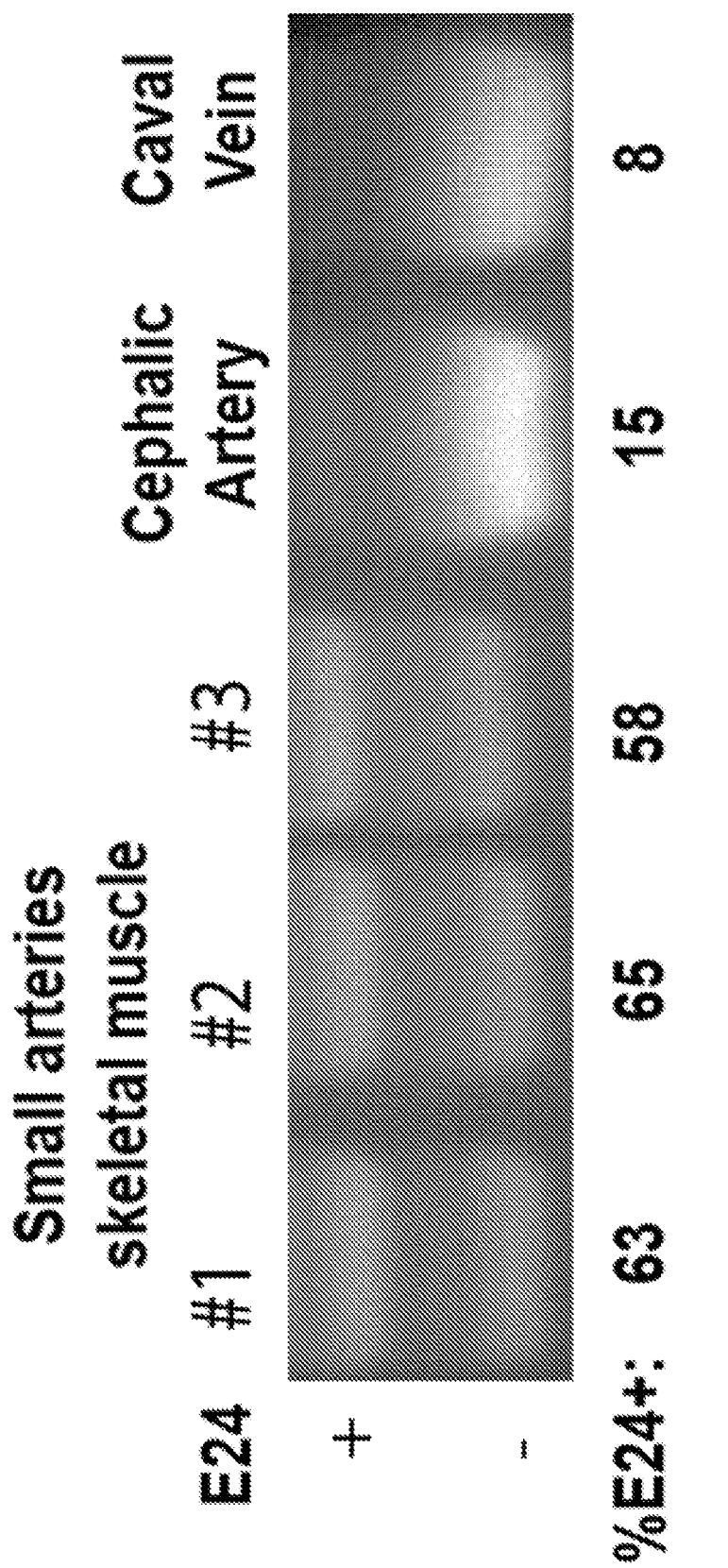
FIG. 10. Mypt1 E24 splice variants in human large and small blood vessels.

All mice were used in accordance with IACUC guidelines. E24 GFP-RFP reporter mice were generated as follows. An about 600 nt fragment of Mypt1 containing E24 and the highly conserved flanking intronic sequence was amplified by PCR and sub-cloned into the pFlare9a GFP-RFP splicing reporter plasmid (a kind gift of P. Stoilov (Stoilov et al., *Proc Natl Acad Sci USA.* 2008; 105(32): 11218-23). This was digested with BglII and Not1 to release a fragment containing Mypt1 E24 and EGFP-ds Red expression construct. This fragment was directionally sub-cloned into Not1 and BamH1 sited of the pENTR1A plasmid and then re-combined into the pROSA-DEST vector (from Addgene) using Gateway methodology (FIG. 10). This plasmid was used for injection into ES cells and creation of chimeric mice at UC Irvine facility. Mice were then bred and selected for germline transmission and further bred to homozygosity for E24GFP-RFP in the ROSA locus. These mice were crossed with SM22Cre expressing mice to obtain mice that were Cre+ and homozygous for E24GFPRFP at the ROSA locus (Lepore et al., *Genesis.* 2005; 41(4):179-84). The SM22Cre causes recombination of the stop-floxed reporter resulting in reporter expression in SMCs. Skipping of E24 would re-join the GFP coding sequence resulting in GFP expression. Inclusion of E24 would interrupt GFP coding sequence so that RFP would be produce. These mice appeared healthy as adults. Mice were genotyped by PCR.

RNA Purification and Assay of E24 Splice Variants

Human skeletal muscle biopsies were obtained as part of VA study. A small discarded portion of the muscle was placed in RNAlater™, a tissue RNA stabilization and storage reagent (Invitrogen/ThermoFisher Scientific, Waltham, Mass.), and taken to the laboratory where the small arteries were dissected and stored in RNAlater™ until further processing. Adult mice were euthanized and tissues dissected and stored at −80 C until processed. Samples were lysed by homogenization and total RNA column purified with RNeasy® Micro Kits (Qiagen, Germantown, Md.) as per manufacturer's instructions and as previously described. 100 ng of total RNA was used for reverse transcriptase reaction. The endogenous and exogenous Mypt1 Exon24 variants were measured using RT-PCR and gel separation of products. Adult SM22-Cre+ GFP/RFP reporter mice were euthanized via $CO_2$ inhalation followed by cervical dislocation. Tissues were immediately harvested for RNA isolation. The tissues harvested were lung, intestine, mesenteric arteries, kidney, liver, portal vein, bladder, and aorta. RNA was purified from these tissues using an a PureLink® RNA Mini Kit with an on-column DNase treatment (Ambion/ThermoFisher Scientific, Waltham, Mass.). RNA yield was quantified using a NanoDrop™ spectrophotometer (ThermoFisher Scientific, Waltham, Mass.). cDNA was synthesized from 100 ng RNA using VeriScrip™ reverse transcriptase (Affymetrix, Inc., Cleveland, Ohio). The RNA region of interest was PCR amplified with an annealing temperature of 55° C. for both the endogenous portion of the Mypt1 gene with E24 and the exogenous portion of the gene construct with E24. The products were gel separated using 2.5% agarose, and the bands were quantified using ImageJ, a Java-based image processing program developed at the National Institutes of Health and the Laboratory for Optical and Computational Instrumentation (LOCI) at the University of Wisconsin (Open Source License available). Percent exon in between endogenous & exogenous expression, as well as across tissue types, was calculated. Control samples without the reverse transcriptase were run to validate the assay. Human embryonic kidney (HEK) cells transfected with the E24 splicing reporter plasmid served as a control.

Imaging of E24 GFP-RFP Reporter Mice

Mice were perfusion fixed with 4% Paraformaldehyde (PFA). Various tissues were dissected out, post-fixed in 4% PFA, preserved in sucrose, and embedded in optimal cutting temperature compound (OCT). The tissues were sectioned at 8-10 microns using a cryostat. The slides were nuclear stained with DAPI and, after applying an aqueous mounting medium, covered with a coverslip. The sections were imaged on a Leica DMLB microscope for the spatial pattern of green & red fluorescence. Imaging was by confocal microscopy.

Results

Tissue-Specific Splicing of Mypt1 E24 is Conserved in Human Blood Vessels

A sensitive and quantitative PCR assay was used to measure the ratio of Mypt1 E24 included (E24+) vs skipped (E24−) mRNAs in RNA purified from the small resistance arteries dissected from skeletal muscle biopsies vs large conduit vessels obtained at autopsy. In samples obtained from three different patients there was more inclusion than exclusion of E24 from the mature Mypt1 mRNA (FIG. 10). In contrast, in RNA purified from the large vessels (cephalic artery and caval vein), there was minimal inclusion of E24 in the mature Mypt1 mRNA (FIG. 10). This pattern of splicing of Mypt1 E24 matches well with what has been reported in other species including pigs, mice, rats, and chickens (Reho et al., *Am J Physiol Heart Circ Physiol.* 2014; 306(2):H163-72; Zheng et al., *Microvasc Res.* 2014. Epub 2014/02/19. doi: S0026-2862(14)00035-1 [pii]).

A Mini-Gene Construct for the Study of Mypt1 E24 Splicing In Vivo

As described in Methods and FIG. 10 a mouse was generated with a Mypt1 E24 mini-gene splicing reporter construct inserted into the ROSA locus. The splicing from this mini-gene construct with that of the endogenous Mypt1 E24 was then compared. As previously reported inclusion of E24 is the predominate mRNA species in the mouse mesenteric arteries and other prototypical phasic smooth muscle tissues such as bladder (Reho et al., American Journal of Physiology—Heart and Circulatory Physiology. 2016; 310 (11):H1715-H24; Fu et al., *J Biol Chem.* 2012; 287(20): 16575-85; Zheng et al., *Am J Physiol Cell Physiol.* 2015; 308(4):C289-96; Llorian et al., *Nucleic Acids Res.* 2016; 17). Skipping of E24 predominates in the mouse aorta (27±4% inclusion), lung, kidney and intestine, the latter dependent upon which segment of intestine is analyzed (data not shown). Cells in culture, be they transformed (human embryonic kidney 293 (HEK293) cells) or primary cells (from adult human aorta) show minimal or un-detectable levels of inclusion of E24 in the mature Mypt1 mRNA.

A different pair of oligonucleotide primers was then used to specifically amplify the mini-gene derived mRNA and measured E24 skipping vs inclusion as described above for the endogenous Mypt1 mRNA. The reporter mice exhibit a pattern of alternative splicing of the mini-gene E24 that is similar to but not nearly as robust as for the endogenous transcript. The mini-gene E24 is present at very low or un-detectable levels in RNA from lung and kidney. The highest levels of E24 inclusion are present in MA and bladder though this still only occurs in less than 20% of transcripts. Aorta and small intestine have levels of E24 inclusion intermediate to those of highest and lowest expressers.

Imaging of GFP-RFP as Reporters of E24 Splicing In Situ

The Mypt1 E24 mini-gene construct was designed such that when E24 was skipped Green fluorescent protein (GFP) would be produced, and when included, a red fluorescent protein would be produced. Adult mouse mesenteric arteries were imaged by confocal microscopy to detect red and green fluorescent signals. The green fluorescence in the walls of the mesenteric arteries and other tissues was easily detected above the background auto-fluorescence. In contrast red fluorescence, which would be an indicator of E24 inclusion, was not detected above background.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

I claim:

1. A therapeutically effective method of lowering blood pressure in a subject, comprising genetically modifying a myosin phosphatase target subunit (Mypt1) gene in vascular smooth muscle cells of the subject, whereby the genetic modification of Mypt1 results in a deletion or inactivation of exon 24, the modification being accomplished by administering to the cells a clustered regularly interspaced short palindromic repeats (CRISPR)/CRISPR associated protein (Cas) system comprising:
   (a) a guide RNA (gRNA) molecule comprising a targeting domain which is complementary with a target domain sequence of the Mypt1 gene, the targeting domain being selected from the group consisting of SEQ ID NO:1, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and combinations thereof; and
   (b) a CRISPR associated protein 9 (Cas9) molecule or a nucleotide sequence encoding a Cas9 molecule.

2. The method of claim 1, wherein the method comprises administering a nucleic acid composition that comprises: (a) a first nucleotide sequence encoding the gRNA molecule and (b) a second nucleotide sequence encoding the Cas9 molecule.

3. The method of claim 1, wherein the Cas9 molecule is from *Staphylococcus aureus*.

4. The method of claim 3, wherein the target domain sequence is present immediately upstream of a sequence comprising NNGRRT.

5. The method of claim 2, wherein the CRISPR/Cas system is delivered to the cells by a virus.

6. The method of claim 5, wherein the virus is an adeno-associated virus (AAV), a lentivirus, a retrovirus or a combination thereof.

7. The method of claim 6, wherein the virus is an adeno-associated virus (AAV).

8. The method of claim 7, wherein the AAV is AAV9.

9. The method of claim 1, wherein only one allele of Mypt1 is genetically modified in the cells to delete or inactivate exon 24.

10. The method of claim 1, wherein two alleles of Mypt1 are genetically modified in the cells to delete or inactivate exon 24.

11. The method of claim 1, wherein the genetically modified gene produces a Mypt1 isoform that is sensitive to nitric oxide.

12. The method of claim 1, wherein the subject is a human.

13. The method of claim 1, wherein the targeting domain is selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and combinations thereof.

14. A vector comprising a CRISPR/Cas system for genetically modifying a Mypt1 gene, wherein the genetic modification of Mypt1 results in a deletion or inactivation of exon 24, and wherein the vector comprises
   (a) a nucleotide sequence encoding one or more gRNA molecules comprising a targeting domain which is complementary with a target domain sequence of the Mypt1 gene, the targeting sequence domain being selected from the group consisting of SEQ ID NO:1, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and combinations thereof; and
   (b) a nucleotide sequence encoding a Cas9 molecule.

15. The vector of claim 14, wherein the vector is a viral vector.

16. The vector of claim 15, wherein the viral vector is an adeno-associated virus (AAV), a lentivirus, a retrovirus or a combination thereof.

17. The vector of claim 14, wherein the virus is an adeno-associated virus (AAV), a lentivirus, a retrovirus or a combination thereof.

18. The vector of claim 17, wherein the virus is an adeno-associated virus (AAV).

19. The method of claim 18, wherein the AAV is AAV9.

20. The vector of claim 14, wherein the Cas9 molecule is from *Staphylococcus aureus*.

* * * * *